US007072769B2

(12) United States Patent
Fletcher-Haynes et al.

(10) Patent No.: US 7,072,769 B2
(45) Date of Patent: Jul. 4, 2006

(54) EXTRACORPOREAL BLOOD PROCESSING INFORMATION MANAGEMENT SYSTEM

(75) Inventors: Peter Fletcher-Haynes, Bailey, CO (US); William Sweat, Lakewood, CO (US); Richard Judy, Littleton, CO (US); Scott Butzke, Littleton, CO (US); Kim Pemberton, Greenwood Village, CO (US); Frank Corbin, III, Littleton, CO (US); Robert W. Langley, Westminster, CO (US); Steven Gage Urdahl, Golden, CO (US); Christopher Fletcher, Superior, CO (US)

(73) Assignee: Gambro, Inc., Lakewood, CO (US)

( * ) Notice: Subject to any disclaimer, the term of this patent is extended or adjusted under 35 U.S.C. 154(b) by 1014 days.

(21) Appl. No.: 09/797,325

(22) Filed: Mar. 1, 2001

(65) Prior Publication Data

US 2001/0034614 A1   Oct. 25, 2001

Related U.S. Application Data

(60) Provisional application No. 60/186,123, filed on Mar. 1, 2000.

(51) Int. Cl.
*G01N 33/48*   (2006.01)
*G01N 33/50*   (2006.01)

(52) U.S. Cl. .............................. 702/21; 702/30; 702/31; 702/32

(58) Field of Classification Search .................. 702/21, 702/30–32; 382/134, 133; 707/1–206
See application file for complete search history.

(56) References Cited

U.S. PATENT DOCUMENTS

| 5,658,240 | A | * | 8/1997 | Urdahl et al. .............. 604/6.01 |
| 5,769,811 | A | * | 6/1998 | Stacey et al. .............. 604/4.01 |
| 5,915,240 | A | * | 6/1999 | Karpf .............................. 705/2 |
| 5,964,724 | A | * | 10/1999 | Rivera et al. .............. 604/5.04 |
| 6,046,761 | A | * | 4/2000 | Echerer .................... 348/14.01 |
| 6,113,554 | A | * | 9/2000 | Gilcher et al. .............. 600/573 |
| 6,233,525 | B1 | * | 5/2001 | Langley et al. ............... 702/21 |
| 6,256,643 | B1 | * | 7/2001 | Cork et al. .................. 707/205 |
| 6,581,011 | B1 | * | 6/2003 | Johnson et al. ............... 702/19 |
| 6,673,314 | B1 | * | 1/2004 | Burbank et al. .............. 422/44 |
| 6,730,054 | B1 | * | 5/2004 | Pierce et al. ............... 604/6.01 |

* cited by examiner

*Primary Examiner*—Marc S. Hoff
*Assistant Examiner*—Anthony Gutierrez
(74) *Attorney, Agent, or Firm*—John R. Merkling; Edna M O'Connor; Laura M. Butterfield

(57) ABSTRACT

A blood component collection system with manipulation and optimization capabilities. In one embodiment, process parameters are derived from an input/configured predetermined blood component yield and which is based upon the maximization of at least one process parameter. Thereafter, the blood component collection procedure is performed with these derived process control parameters. In another embodiment, process parameters are derived from an input total procedure time from a maximized value for at least one of the other process control parameters so as to maximize blood component yield in this fixed time. Thereafter, the blood component collection procedure is performed with these derived parameters.

8 Claims, 44 Drawing Sheets

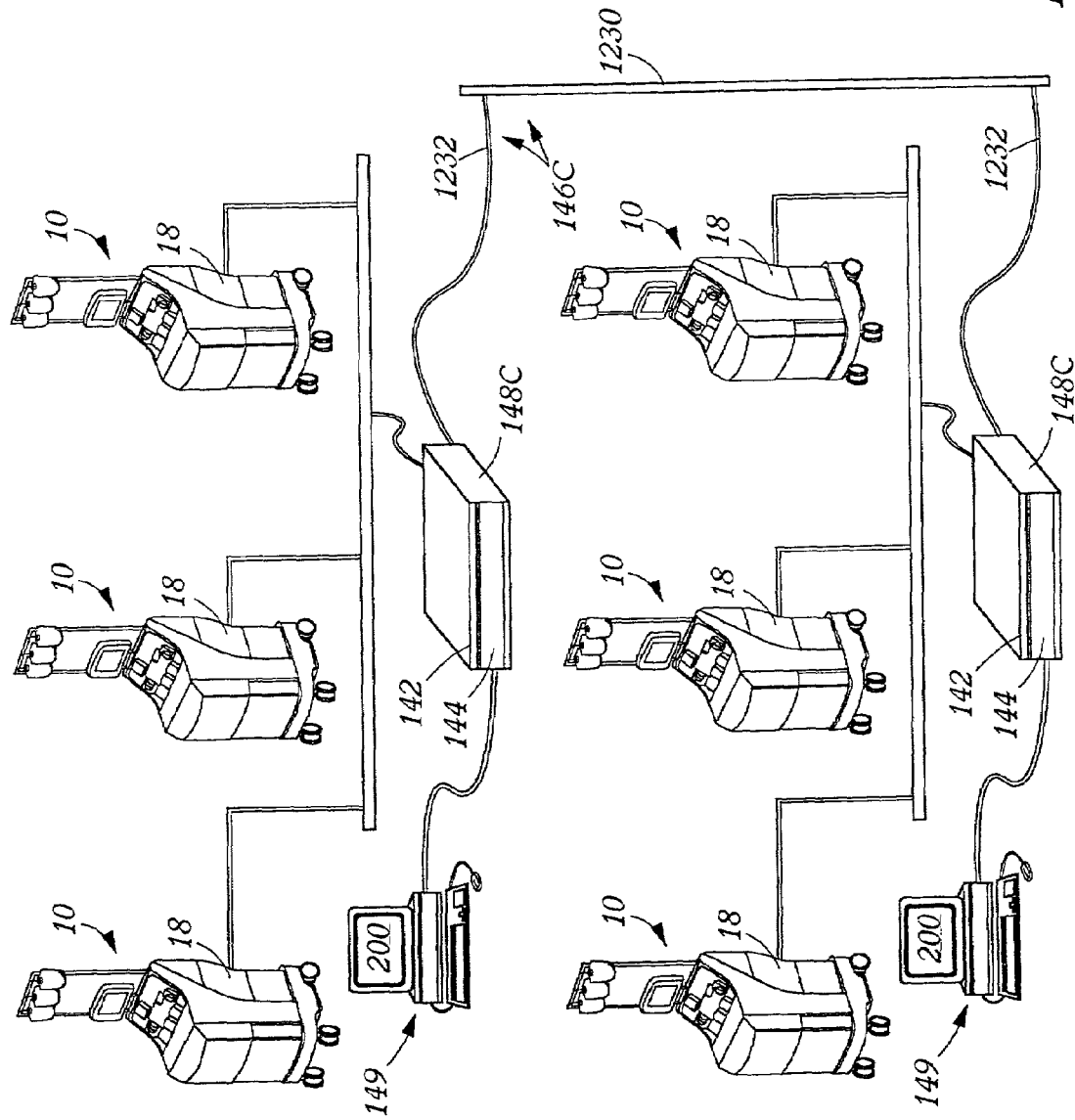

Procedure Record

| Unit Number : | 1 | | | | Date : | 09/20/00 | |
|---|---|---|---|---|---|---|---|
| Facility Name : | Gambro BCT | | | | Machine Type : | Test | |
| | | | | | Machine ID : | grace | |
| Donor Name : | Grace K Hui | | Gender : | Female | Date of Birth : | 10/02/1980 | |
| Donor ID : | 1 | | | | Blood Type : | O+ | |
| Height : | 120 cm | (b) | Weight : | 50 kg | (c) | Temperature : | 98.6 C |
| Blood Pressure : | 120/80 mmHg | | Pulse : | 90 beats/min | | TBV : | 8500 ml |
| Pre-run Hemoglobin : | 15 g/dL | | Platelet Pre-Count : | 4.0 x1000/μL | (a) | Access : | right |
| Post-run Hemoglobin : | 15 g/dL | | Platelet Post-count : | 4.0 x1000/μL | | Return : | left |

Procedure Targets : RBC/PLT 15 ( 300 min.)

| | Platelet | Plasma | RBC | Whole Blood |
|---|---|---|---|---|
| Volume (ml) : | 350 | 300 | 500 | |
| Yield (E11) or Packed Cell Vol (ml) : | 3.6 | | 400 | |
| Conc. (x1000/μL) or Collect Hct (%) : | | | 80 | |

End of Run Summary :

Procedural

| Procedure Tim (minutes) : | | | | 8520 |
|---|---|---|---|---|
| Total AC Used (ml) : | 20 | Blood Volume Processed (ml) : | | |
| Replacement Fluid Volume (ml) : | 50 | AC to Donor (ml) : | | 30 |

Final Product Predictions :

| | Platelet | Plasma | RBC | Whole Blood |
|---|---|---|---|---|
| Volume (ml) : | 300 | 100 | 250 | 600 |
| Yield (E11) or Packed Cell Vol (ml) : | 3.5 | | 200 | |
| Conc. (x1000/μL) or Collect Hct (%) : | 1167 | | 80 | |
| AC in product (ml) : | 10 | 20 | 20 | |

*Figure 6M*

EXTRACORPOREAL BLOOD PROCESSING INFORMATION MANAGEMENT SYSTEM

This case claims the benefit of priority of U.S. provisional patent application Ser. No. 60/186,123, filed on Mar. 1, 2000.

FIELD OF THE INVENTION

The present invention generally relates to the field of extracorporeal blood processing systems and, more particularly, to providing information management and/or data manipulation and/or optimization capabilities to, in and/or with such systems.

BACKGROUND OF THE INVENTION

The utilization of blood taken from donors and transfused into recipients is well known for purposes of treating medical conditions. More recently, selected blood components have been separated and collected from donated blood for subsequent transfusion into recipients for the more specific therapeutic benefits of those particular blood components. The primary blood components of current interest in many separation and collection technologies include platelets, red blood cells, white blood cells, stem cells and plasma.

In the harvesting of blood components, blood is removed from a donor through a needle assembly or other blood access device and may thereafter be processed by centrifugation or other appropriate separation techniques to isolate and collect the desired components. This procedure is often carried out very effectively in an on-line procedure wherein blood is removed from a donor, processed in and through a disposable extracorporeal fluid circuit to obtain the desired components, and the uncollected components thereafter returned to the donor. Two illustrative blood component collection systems which provide for this type of on-line blood component collection procedure are the COBE® Spectra™ and Trima® apheresis systems which are commercially available from the assignee of the present application.

The yield of a particular collection of blood components from such a process is an important factor in the ultimate usefulness of those particular components. For instance, in the United States a minimum yield is associated with a collected blood component product in order for that product to meet certain criteria and qualify for use as a transfusable blood component product. The COBE® Spectra™ and Trima® apheresis systems presently accommodate for this requirement by processing certain donor biological data such as height, weight, gender, and platelet pre-count or hematocrit, together with pre-configured and/or operator-input data such as the total procedure time, and system-related data such as the type of collection procedure (e.g., single or double needle) and collection efficiency to generate certain process parameters such as the inlet flow to the apheresis centrifugation device (including, for example, the combined flow of whole blood from the donor plus typically a flow of anticoagulant). These apheresis machines then generate a predicted blood component yield from these data as well.

An additional consideration presently in the United States, for example, relating to blood component yield is that the yield is determinative of the product classification. With regard to platelets, a single platelet product is presently considered to be a collection of $3 \times 10^{11}$ platelets and a double platelet product is considered to be a collection of $6 \times 10^{11}$ platelets. If a collection is between $3 \times 10^{11}$ and $6 \times 10^{11}$ platelets, it is still considered to be a single platelet product. This classification as a single or double platelet product is important to blood component collection facilities (e.g., blood banks/centers) since a double platelet product may have a higher selling price than a single platelet product and may also have a greater benefit for the recipient/patient. The yield of a particular collection of blood components may also be a relevant consideration for certain therapeutic treatments (e.g., red blood cell or plasma exchanges).

Furthermore, advances in blood component collection technologies offer the possibility of collecting multiple combinations of products from a single donor. These products can be defined within a large range of volumes and contents. Add to this multitude of collection choices, a multitude of donors with differing physiologies, each being subject to potential variations in collection procedures to yield a potential very large plurality of choices of products to be collected, as may be desired.

Still other important considerations relating to blood component collection systems relate to the donor and product demand. For instance, blood component collection facilities are not only experiencing an increase in the overall demand for blood components, but the demand now typically varies between the blood component types as well. Moreover, the supply of donors is unfortunately inadequate in many cases, and donor time constraints are becoming more prevalent. Furthermore, obtainable yields from a given donor may vary from one blood component to another, i.e., one donor may be a better platelet source than a red blood cell source.

The result is a large number of variables which must preferably be simultaneously managed in order to meet the blood bank collection goals which will thus also satisfy the needs of the ultimate hospital or like customer. Computerized information systems are tools which are beginning to prove useful in assisting in controlling parts of blood collection processes. This will likely further impact, if not transform, how blood banking will be managed in the future. Computer information systems may prove important in aiding the provision of just-in-time supply of products to meet customized demand for blood products and better satisfying the individual needs of patients and providers. Automated component collection systems will also allow for flexibility in producing customized blood products in a just-in-time fashion from potentially fewer donors to help meet the demands of patients and providers.

In view of the foregoing, it should be readily understood that better management of the various aspects of blood component collection processes and systems is increasingly desirable in providing preferred product collection and customer supply options.

SUMMARY OF THE INVENTION

The present invention relates in one application to a blood component collection system and the provision of management capabilities which may include the incorporation of data manipulation and/or optimization principles. Generally, the present invention preferably utilizes an information management system which provides simplified donor data storage and control as well as communications with actual blood component collection machines to both ease and optimize the set-up and operation thereof. The principles of data manipulation and/or optimization are further improved also, particularly in terms of the individual donor, a given pool of donors, the particular blood component collection system, and/or the blood component product or products to be collected. For instance, the present invention may be adapted to provide for the collection of a predetermined quantity of at least one predetermined blood component, or more typically the collection of such blood components within a particular range in a "minimum" amount of time, and/or for the collection of a "maximum" quantity of at least one predetermined blood component in a fixed amount of time, all based upon certain donor and/or blood center defined process conditions. Moreover, the present invention may be adapted to provide for blood component inventory control by basing donor selection and/or collection procedure selection (in terms of the type of blood component to be collected) on blood component demand and/or existing inventory. In addition, the present invention may be adapted to provide for further donor management by collecting that blood component type or types from the donor which provides a maximum yield.

A preferred central computational, data storage, manipulation and communication system serving as the primary basis of the present invention is preferably a software-type of application run in tandem with one or more hardware devices including, for example, a data input device, a data storage device, a data manipulation device and one or more communications devices which connect in data communication relationship one or more of such input, storage and/or manipulation devices to at least one blood component separation and/or collection machine. The software application may be and in preferred form is operable in/on a Microsoft® Windows® software platform (or a similar such system) that allows blood donation center operators to prepare apheresis machines and donors for apheresis donations in an automated manner. The present system may preferably have two primary components, a computation/manipulation application with associated software and devices, and a server system also including associated software and devices. The computation/manipulation application is used by the blood center staff to perform data management and/or manipulation functions. The server system is used preferably to store data and provide communications with the apheresis machines and/or other information systems. In a typical setting, one or more operators from different locations within a single blood center and/or remotely from various disparate blood centers (and/or other sites) can communicate with a centralized server system to perform specific functions such as donor check-in, preparing a donor for a particular donation, or finalizing and/or preparing reports on collection activities, inter alia.

An important purpose of the present system is to address various challenges in the area of blood donation management including increasing productivity, better donor qualification/utilization and improved product quality control and disposition.

Increased productivity may be accomplished through centralized management of apheresis machine configurations. Operators and/or system administrators may easily create and store several configurations using the present system on a centralized server/computer or a like environment. These configurations are preferably kept in a centralized database and can be downloaded to each apheresis machine on a permanent or a temporary/one-time donation basis. This reduces the inherent contemporary difficulty of editing apheresis machine configurations by allowing the operator to update a centralized configuration and not be required to repeatedly make the same change on several standalone apheresis machines.

Donor qualification/utilization may be improved through procedure customization and/or optimization. Each donation may be customized by this system to account for the current needs of a blood center and/or optimized by what each particular donor is eligible/qualified for or capable of donating. This allows the operator to determine what product or combination of products will best be collected even before the donor is connected to the machine. It also allows the blood center operators to see what tubing set is required for the donation. With this information the customer can avoid wasting tubing sets and reduce incomplete procedures. Decision support for donor eligibility is a preferred beneficial feature of the system. At a minimum, eligibility may be determined by the interval between donations, the number of donations previously given, the blood component loss over a period of time, and other donor screening issues.

Another important, yet optional feature of donor qualification/utilization and management in using a system of the present invention involves donor recruitment. The present invention provides a tool which may analyze and predict donation outcomes prior to running a donor on an apheresis machine. Such a tool can use donor and procedure information from the central database or optionally from an imported text file containing the required minimum information. Thus, such predictions can be used independently of actual runs on donors, even those actual runs involving the system of the present invention. These predictions may also be independent of procedures not currently entered into the central database, but rather from data generated by the blood center or data obtained from the blood center information system. Donor data may refer to a particular donor or to a statistical distribution of donor population. At a minimum, the system of the present invention may preferably analyze the outcomes of the following three scenarios: a) a single donor relative to many possible procedures; b) many donors relative to a single type of procedure; and c) many donors relative to many possible procedures.

Improved product disposition may be enhanced through the provision of alterable prioritizations of the product needs of a blood center. The present system presents the capability of providing a prioritization of which products are preferred to be collected. This allows the blood center to begin to incorporate the concept of demand drive where donors are used to fill existing and/or imminent product needs. This also reduces waste from the over collection of certain products. The system also presents the capability to tailor a blood center's priorities by blood type, CMV status, and/or HLA type matching.

The present system also provides for quality control (QC) in the entry of laboratory data for products collected by blood separation devices operated in accordance with the present invention. Data may include (but is not limited to) measured yields, volumes, concentrations, product contaminants, and pH levels. The present system provides the capability to associate anomalous QC lab data to donation events and to generate exception reports where the device prediction and QC lab results may differ. The present system can also utilize this data to automatically calculate and adjust a separation device's yield calibration value, i.e., a yield scaling factor, depending on the particular device type.

Overall procedure and apheresis machine management may also be improved by recording procedure history information for each apheresis donation and storing it in a central database. Thus, the system may contain a detailed log of each donation. These logs can include procedure comments, tubing sets used, alarms experienced, adjustments made, and machine run summary information. Operators may additionally annotate this procedure history information and/or obtain reports using such logged information.

To implement the above and other features of the present invention, it is preferred that a central computational/data storage system be established according to the present invention so that it communicates with each of one or more blood collection machines, preferably apheresis machines, in both directions (even though one-way communications may be desirable in certain situations). Two way communications provide for directing to each machine configuration information of both temporary and permanent natures, procedural lists and priority information, donor vital information, including height, weight, gender, blood component pre-counts and total blood volume (TBV), as well as donor identification which may include a donor picture with the donor's name and perhaps the date of birth. The centralized system may then also communicate in the reverse direction with each machine to retrieve from each apheresis machine immediate information regarding conditions such as alarms, procedure adjustments, and run progress (product collection information) for monitoring purposes. It also provides for retrieving end of run summary information and run logs after each procedure is complete. The centralized system can also use data from the apheresis devices to detect and isolate potential maintenance problems before they manifest themselves to the blood center. These can then be reported so that preventive maintenance may be performed.

The present system preferably uses prediction algorithms like those used in the Trima® and/or Spectra™ apheresis machines. Moreover, the prediction algorithms can also be applied to individual donors, a reference donor list, and/or ranges of donors within the database. This capability is helpful to predetermine donor eligibility for specific product collections, and what products would be available given specific apheresis machine configuration settings.

The present system has been developed with an open architecture to provide integration capabilities and collaborative capabilities with other computing environments (such as Mak and/or Wyndgate donor database information systems) and/or with other component separation machines (such as the Haemonetics and/or the Baxter series, e.g., the MCS+ and/or the Amicus and/or CS-3000 apheresis machines, inter alia). This ultimately will allow ancillary applications to be used. For example, this allows for the manipulation and formatting of donor identification data and/or images obtained from other information or software systems. Bar code capability is another preferable alternative which may be incorporated into the present system. Any field entry point which could/would require keyboard data entry could be filled using a bar code reader. In addition, special entry fields such as unit or batch number, manufacturer and expiry dates of disposable tubing sets may be fully decoded utilizing administratively editable decoding information; an example is manufacturer identification of a disposable tubing set.

Products can also be customizable from a collection standpoint. This is a potential first step toward a "dosing" model whereby components may be collected in quantities matching specific medically or doctor prescribed doses. These customizable products, although perhaps not directly donor specific, could also be set up in a way to take care of situations such as a "first time" donor or persons known as "clumpers," i.e., those persons whose component products show a certain tendency to clump or aggregate.

After determining which product or products are to be collected, each donor can be assigned to a specific apheresis machine. Monitoring real-time machine status from a central system is useful to determine to which machine each donor should be sent.

The present system has been designed to satisfy an optional yet desirable three room operational flow scenario. The basic three room scenario involves processing donors sequentially through three steps which may correspond to three different rooms; namely, donor registration or reception, donor interview/screening and donor utilization rooms. This model has been suggested for providing smooth operation of the blood component collection process.

During or after the run, numerous standard reports may be made available to provide the donation center information related to specific runs, sequences of runs, exceptions, etc. Although the reports are preferably standardized, customization may also preferably be made possible through the simple use of report wizards. The present system preferably also utilizes an industry standard report engine.

The central database provides the system with the capability of storing and maintaining data relevant to the entire blood component collection process such as, donor demographic information, machine configuration information, run information and lab result information. Lab data can also be entered into the run record to complete the product collection run record. This data can be used to provide feedback to the process. The communication software and hardware enable the pulling of data from and transmission of data to a common or central data repository.

This system may be used in a stand-alone configuration or in collaboration with a blood banking information system, especially for transfer of donor demographics and like donor identification information. The blood center information system is preferably considered the master when linked. Fire wall protection may be provided through password protection schemes, message formatting requirements and/or hardware communications interfaces. This provides the assurance that the integrity of the apheresis machine is maintained during connectivity of this system with such machines(s) and/or with other systems. The present system can also utilize a "standard" customer network for communications between a central system server and operators. This concept of collaborative networking particularly with pre-existing networks can minimize the "re-wiring" that otherwise might have been necessary.

Connectivity may also be utilized to provide collection data to the blood bank information system after the run is complete. This two-way communication strategy allows the present system to optimize the procedure and device selection based on the blood center's current priorities, rather than making these selections less-optimally at donor registration time. The as-run collection data may also synchronize the blood bank information system to the actual products, yields, and volumes donated.

Further, this system preferably utilizes formal and de-facto standards such as SQL interfaces to the database, ethernet protocols for communications, and preferably Oracle® reports for report generation.

In the present system, an apheresis machine, which is preferably also operable in an off-line mode, may upload run information to a central server system when the apheresis machine is connected on-line with the central server system. This feature could also be used for mobile or satellite operations.

An additional preferred functionality is connectivity with a blood center information system. Donor data will preferably be down-loadable to the central server system of the present invention from the blood center information system.

This will allow real time updating of donor data in the central database of the present invention from the database of the blood center information system. Other alternatives of the present system may also include connectivity of the central data manipulation and/or storage system to apheresis machines from a plurality of manufacturers.

Of the various methods of data transfer available, an option is a web server set-up. With specially developed applets, this allows the local user or a remote user (with permission) to browse the operator∝s database for pertinent information. Thus, this system can also be accessed remotely and provides an external "gateway" to run-logs from each apheresis machine. Security can be established to obscure sensitive data. An administration/security optional feature would allow the system to be configured with the concept of user types for security. A system administrator would have the most privileges and a guest would have the least number of privileges.

The present system provides an opportunity to circumvent shortcomings in the operational procedures forced on a blood center by the use of pre-existing blood bank software. Specifically, the present system may overcome the problem of a blood bank software system pre-selecting blood components to be collected rather than having the present system perform this selection process. The way this is achieved is unique in that data is exchanged with the blood bank software system during the process flow of information. This is different from having either system depend on inputs from the other system and then wait for outputs.

The present invention also preferably may be characterized as a blood component collection system having blood component product-based or time-based optimization capabilities. One embodiment comprises a method for collecting at least one predetermined blood component (e.g., a collection of platelets or red blood cells or plasma) from a source of whole blood using a blood component collection system which includes a blood component collection device running according to a particular collection procedure. More particularly, a desired yield of the predetermined blood component(s) may be identified (such yield including a single yield or range of yields) and biological data relating to the source of whole blood is provided to the blood component collection system. This data may also include statistically developed modifications based upon categories of data for multiple sources of whole blood as contained within the central server systems. Also, a value or magnitude may be associated with each of the various process parameters used in the collection procedure. A magnitude of at least one of these process parameters is preferably derived from the biological data and the desired yield and optionally also the statistically derived data from a plurality of whole blood sources. These magnitudes, including all magnitudes of process parameters derived from the desired yield, are input to the blood component collection system. Thereafter, the collection procedure is performed with the blood component collection device and with the input process parameters to collect the desired yield of at least one predetermined blood component(s) from the whole blood source.

In a time-based optimization method, a total procedure time for the collection procedure is identified (e.g., based primarily upon donor time availability). One potential inlet flow to the system is derived from at least this identified total procedure time. Another potential inlet flow to the system is derived which provides an "optimum" collection efficiency and is effectively the apex of a bell-shaped yield/inlet flow curve (i.e., the inlet flow which provides the maximum blood component yield). Consequently, if the total procedure time-based inlet flow is greater than the maximum yield-based inlet flow, and thus is an inlet flow on the decreasing slope portion of the yield/inlet flow curve, the maximum yield-based inlet flow magnitude is used in the performance of the collection procedure. However, if the total procedure time-based inlet flow is less than the maximum yield-based inlet flow, and thus is an inlet flow on the increasing slope portion of the yield/inlet flow curve, the total procedure time-based inlet flow magnitude is used in the performance of the collection procedure.

The subject invention provides greater efficiency in blood component collection and management. For example, the present invention can be used to compare blood bank/center component inventories with projected needs, and adjust collection procedures to meet these needs. Further, the present invention provides benefits to donors. In particular, certain information relating to the donor's physical and medical characteristics may be stored in the system and utilized during subsequent visits by the donor to derive magnitudes for the various process control parameters. For example, for a donor with an anticoagulant intolerance, the magnitude of the anticoagulant infusion rate may be set so as to not exceed the donor's tolerance.

The present invention may be implemented as a computer process, a computing system or as an article of manufacture such as a computer program product. The computer program product may include a computer storage medium communicatively connected to and/or readable by a computer system and may include encoding of a computer program of instructions for executing a computer process. Such a computer program product may also be a propagated signal on a carrier readable by a computing system and may also include encoding of a computer program of instructions for executing a computer process.

These and other features of the present invention can be better understood from the following detailed description of a preferred embodiment of the present invention taken in conjunction with the accompanying drawings which are briefly described below.

BRIEF DESCRIPTION OF THE DRAWINGS

FIG. 1D is still another schematic representation of a blood processing information management system in accordance with principles of the present invention;

FIGS. 2A–2I are display screen depictions of data entry, retrieval and/or manipulation display pages for use in accordance with the present invention;

FIGS. 6A through 6M are another set of display screen depictions of data entry, retrieval and/or manipulation display pages for use in accordance with the present invention;

DETAILED DESCRIPTION

The present invention will be described with reference to the accompanying drawings which assist in illustrating various pertinent features hereof. One application of the present invention involves one or more blood component collection systems which separate, remove, and collect at least one type of blood component (e.g., platelets, red blood cells, stem cells, white blood cells, plasma) from a source of whole blood (e.g., a donor) through utilization of a collection procedure derived from a typically site-configured and/or operator-input goal or set of goals and may optionally also include a "maximization" of at least one process control parameter. This type of maximized parameter derivation is referred to herein as an "optimization process" and the derived process control parameters may be referred to herein as "optimal values."

Figure 1A:
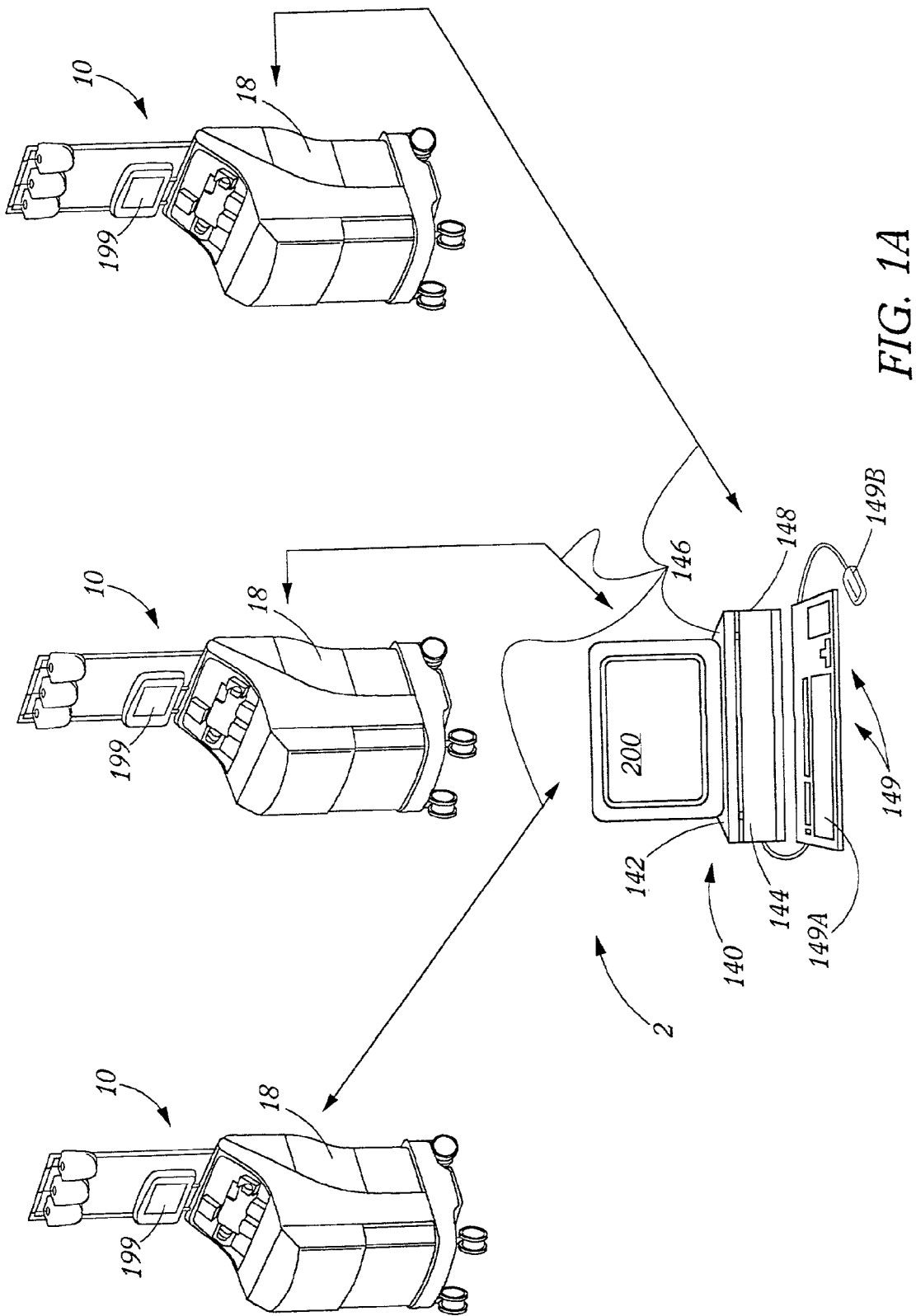
FIG. 1A is a schematic representation of a blood processing information management system in accordance with principles of the present invention.

Referring to the schematic of FIG. 1A, a first alternative schematic representation of the present invention is shown as including a blood component collection and information management system generally identified by the reference numeral 2. The system 2 would typically be implemented at a blood bank/center (not shown in FIG. 1A). The system 2 may include a substantially centralized computing/data storage assembly 140 (e.g., including an appropriate microcomputer and/or microprocessor(s) such as a Windows®-based standard desktop or laptop computer (or other like platform(s)), including therein or communicating with at least one memory device with corresponding appropriate software, etc. (not shown separately in FIG. 1A)) and at least one blood component separation/collection assembly (three shown), each generally identified with respective reference numerals 10 (in FIGS. 1A–1D). Each such separation collection assembly 10 preferably includes a blood component separation and collection device 18 as an integral part thereof. As will be discussed below, the centralized computing/data storage assembly 140 (or at least a portion thereof) and the associated blood component collection assemblies 10 are preferably appropriately interfaced with each other in electronic or electromagnetic data communication relationship as will be described, but may also and/or alternatively be disposed in a physically separate disposition from each other particularly during non-communication operation. That is, component separation/collection, data communication, retrieval, manipulation, and optimization procedures in accordance with principles of the present invention are not limited to being performed at any particular physical location of apheresis machines(s) 10 relative to a central assembly 140. Furthermore, data entry, manipulation and storage may still be performed at/on each machine 10 using, for example, respective interfaces, which here are shown as preferred touchscreen input/output devices 199.

Figure 1B:
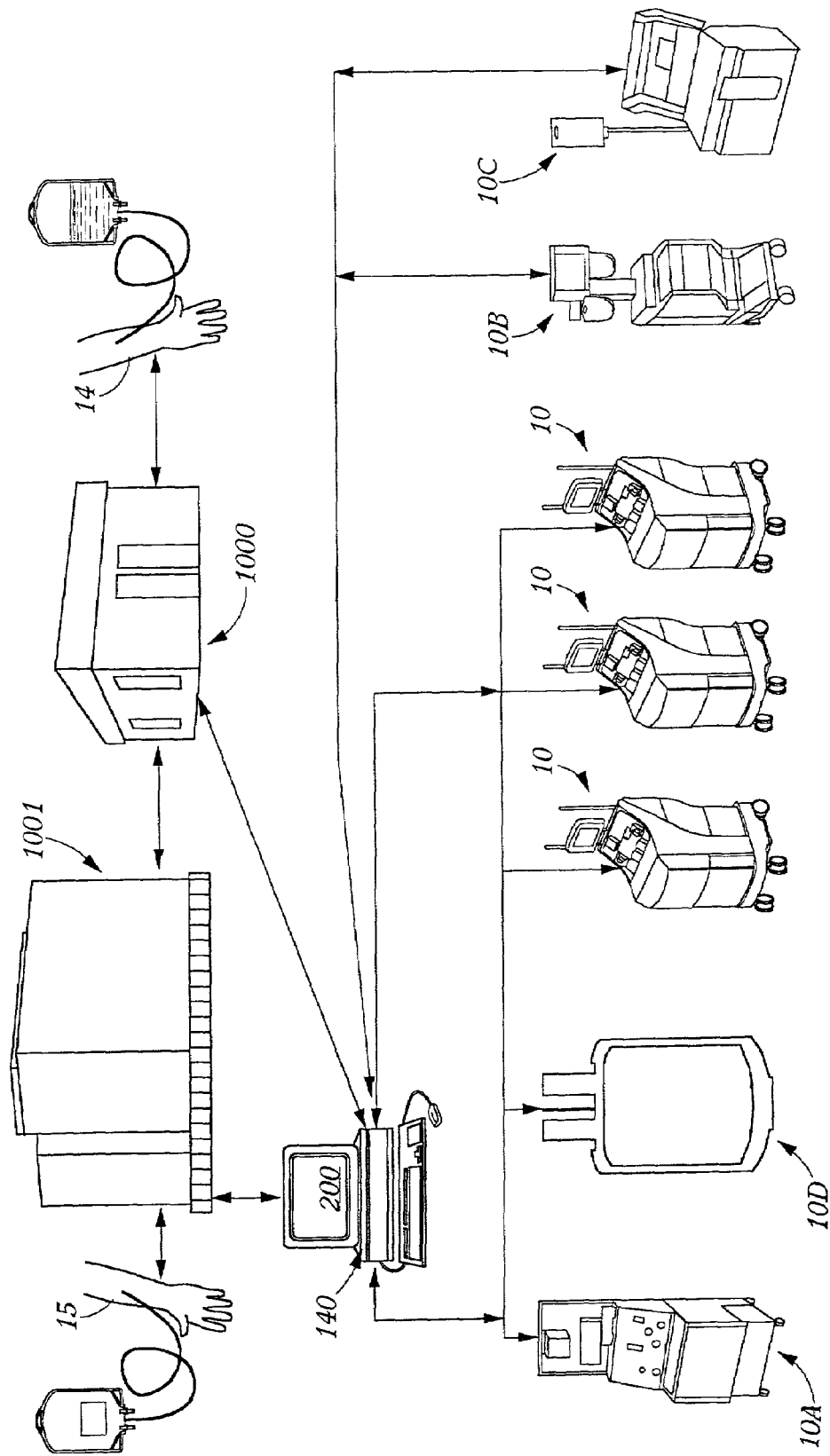
FIG. 1B is another schematic representation of a blood processing information management system in accordance with principles of the present invention.

A further aspect of the present invention is shown in more detail in FIG. 1B wherein a centralized computing/data storage assembly 140 is shown schematically disposed in communicative relationship with various types of blood component collection machine assemblies 10 as well as to either a discrete blood center information system within a blood center 1000 or a hospital information system within a hospital 1001, or both. Thus, as will be described in further detail below, a centralized computing/data storage assembly 140 may preferably make broad use of multiple communication connections (including satellite and/or wide area networks (WAN's), for example). Note also that though preferable connections to Trima® apheresis machines 10 (available from the assignee of the present invention) are shown and described throughout; these are intended as exemplars only. As shown in FIG. 1B, connections can be made to numerous other machines as well, such as COBE® Spectra™ apheresis machines and/or Baxter, Inc. and Haemonetics Corporation apheresis machines (such as the CS-3000, the Amicus and the MCS+ apheresis machines, inter alia). The currently preferred machines 10 are, as shown, Trima® apheresis machines 10 (see e.g. FIGS. 1A–1D). However, a representation of a COBE® Spectra™ machine is also shown in FIG. 1B, identified therein generally by the reference numeral 10A, and a Baxter Amicus machine and a Haemonetics MCS+ machine are also shown in FIG. 1B and identified by the respective reference numerals 10B and 10C. Use with a more traditional manual whole blood collection system is also shown schematically in FIG. 1B, generally identified by the reference numeral 10D, therein. Thus, this system is intended to and will operate with various apheresis as well as whole blood collection systems.

Generally, a centralized computing/data storage assembly 140 may include, as shown schematically in FIG. 1A, a central station 148 which may include, for example, data input/entry devices generally identified by the reference numeral 149. Such devices 149 may, more particularly, include a keyboard 149A, a mouse 149B, and/or if desired, devices such as a barcode reader (not shown), and/or a digital camera (not shown) and/or an input/output display monitor and screen 200 as these may be known in the art. Various internal hardware and software elements, again as known in the art are also intended to be included within a central station 148. Further, the centralized computing/data storage assembly 148 may include a data manipulation device 144 (disposed within station 148 in FIG. 1A) which is preferably closely associated with and in some embodiments is perhaps inseparable from the central station 148. Manipulation device 144 may be an appropriate processor as used in a computer system such as may be used in a microcomputer or otherwise standard desktop or laptop personal computer (PC) including a preferably Windows®-based operating system and may further include other devices and attendant manipulation software (whether resident on/in the processor or resident in other associated memory devices but closely associated with the processor). A further preferred element of the computing/data storage assembly 140 is the storage medium 142 (not separately shown from central station 148 in FIG. 1A) used for data storage. The storage medium 142 may also be closely associated with the other elements of the assembly 140, i.e., the central station 148 and the manipulation device 144, or as with those other devices it may be dissociated in physical space but communicatively associated therewith through space (via cabling or energy wave communications, inter alia), so long as these elements cooperatively interact functionally. Hardware and software which may make possible data communication between various elements of assembly 140, as well as between assembly 140 and myriad possible external devices, some of which are like those shown in FIGS. 1A and 1B, are hereafter referred to as a communication or server subsystem 146. Subsystem 146 may also be mainly disposed on or in the assembly 140 and/or may be mostly physically disparate therefrom so long as it provides the data communication functions described herein.

Thus, the assembly 140 may be referred to as a whole for performance of the inputting and maintaining of donor-related data functions (principally through use of the central station 148, communication subsystem 146, and the storage medium 142), and also typically for the preparation of an initial procedure order (the process control parameters derived from the donor-related data and other considerations) for a given donor (through use primarily of the data manipulation device 144 together with the data obtained from either or both of the other elements 148, 142 as communicated by and through the subsystem 146).

Though perhaps not preferred, there may remain various situations in which it may be desirable to maintain the ability to perform data entry and/or manipulation procedures/functions at the corresponding pre-existing operator interface 199 of each particular apheresis machine assembly 10 as well. In such situations, a central computing/database assembly 140 may thus not be required for operation of assembly 10 even if still provided. Note in the preferred apheresis machines 10 shown in FIG. 1A (such as the Trima® machines 10 described above), the computing/database and data entry and manipulation capabilities are available in and would thus be able to continue to separately provide these functions, if desired. Moreover, this could still occur even when connected through a central communications system 146 to a central assembly 140 such that the computer/database assembly 140 may still collect/retrieve data from the one or more apheresis assemblies 10 even if the central assembly 140 is not used to program the respective machines 10. However, where a central computing/database assembly 140 is employed as preferred herein, this donor-related data and/or initial procedure order is preferably generated by the central computer/database assembly 140 and then transferred to one of the apheresis machines 10 (via an RS/232 or other similar interface, among other communications options such as energy wave communications, inter alia (see further descriptions below)). In either event, the operator is preferably provided with one or more data manipulation or optimization options, whether through the central data manipulation device 144 of a centralized computing/data storage assembly 140 or the data manipulation capabilities of the apheresis machines 10 themselves. Note the data manipulation and/or optimization options provided by a central assembly 140 may provide a different set of process control parameters than an initial procedure order that might result from data entered manually on the apheresis machine 10 because the data manipulation and/or optimization on a central assembly 140 may be based upon one or more previously specified and central database stored conditions/goals (e.g., input blood component yield, input procedure time) and one or more particular derivations for the process control parameters. Generally, more flexible options would be available from a central server system 140 than those previously available on discrete machines 10. Moreover, if an optimization option is selected at the central server 140, a manually-entered procedure order may be modified to reflect the results of such an optimization and the collection procedure may be initialized/reinitialized with the results of the optimization (i.e., the collection procedure could be reinitialized in the less preferred case of an optimization which is performed after the collection procedure has been started and such a case is referred to as a downstream optimization). The collection procedure may then thereafter be performed by the respective blood component collection device 10.

The concept of optimization here generally refers to achieving the maximum or best product output depending upon certain circumstances (e.g., obtaining the most product in a certain specified time or achieving a specific yield in the fastest time). On the other hand, the concept of data manipulation is more generally here intended to have a similar yet less exacting connotation, such that perhaps the best or maximum output may, but will not necessarily be the result. Thus, data manipulation is here intended to encompass optimization calculations in addition to providing perhaps less than optimum but still high efficiency results depending on certain further combinations of criteria. Thus, data manipulation is intended to generate more and/or perhaps better options to the blood donation center. For example, blood centers may prefer or determine to require certain combinations of products from certain blood type donors 14 (see FIG. 1B); then the blood center 1000 can prioritize this in the computer/database 140 so that those donors will donate those combinations even if the particular yields or donation times are not fully optimized according to the concept of optimization set forth above. Thus, yield or time optimization can be made secondary to other data requirements and/or manipulations. Note also that optimization and/or manipulation may be performed without requiring the central system 140 to collect/retrieve data from the various apheresis assemblies 10. Thus, communications may be made only one-way to (or from) the apheresis assemblies 10. Further, a preferred purpose for performing the optimization and/or manipulation functions centrally is to allow selection of the donation procedure prior to connection of a donor to a machine 10; thus, a particular product or products and the corresponding tubing set (if there are distinctive such sets) may be selected prior to machine set-up and donor connection. Also it could prove that the donor may not be able to provide a useful donation (for the end recipient/patient 15; see FIG. 1B), and this could thus be determined prior to machine set-up and/or donor connection.

Figure 1C:
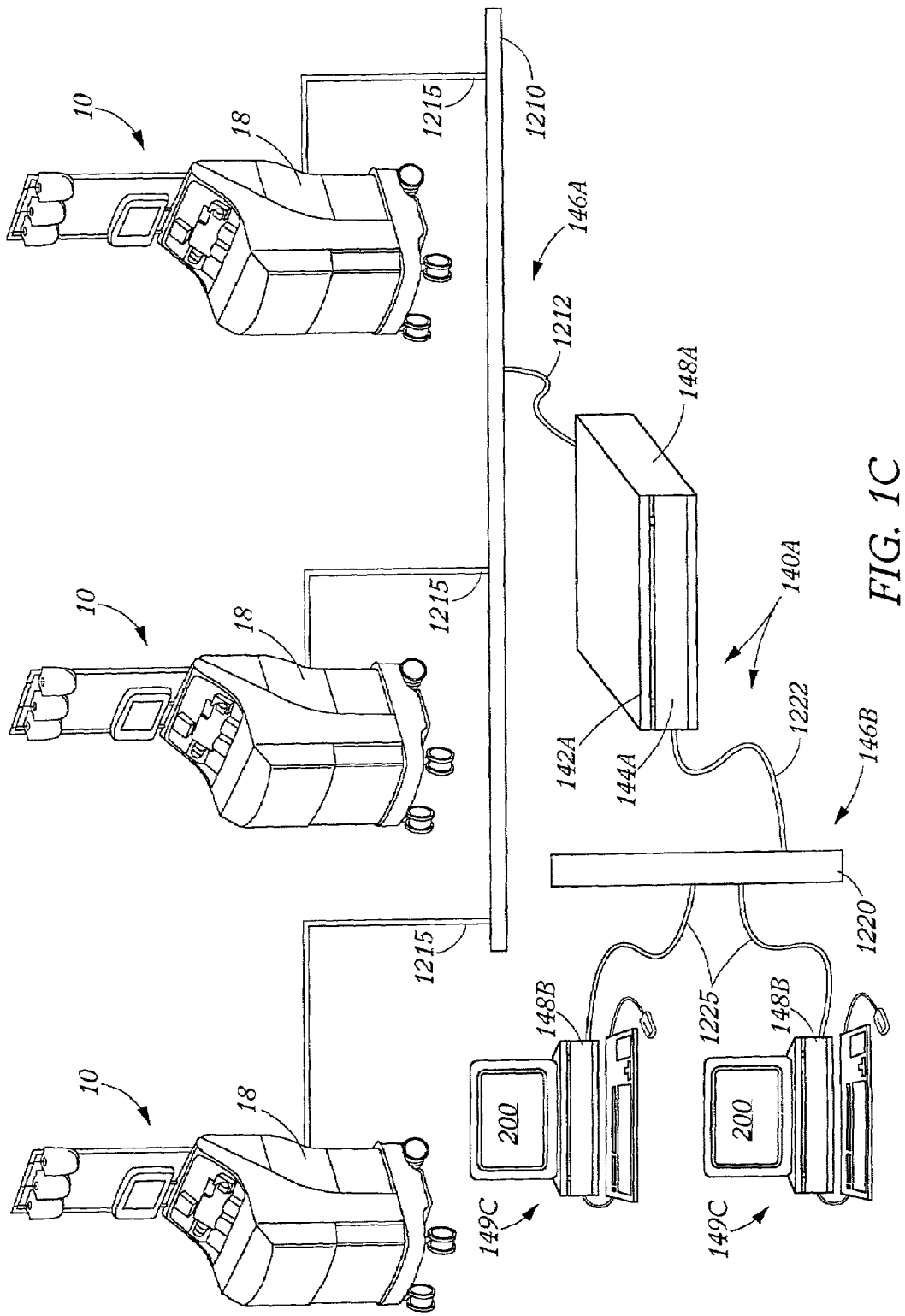
FIG. 1C is yet another schematic representation of a blood processing information management system in accordance with principles of the present invention.

Nevertheless, before describing the preferred manipulation/optimization processes of the present invention in any further detail (see description relative to FIGS. 7–10, below), two further, non-exhaustive alternative system embodiments will first be described. Referring first to FIG. 1C, an alternative centralized computing, communication and data storage assembly 140A is shown. Assembly 140A includes a central station, here referred to as a central data server 148A, which may be substantially like the central server 148 in FIG. 1A, at least preferably in primary function. At least a storage medium/database 142A and preferably also a data manipulation device 144A, each again substantially like those described relative to the embodiment of FIG. 1A are also preferably disposed within the central server 148A of FIG. 1C. However, in the embodiment of FIG. 1C, the communication sub-system identified generally by the respective reference numerals 146A and 146B, is shown as preferred here discrete therefrom, in two general sub-parts, referred to respectively as the machine network 146A and the client network 146B.

Machine network 146A preferably includes a network terminal server 1210 with a connection 1212 between the server 148A and the terminal server 1210. Respective connections 1215 are also shown as disposed between terminal server 1210 and each of the separation/collection machines 10. Connections 1212 and 1215 may typically be RS/232 cable-type connections, or other alternative data communication connections may be used including such options as radio, microwave or other electromagnetic wave communication systems (not specifically shown). Note that other separation/collection machines/systems, such as systems 10A, 10B, 10C and 10D (from FIG. 1B) may also be connected to/through the illustrated terminal server 1210 or a further discrete server (not shown).

A similar, though preferably discrete, network terminal server 1220 is also shown in FIG. 1C to illustrate a preferred communication sub-system for the client network 146B. A connection 1222 between the central server 148A and the terminal server 1220 is also shown, as are respective connections 1225 from the terminal server 1220 to one or more data input/output/ manipulation stations 149C (two shown here). Connections 1222 and 1225 may here also typically be RS/232 cable-type connections, or take other data communication forms including, for example, energy wave communication forms. Note also that other devices (not shown) might also be connected or connectable to/through the illustrated server 1220, as for example, one or more printers (not shown) or other accessory devices. Note, stations 149C may contain, as above, one or more various input/output devices such as keyboards, mice and/or screens (as shown) or otherwise (barcode readers, digital cameras, etc., not shown). Moreover, as decentralized stations, these assemblies may also generally include computing devices and/or capabilities such as may be included in standard desktop or laptop computers, including the stations 148B as shown, and potentially data storage/memory and/or data manipulation devices and/or software along with potential resident communications devices and/or software.

Separating the machine network server 146A from the terminal network server 146B allows for isolating and/or protecting communications therebetween, as may be desired. Thus, the respective servers may have on one side, a network connection to the central server 148A using discrete I/P (Internet Protocol) address information, and on the other side, RS/232-type connections to the respective end devices (machines 10, and/or input/output devices 149C, e.g.). In this fashion then, each network may be kept private from each other such that the I/P's are essentially hidden from each other by the central server 148A. A firewall communication protection setup as known in the art may thus be established.

A further alternative communication sub-system 146C is shown in FIG. 1D. Sub-system 146C generally includes a network terminal server 1230 with respective connections 1232 which connect respective central servers 148C to network terminal server 1230. RS/232 or other communication connections (as above) may be used here as well. In this way, two or more centralized servers 148C may communicate data with each other. Thus, central servers in two or more physically separate clinics may communicate with each other. Such a system may also be used for communication with other information systems (blood center information systems or hospital information systems) such as is schematically shown in FIG. 1B. Other similar communications can also be made in this way, as for example to help or maintenance centers (not shown), as described below. Firewall types of communication protections may also be set up here, such as was described above. Thus, network connections can be made between each central server 148C and the network terminal server 1230; whereas RS/232-type communications can be established elsewhere. Note, all variations of system 140 may include communications connection(s) of many different sorts which allow each particular device to communicate with other devices. RS/232 communications connection(s) as described, are only examples of such communication media. Communication media may typically embody, be embodied in or otherwise be capable of interacting with and/or through computer readable instructions, data structures, program modules or other data in a modulated data signal such as a carrier wave or other transport mechanism and include any information delivery media. The term modulated data signal may include a signal that has one or more of its characteristics set or changed in such a manner as to encode information in the signal. By way of example, and not limitation, communication media may include wired media such as a wired network or direct-wired connection, and wireless media such as acoustic, RF, infrared and other wireless media. The term computer readable media as used herein preferably includes both storage media and communication media.

Figure 2A:
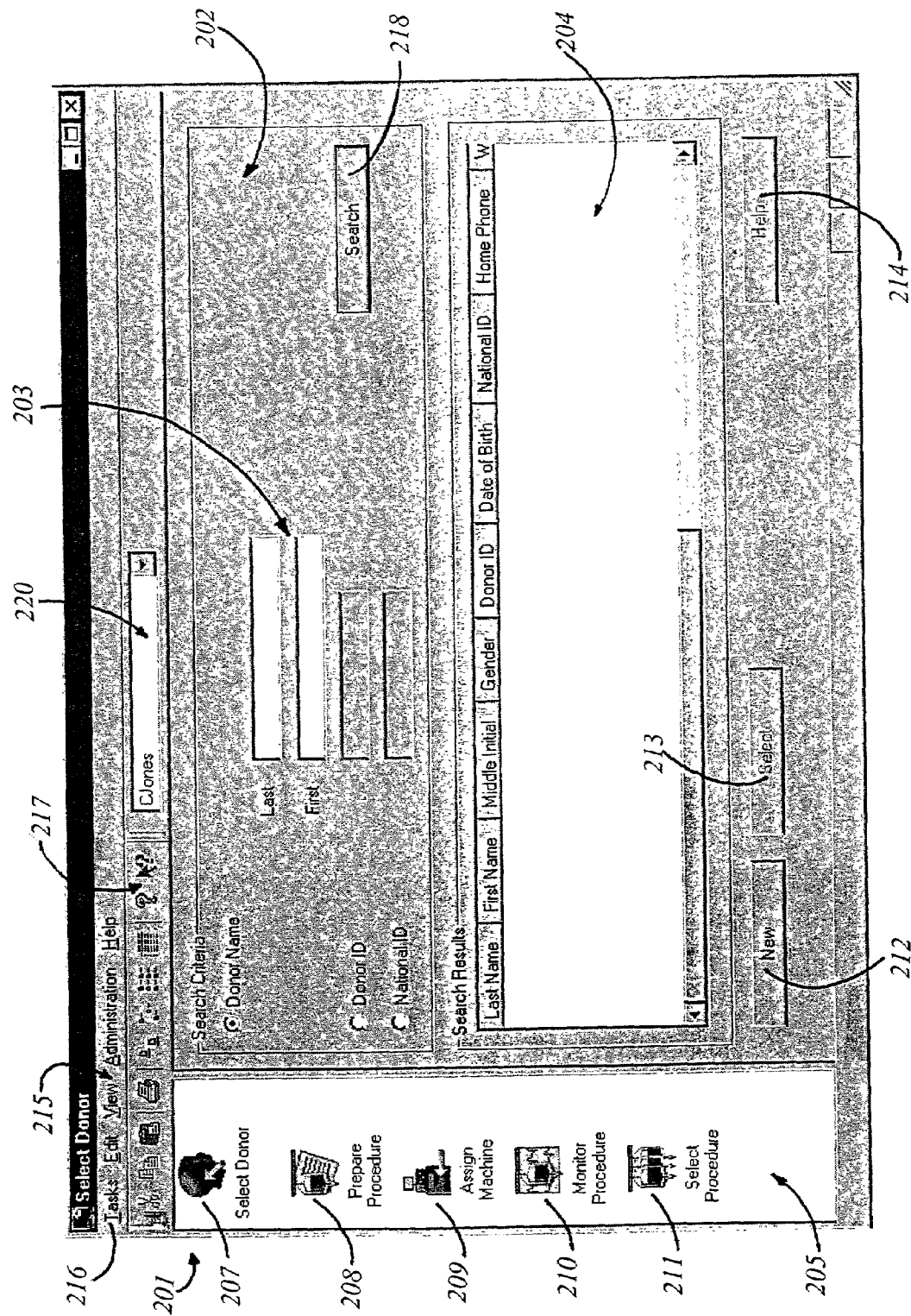
Figure 2B:
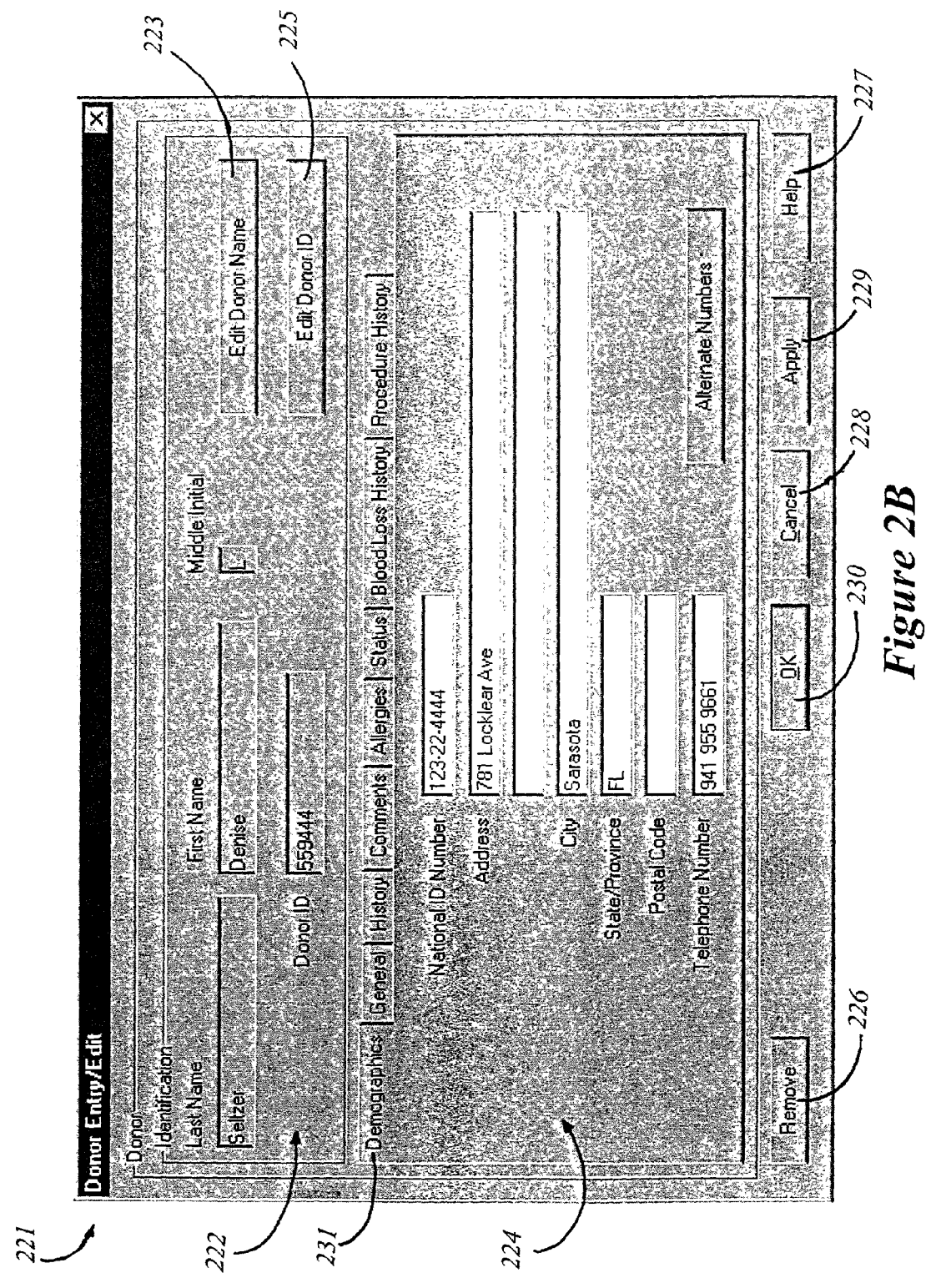
Figure 2C:
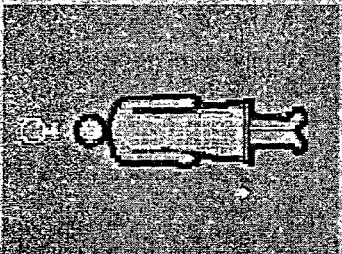
Figure 2D:
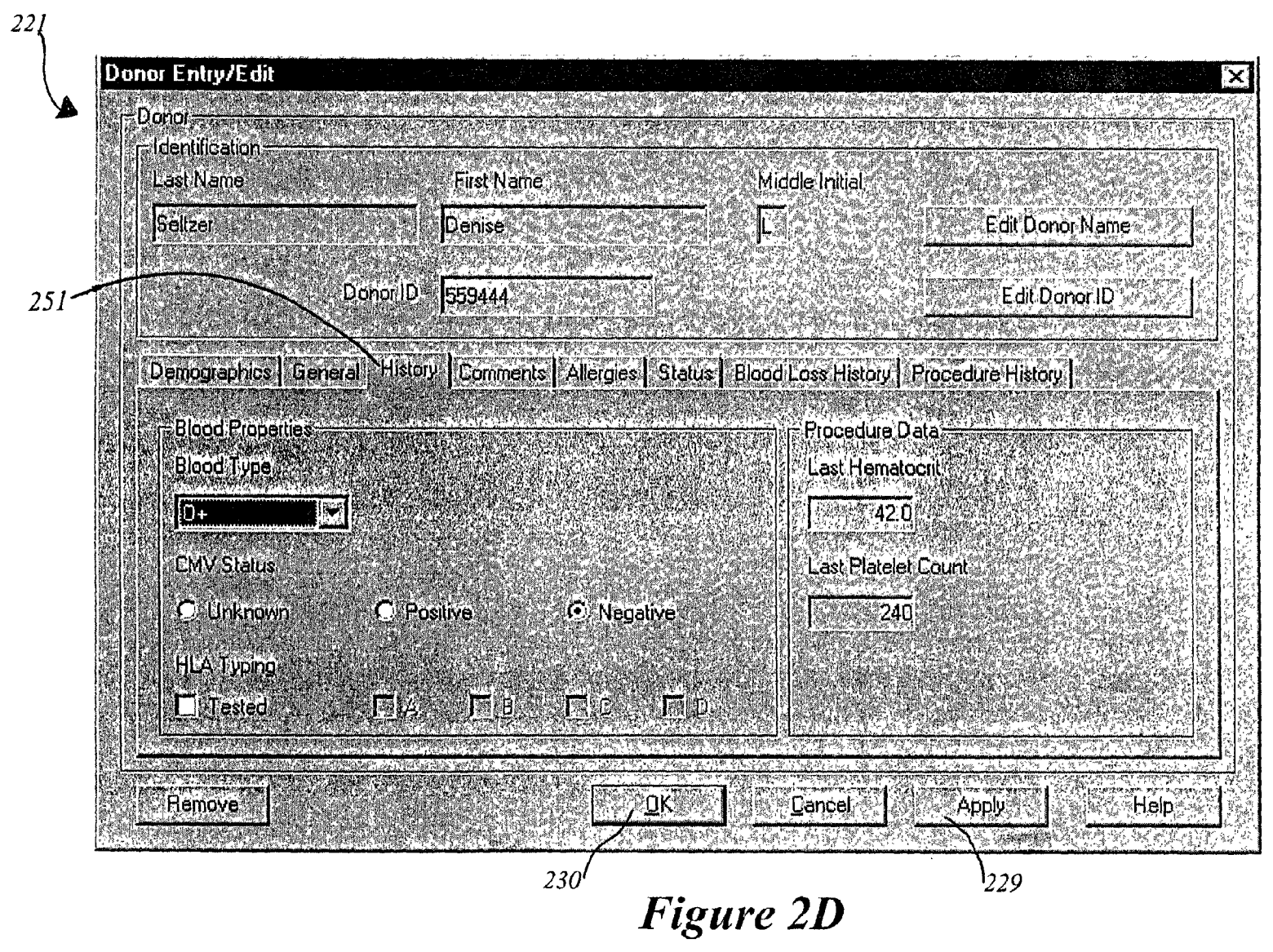
Figure 2E:
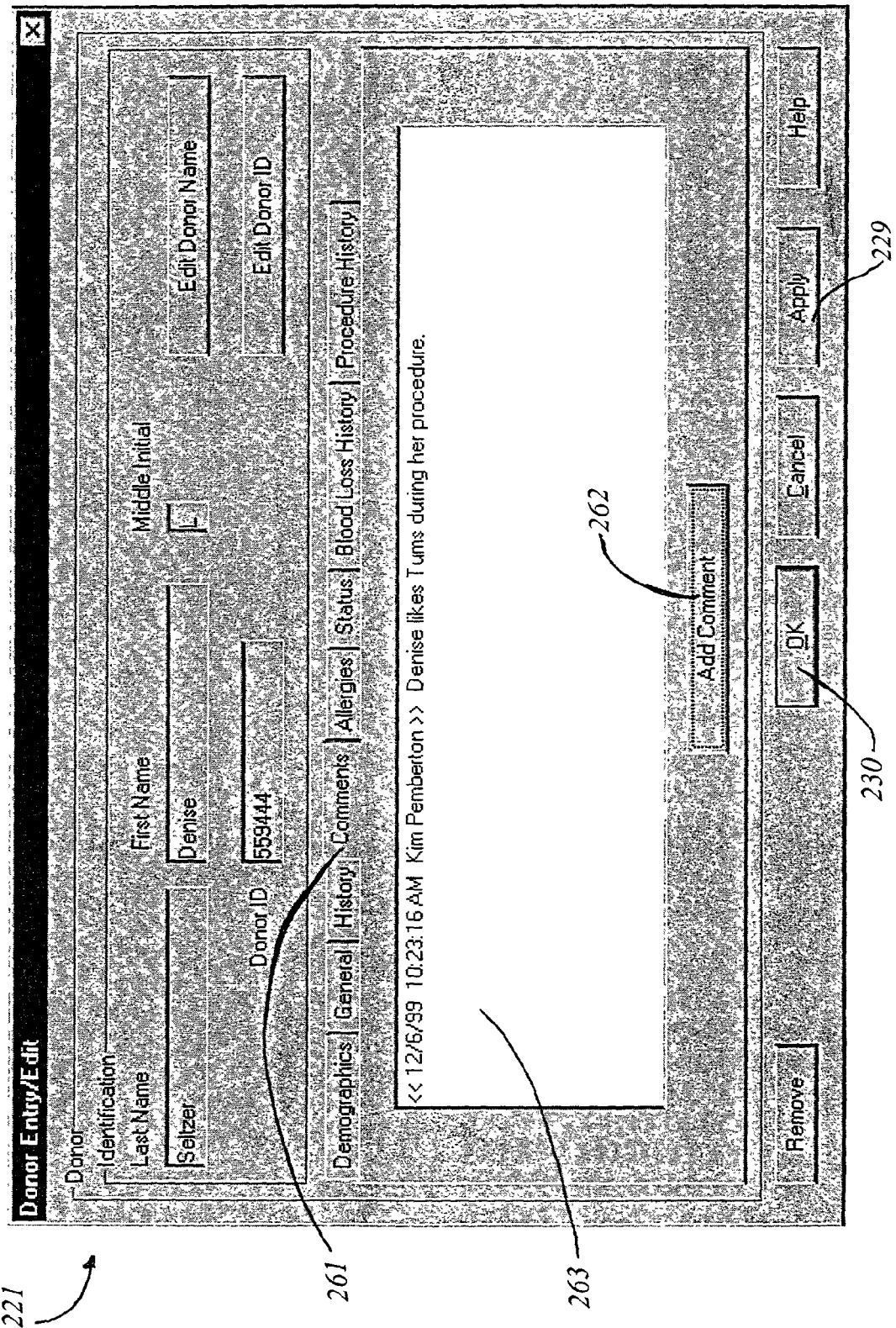

A more detailed description of the preferred steps for using the present preferred system will now be set forth. In FIGS. 2A–2I, inter alia; use of the centralized computing/data retrieval assembly is shown in more detail. First, FIG. 2A depicts an exemplary display page or screen 201 which may be the first such screen displayed on the output monitor display screen 200 (see, e.g. FIG. 1A) of the centralized computing/data storage assembly or system 140 when the software thereof is initially accessed. A more, rather blank, screen (not shown) may be used as an initial screen upon startup, as described below. As can be seen in display screen 201 generally, the initial donor information may be gathered here, such as for example the donor's name (last and/or first), and/or the donor's identification (ID) number or like identifier (if used), and/or the donor's telephone number or other identification data (also if used, not shown). Data entry fields for these types of data may be seen in the main work area 202. These are several examples of possible initial identifiers among numerous others which could be alternatively substituted herein.

Moreover, as mentioned this could be the first display screen to be shown upon software initialization, or other alternatives (not shown) could be simply used preliminarily hereto by way of introduction to this or a like display 201. In any event, some display is preferably used as the starting point for data entry (and/or search, if the data were previously entered or imported from another system) for use with a particular donor, and for the sake of convention, display 201 will be used in this role for this description of the preferred embodiment. Note also, that as shown in FIG. 2A, disposed next to the main work area 202 (with sub-areas 203 and 204 as will be described below) is a procedure icon selection area 205 which is depicted along a vertical portion of the left-hand side of display 201. In it, five icons 207, 208, 209, 210, and 211 are currently shown, though either more or fewer such icons could be used as may be desired.

A description of the preferred general overall procedural flow will be set forth starting with particular reference to the procedure icon bar 205 on the left side of the display screen 201.

As an initial step or sub-procedure, the Select Donor icon 207 represents the performance of several functions generally described as follows. First is a Greet Donor function wherein the system operator may verify and/or add a new donor record to the system database 142, and check-in a donor into the system 140 (either by data entry directly into this application or via automatic transfer of data from a discrete blood bank information system). Thus, the operator may perform Donor Entry/Edit functions to enter or modify a donor record in the database (see e.g., FIGS. 2B–2I, as described below). This may also include capturing a donor image using a digital camera to take the donor's photo (this functionality may also or alternatively be part of the Prepare Procedure Wizard process; see below). And, this may include use of a barcode reader to enter barcoded data such as the donor ID, etc. (Note: this data input functionality may also be part of other processes in this system such as the Prepare Procedure Wizard (entering barcoded unit number) and/or the Finalize Procedure Record (entering barcoded lot number/data for supplies).)

Figure 3A:
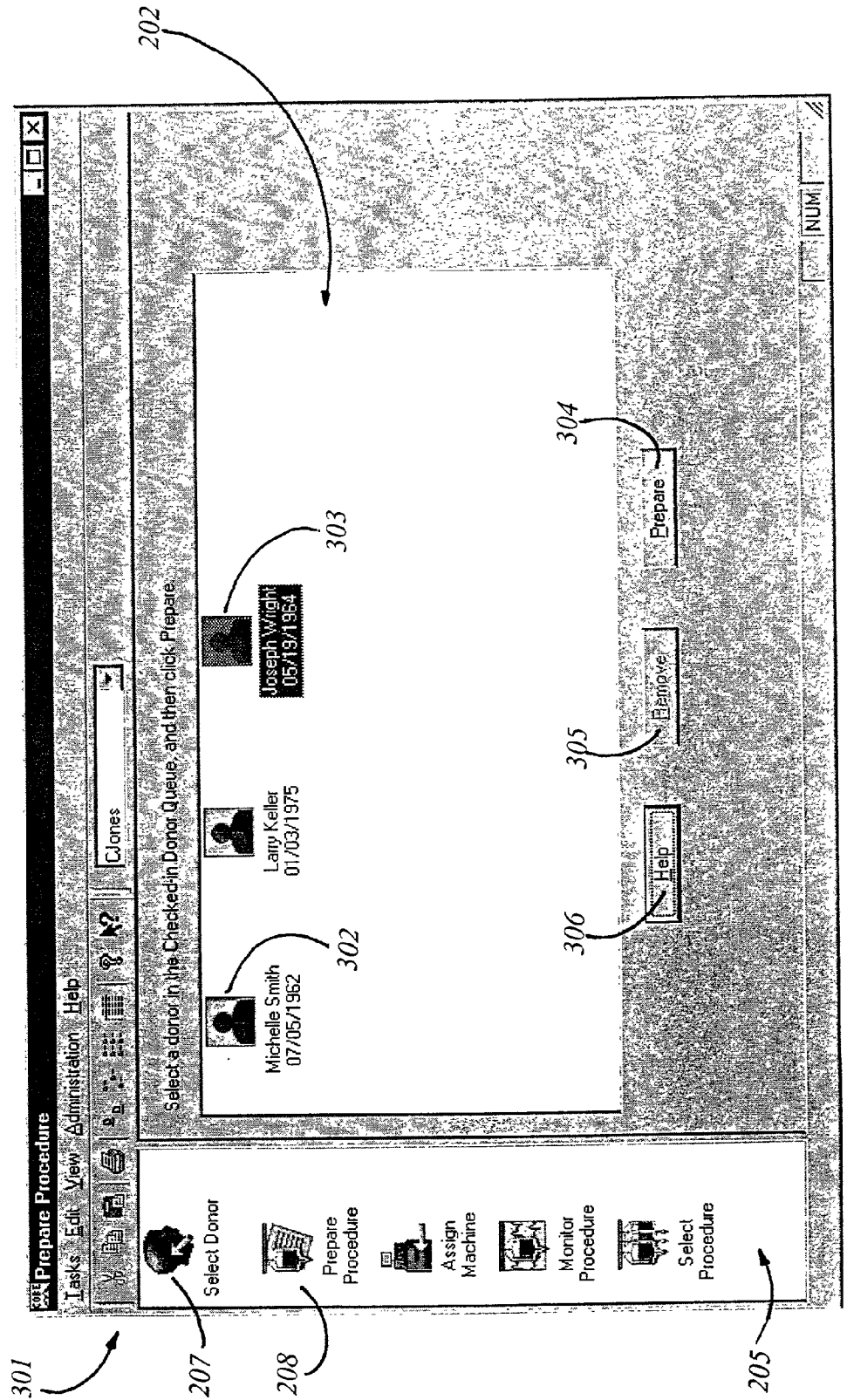
FIGS. 3A–3F are further display screen depictions of data entry, retrieval and/or manipulation display pages for use in accordance with the present invention.

After the data entry/verification, the next general step would preferably be to Prepare the Procedure for component collection as indicated by the second icon 208 in bar 205 as shown in FIGS. 2A and 3A, inter alia. This preferably involves using a Prepare Procedure sub-procedure or software wizard to record further donor information and select the procedure to be run on the donor prepared as set forth above (see description relative to FIGS. 3A–3F, below).

Next, the operator preferably uses the Assign Machine icon 209 to access the sub-procedure for assigning the donor to a particular apheresis collection system 10. More details of this process are described below with particular respect to FIGS. 4A and 4B.

Figure 5A:
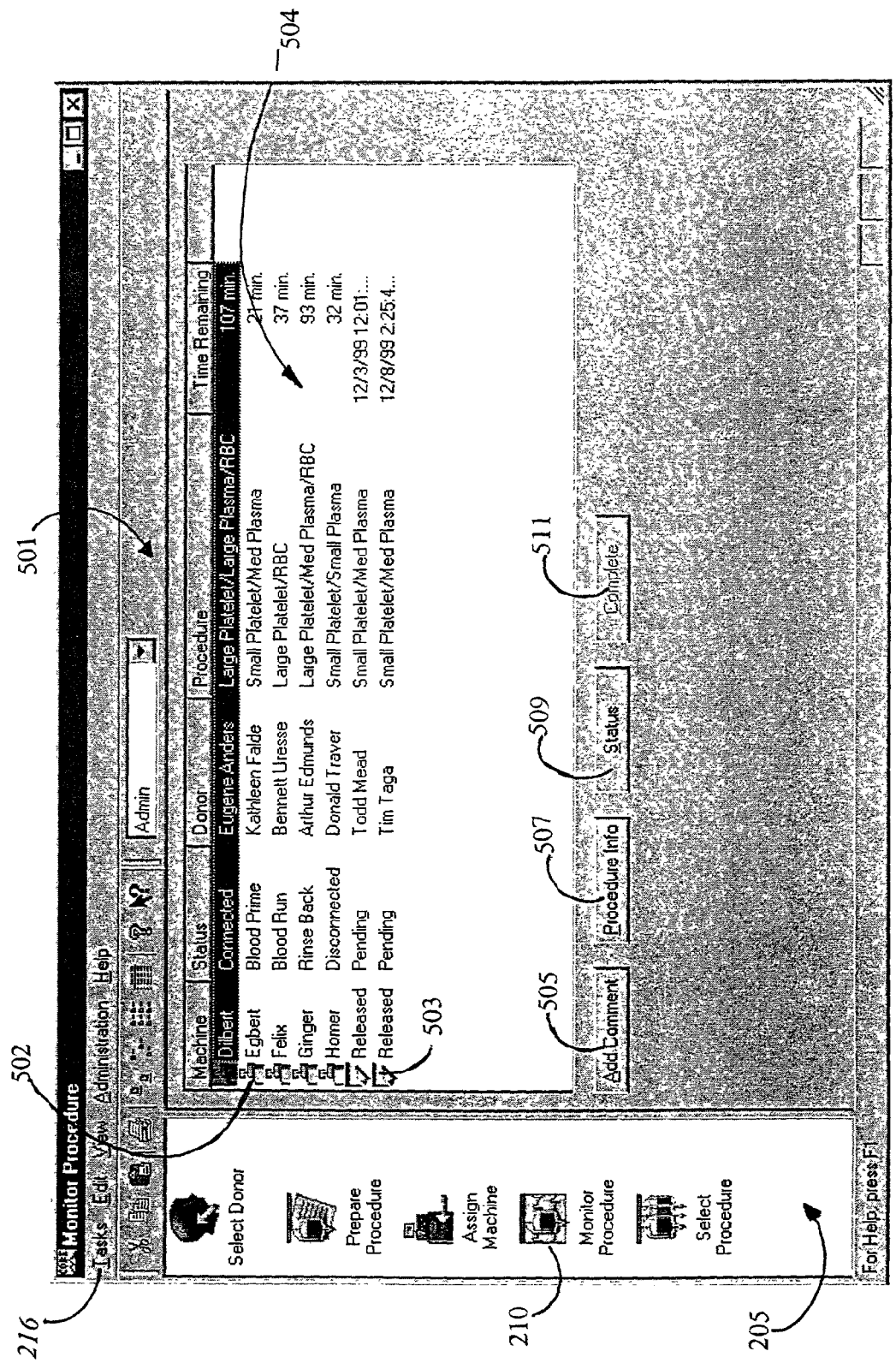
FIGS. 5A and 5B are yet still further display screen depictions of data entry, retrieval and/or manipulation display pages for use in accordance with the present invention.

As shown generally in FIG. 5A, the central system 140 may be used for monitoring the procedure/machine status after the assignment of a donor to a particular machine. An icon 210 (FIGS. 2A and 5A) is preferably included for accessing this functionality in the left-hand procedure icon area 205. Screen 501 (FIG. 5A) reflects the first step in such a monitoring sub-procedure. Finalization of the Procedure Record may also be performed here, wherein the operator may enter procedure data, including operator roles and supplies entries. (Note: this record finalization functionality may also be part of the Select Procedure process below.)

Figure 6A:
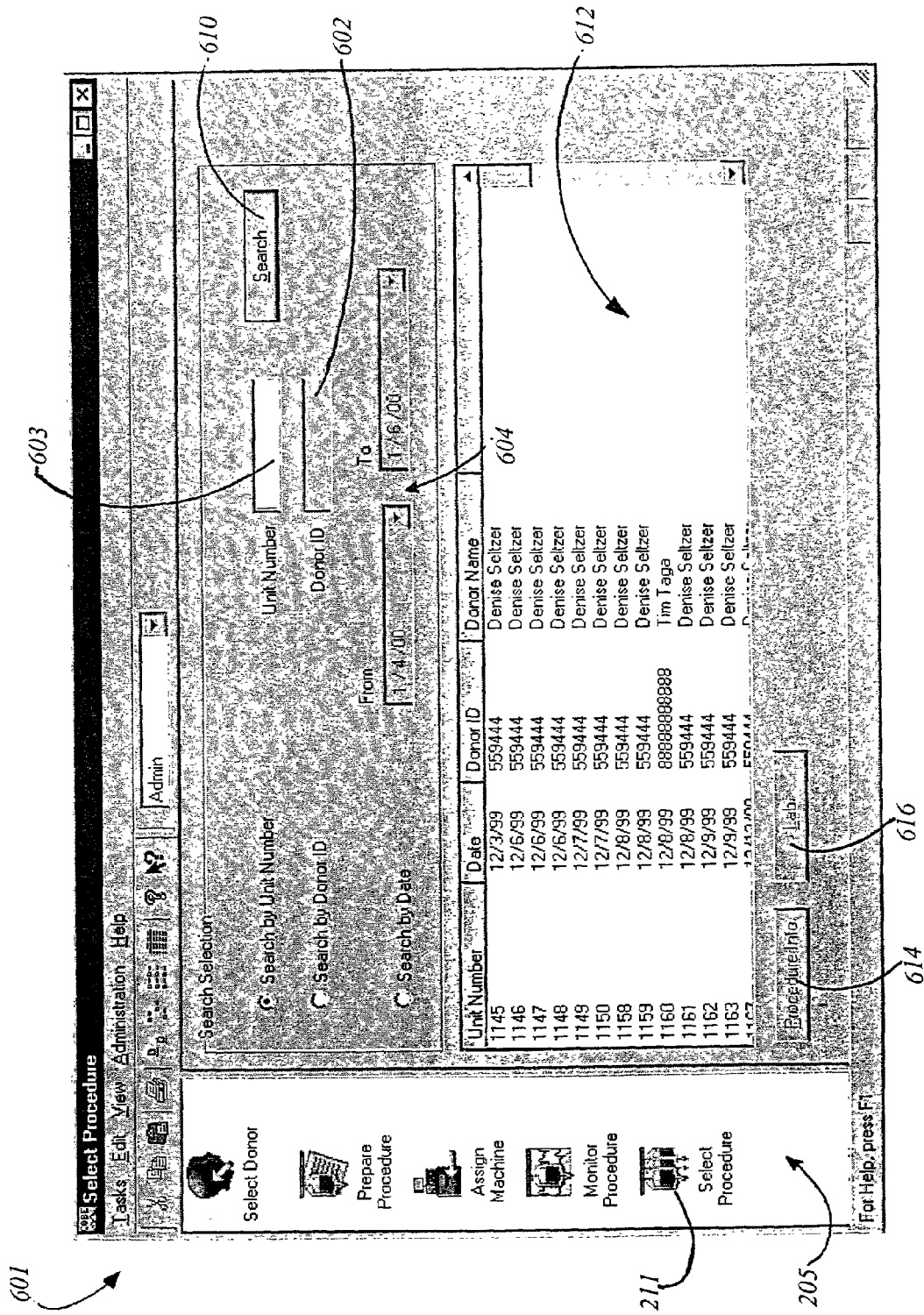

Another optional step in the overall procedure shown in FIGS. 2A and 6A by the icon 211 is the Select Procedure sub-procedure where the operator may search for and select a procedure (either active, pending, or finalized). A screen 601 such as shown in FIG. 6A may then be displayed (as described in further detail below). The operator will then be able to enter lab results by entering procedure product volume/quality information returned from the lab. The operator may finally prepare a Report on the Procedure by generating procedure or donor or production reports.

It ought to be noted that the various sub-procedures identified by the respective icons 207–211 can be selected at any time in the overall procedure to view, input or modify particular desired information. As an example, but not to be considered in any way as a limitation, the assign machine icon 209 could be selected at anytime to view the list of available and/or assigned machines 10. However, it should be noted that certain functionalities may thus be unavailable if an icon 207–211 is selected without having completed a previous sub-procedure. For example, upon selection of the assign machine icon 209 as suggested here, the assignment function will not be available unless at least one donor has been processed though the Prepare Procedure sub-procedure (see description, below). In such a case, where no donor has yet been so processed, there would not appear any donor icon in the donor assignment queue of screen 401 (FIG. 4A), even if the available and assigned machines 10 may be shown in the machine list. Similar functionalities preferably requiring pre-completed sub-procedures (thus building on previous module completion(s)) are identified throughout the below descriptions.

Although not a part of the general run procedure (and thus not involving or resulting from the clicking of icons in the procedure icon area 205), Administration Tasks (extra security being preferably required to access these options) may generally include: Setting Up the Application including setting default values; setting the apheresis machine configuration(s) including creating and/or modifying apheresis collection system configurations; Defining Products including establishing an unlimited number of product definitions; Defining Procedures including establishing an unlimited number of procedure definitions (combinations of product definitions); Defining Focus Lists including establishing an unlimited number of procedure focus lists (prioritization of procedure definitions); Performing Database Administration including managing and maintaining the data stored within the central database; and Blood Product Prediction wherein a blood product forecasting report may be generated.

Returning now to FIG. 2A, a more detailed description of the preferred overall procedure will now be set forth. In an initial start-up mode of software initialization, the main work area 202 could be adapted to display a preliminary display screen (not shown) which has no active work spaces. Then, after log-in (see below), the operator could be forced to select an icon from a menu list and/or from the left-hand procedure icon selection area or bar 205 in order to initialize the overall procedure. As an example, the operator could first select the select donor icon 207 with a computer screen cursor or pointer (not shown) and click the enter or mouse button (neither shown) as is known in the art of standard desktop or laptop computer, Windows®-based or like software applications. This selection could then bring up the shown display 201 for beginning a donor check-in procedure. A few further alternatives for use in start-up (as well as throughout operation) may be found in the toolbars located as shown horizontally along the upper portion of the display 201. These are toolbars much like those used in a plurality of computer Windows®-type software applications with numerous functional similarities and specific distinctions as described herein. For example, the software start-up to the initial working display may also be achieved by selecting the "Tasks" menu heading 216 in the top level menu toolbar 215 and then selecting the appropriate "open" file command (not shown) or other like commands as are generally known in the art. Or, similarly, a small icon toolbar 217 may be configured to be used for initiating software procedures, as may also be generally known in the art. Other menu headings and/or icons (not shown) in toolbars 215 and/or 217 (or otherwise, not shown) may be used for other functions in startup or otherwise.

A third toolbar 220 may further be used in or even prior to software initialization or it may not be opened until the main work area 202 has been opened. The third toolbar 220 as shown and preferred herein has a location for the typing of a name or other identifier which may be used to begin the process of either data entry for new records or a search for existing records. This third toolbar 220 is preferably used for identifying the operator of the system, such identification being useful for logging-in and/or assessing the operator's level of security clearance, inter alia (described below). Thus, it is preferred that this operation of logging-in the operator be completed first. Further, it is preferred that a system administrator have previously established authorized users, with log-in names and optional passwords. The log-in names may then be typed in the blank space in tool bar 220, or the down arrow may be selected and clicked to reveal the list of authorized users to be selected. Once a user log-in name is entered, then a pop-up dialog box/window (not shown) may be made to appear to prompt entry of an appropriate password. Note, password and/or user log-in names may be made editable via such a pop-up dialog box/window (not shown) or may be restricted to editing by a system administrator. Further similar options may also be used for these initialization procedures as may be known in Windows® or Windows®-like environments.

Returning now to the main work area 202 of the display screen 201, two sub-areas 203 and 204 are shown in which data may be entered or displayed. First, as shown in sub-area 203, data concerning the identity of the donor to be checked-in may be entered in order to begin the donation process. The computer/database system 140 may then be made to search its database 142 (by selection of the search button 218 by the operator) to determine whether this particular donor has been previously entered in the system. If so, the system 140 returns the results of that search in the search results sub-area 204. Note that the search may be made dependent on any of the criteria set forth in the first sub-area 203 (or others not shown herein but alternatively usable herewith). Also, the search mechanism may be adapted to search wild cards and/or truncated terms or list various short forms for further search as these and other search capabilities are known in the art. As such, when typed into the proper field, this display screen simply calls up a donor from the existing database if such a donor exists therein. A search/query format may be used wherein typing an alphabetical initial will call up into the results window 204 all donor names beginning with that initial. The operator may then double click on a listed name to select and call up the next preferred screen (see FIG. 2B, the donor entry/edit screen 221), which contains greater detailed donor information as will be described below.

First, however, several other graphical buttons are shown in the main work area 202 of FIG. 2A and may be used to perform various functions. For example, below the work sub-area 204 are examples of three buttons which could be set forth on this or any other alternative display screen used herein. In this example, the three buttons here are the "new" button 212, the "select" button 213 and the "help" button 214. The "new" button 212 could be used to toggle to a fresh search page like this one 201 shown without any information in any of the fields (name, ID, or results). Alternatively, the "new" button 212 could allow for either new data entry editing directly in the fields shown here in screen 201, or could be used to call up a secondary display screen, such as the Donor Entry/Edit screen 221 shown in FIG. 2B (described below). Such a "new" screen would preferably have empty fields to allow for new donor information data entry. Note, the "new" button 212 is shown in active, darkened mode in FIG. 2A as compared to the other "grayed-out" buttons 213 and 214. This means it is active as shown (and as would be understood to those knowledgeable in the art of common, conventional Windows® and the like software applications). It is active as shown when it may be desirable to enter new data records into the system. The "grayed-out" "select" button 213, on the other hand, is inactive until a search result record is displayed in sub-area 204. When such a record is made available, button 213 would be made active and darken in style such as the other active buttons shown here. The "select" button 213 provides for the selection of a donor data record to be verified and/or modified for preparation of a collection procedure. This functionality as well as that of the "help" button 214 is described in greater detail below.

As next shown by the donor data entry/edit screen 221 in FIG. 2B, data can be either manually input into the computer/database system 140 by typing into the corresponding fields such as will be described further below. Or, any appropriate data input can be performed with an alternative input system such as, for example, a bar code reader (not shown), or input from other computerized information systems as will be described below and/or become obvious to those skilled in the art. If using a bar code reader, a donor may be given a donor identification (ID) card which may have a bar code imprinted thereon which represents that particular donor's data. Then, an optical reader (not shown) can be used by the operator to read the bar code information from the card to fill in the donor data fields shown in FIGS. 2B–2I. The other previously introduced alternative input process would be in taking advantage of other pre-existing database/information systems which may already contain the appropriate donor data. Thus, the present computer/database system 140 may be disposed in data communication relationship with one or more such pre-existing systems and simply upload the desired data therefrom. Thus, the fields such as those shown in FIG. 2B, et al., can be automatically populated from the blood center's management information system (e.g., Wyndgate, MAK, etc.). In this situation, the reception portion of the data entry process (i.e., initial data entry and/or verification) could take place entirely on the blood center receptionist's computer in the corresponding Wyndgate or MAK (or like) system. This information may then be retrieved by and/or forwarded to the computer/database system 140 to populate the fields such as those shown in the display 221 of FIG. 2B. This display 221 may be referred to hereafter as the Donor Entry/Edit screen 221 and may, in the three-room model, initially be called up in the what may be referred to as the "Reception" room. This three room model will now be briefly described.

There may be considered three main data input/verification points in a collection process. At the first point, hereafter referred to as "Reception," the donor is checked into the overall process. Under a scenario of data connectivity between the central computing/database system 140 and a blood bank information system, the "Reception" room/step may be handled through the blood bank information system and the needed donor data may then be automatically transmitted (downloaded or uploaded or otherwise) into the central system 140 as described above. With this connectivity between the blood center information system and the central system 140, the historical donor data (which may be batch file loaded into the central system 140 periodically) may also be called up and the donor may then be assigned to the second room, hereinafter also called the "Screening Room." In the screening room the donor information may be retrieved and displayed and several preferable pieces of lab data may be input for purposes of selecting the proper/preferred collection procedure to be performed. A donation unit number may also be assigned at this point. The central system 140 may, but preferably does not, hold confidential donor information influencing potential deferral; this information would preferably reside only in the blood bank information system. The central system 140 is preferably only concerned with the collection process. In either the "screening room" or the third room, hereinafter also called the "Donation Room," the donor may be assigned to a particular apheresis machine. The procedures performed in the donation room may also include recording other data about the procedure such as recording the identification numbers associated with the disposable tubing set. Once the donor is assigned to a machine, the central system 140 would preferably go into a monitor-only mode relative to that donor and that machine for monitoring and/or recording any and/or all events in the procedure. More details hereon are provided below.

Returning to the donor entry/edit screen 221 of FIG. 2B, further details concerning some of the specific, preferred fields, tabs, buttons, etc. shown on screen 221 in FIG. 2B will now be set forth.

As mentioned, new donor records may be created using screen 221, and pre-existing records may also be edited/modified here. A primary difference in creating new records versus modifying existing ones lies in the fact that the fields shown in FIG. 2B will be empty prior to entry of new record information, as opposed to having been populated by previously entered (or imported) data in the modification sense. As shown in FIG. 2B, the data fields are primarily populated thus generally signifying either a data import or previous donor record entry situation.

Primarily donor identification data/information, such as the donor's name and/or ID, may be entered/edited in the fields disposed preferably in an upper substantially fixed area 222 of screen 221. However, if this data has come from a previously entered record, the fields in area 222 are preferably "inactive" as shown by being "grayed-out." Thus, these fields would preferably not be editable directly, rather would be editable otherwise as described below. Other information about a particular donor may then be entered/edited in corresponding fields appearing with respective tabs in the lower data area 224. For example, donor demographics information may be entered/edited in corresponding fields under the "Demographics" tab 231 as shown in FIG. 2B. Other general information such as gender or date of birth, inter alia, would preferably be enterable/editable under the "General" tab 241 (see FIG. 2C). Blood type, CMV, (cytomegalovirus) and HLA (Human Leukocyte Antigen) type, inter alia could be entered/edited under the "History" tab 251 (FIG. 2D). A "Comments" tab 261 (FIG. 2E) could be selected and used for entry of comments about the donor. Allergy information could be entered or edited under an "Allergies" tab 271 (see FIG. 2F). Donor status data could be entered and/or edited under a "Status" tab 281 (FIG. 2G) including such data as, for example, last procedure date, numbers of donations given, over what period of time, etc. Other tabs, such as a "Blood Loss History" tab 291 (FIG. 2H) and/or a "Procedure History" tab 299 (FIG. 2I) could also be used for separate entry of such information. Note, separate pop-up dialog boxes or other alternative screen styles or types (none shown) may be used for prompting for and entering/editing these types of information.

Note, the information shown and described here in screen 221 may alternatively be optional or mandatory, depending on the desires of the ultimate user; here, usually a blood center. That is, the standard operating procedures (SOP's) of the blood center may be implemented herein to make certain information optional or mandatory, as desired. However, certain information, whether listed here (under the Donor Entry/Edit screen 221) or entered elsewhere (see the Prepare Procedure functionality, described below) may be required by the blood separation/collection assembly 10 prior to initiation and/or completion of a separation/collection procedure. Examples of such information may be gender, height, weight, blood type, and/or pre-count (platelets and/or hematocrit) information (again, see the Prepare Procedure, below). As such, some of this information (e.g., height/weight) would only be enterable/editable, as preferred here, in the procedure preparation portion of the overall process (see below).

Moreover, as introduced above, all, most, or at least the information required by the blood center may be entered or have been entered previously into the blood center's separate (but communicatively-linked) information system (not separately shown, but see FIG. 1B). Such an information system is separate from the present invention, although these systems may be made to communicate with each other. Thus, such information may be entered into the blood center information system, preferably according to the standard operating procedures (SOP's) of the blood center, and then this information may be transferred (downloaded or uploaded, or otherwise) to the central system 140 of the present invention. This information would then populate the respective fields shown and/or described here relative to the Donor Entry/Edit screen 221. An operator of the present system may then use screen 221 to merely verify the accuracy and/or completeness of this information shown on screen 221 prior to checking-in the donor for the present collection procedure.

In a presently preferred embodiment, when a blood center information system is used, the transmission of this general sort of donor identification, demographics and commentary information, inter alia, is one-way from the blood center information system to the central server system 140 of the present invention, primarily to maintain SOP's on which types of donor information a blood center may wish to capture. Thus, the operator may continue to operate at reception in a fashion unchanged from before introduction of the present invention.

Nevertheless, these donor identification data may also be transmitted both ways; namely, from the blood center information system to the central server 140 and/or back to the blood center information system from the central server 140. In such an option, these data may be entered/edited in either system and then be made to update the records of the other system. Note, these donor data communications are discussed here only in terms of the general donor data; not necessarily including feedback information about the results of any particular collection procedure. Such procedural data communications are also considered within the present invention, but are discussed further below.

First however, more particular descriptions of the preferred data to be entered/edited in screen 221 will now be described.

As mentioned, in the Demographics tab 231, the operator may enter/modify the donor's national ID, address and telephone number as shown in FIG. 2B. Then, after selecting the General tab 241, the following information may preferably be entered/edited: Gender (Male or Female, neither of which preferably selected by default); Date of Birth (which can be typed in text box or selected using pop-up calendar); Ethnic Background (preferably available via a drop-down list which is editable by selection only, and is preferably created by the System Administrator); and Donor Picture (the default is preferably a generic, genderless icon; however, if a gender is selected using one of the Gender radio buttons, this icon preferably changes to a gender-specific icon the next time the donor record is accessed, provided the operator saved the data before closing the dialog box). The operator can optionally click Update Picture to take donor's photo using an optionally attached digital camera.

The operator may then optionally click the Donor History tab 251 (FIG. 2D) to view/modify procedure history data for this donor. This tab 251 may contain the following information: Blood Type, CMV, HLA, Hematocrit, and/or Platelet Count. More specifically, the Blood Type may include A+, A−, B+, B−, AB+, AB−, O+, O−, or Unknown; preferably accessible via a drop-down list, editable by selection only; default is preferably Unknown. The CMV Status includes Unknown, Positive, and Negative Radio buttons options; the default is preferably Unknown. HLA Typing options are as follows: the operator may select the HLA Tested check box if HLA testing has been done for this donor; or left unchecked by default. And the A, B, C, D check boxes are disabled unless the HLA Tested check box is selected. Once HLA Tested is selected, the operator can select one or more HLA-type check boxes (A, B, C, and/or D). The Last Hematocrit and the Last Platelet Count are preferably non-editable, generally pre-populated fields from past procedure data or external blood bank information system, if available.

The operator may then also optionally click the Comments tab 261 (FIG. 2E) to enter/view free-form comments about the donor. To add a comment, the operator clicks the Add Comment button 262. A separate Enter Donor Comment pop-up dialog box (not shown) may then appear, or comments may be made enterable/editable within the work space 263, shown. The operator may then enter a comment in the text box. Note that a comment is preferably not saved in the donor record until the operator clicks the Apply or OK button 229 or 230 in the Donor Entry/Edit dialog box 221 (see more details below).

The operator may then optionally click the Allergies tab 271 (FIG. 2F) to enter/view donor allergies and associated comments. To view the comments about a specific allergy, the operator clicks the allergy in the Donor Allergies list; associated comments for this allergy appear in a Donor Allergy Comment box. To add an allergy, the operator may click the Add Allergy button. An Enter Donor Allergy pop-up dialog box (not shown) may then appear. A listing of allergies (preferably non-editable and created by the System Administrator) may be made to appear in such a dialog box and the operator may optionally enter a comment pertaining to that allergy in the Allergy Comment box. Note that an allergy is preferably not saved in the donor record until the operator clicks the Apply or OK button 229 or 230 in the Donor Entry/Edit dialog box 221 (see details below).

Figure 2F:
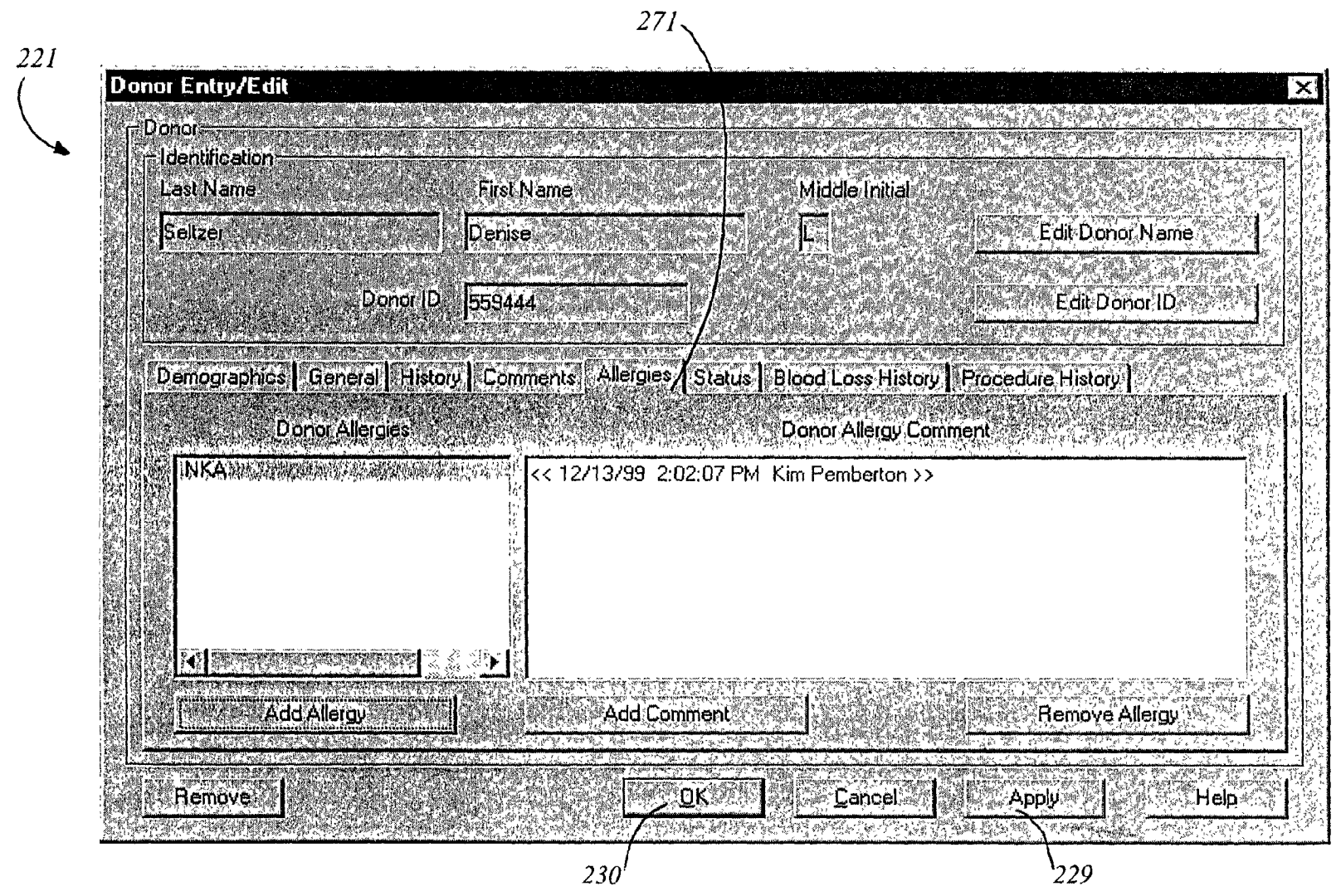
Figure 2G:
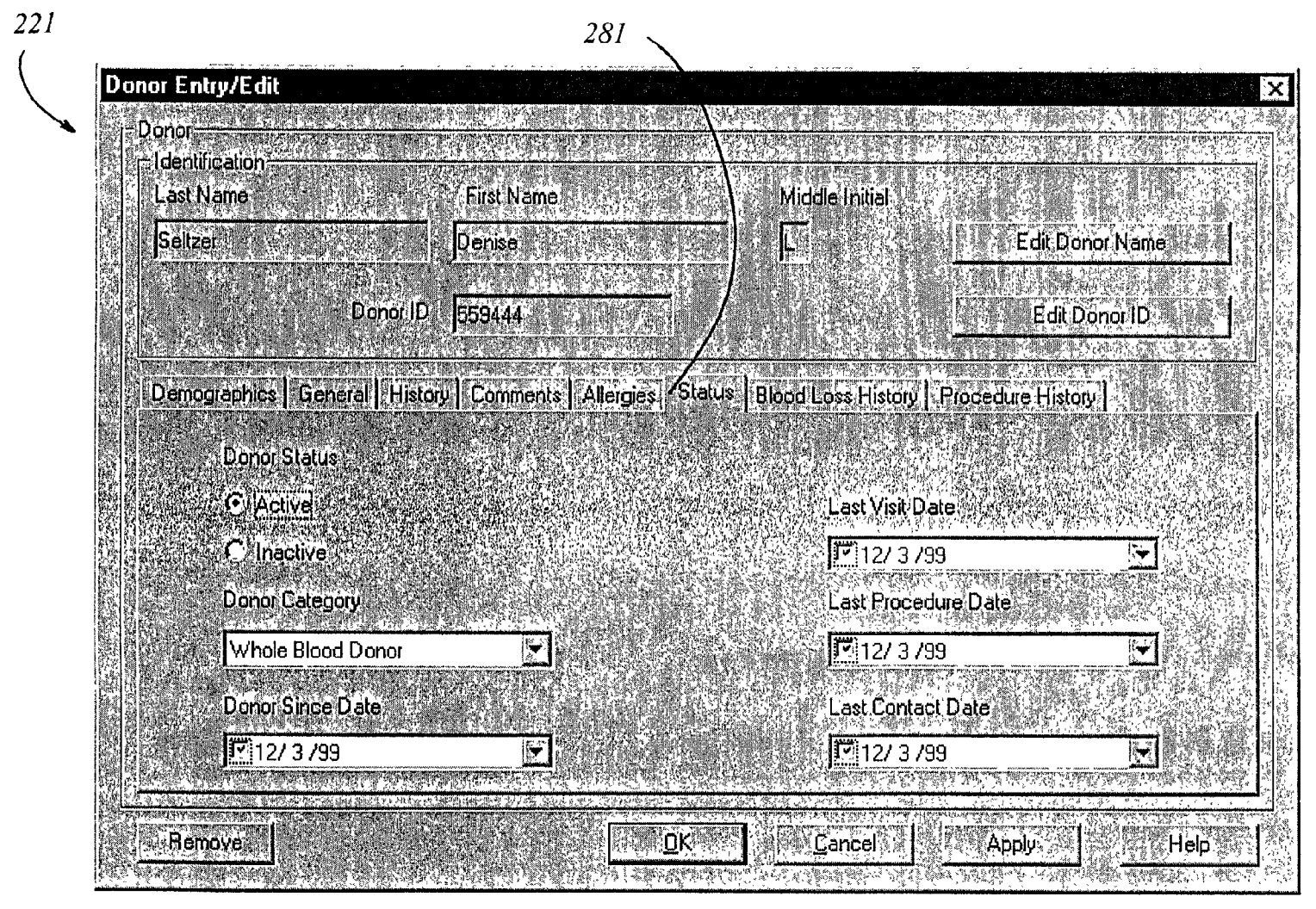
Figure 2H:
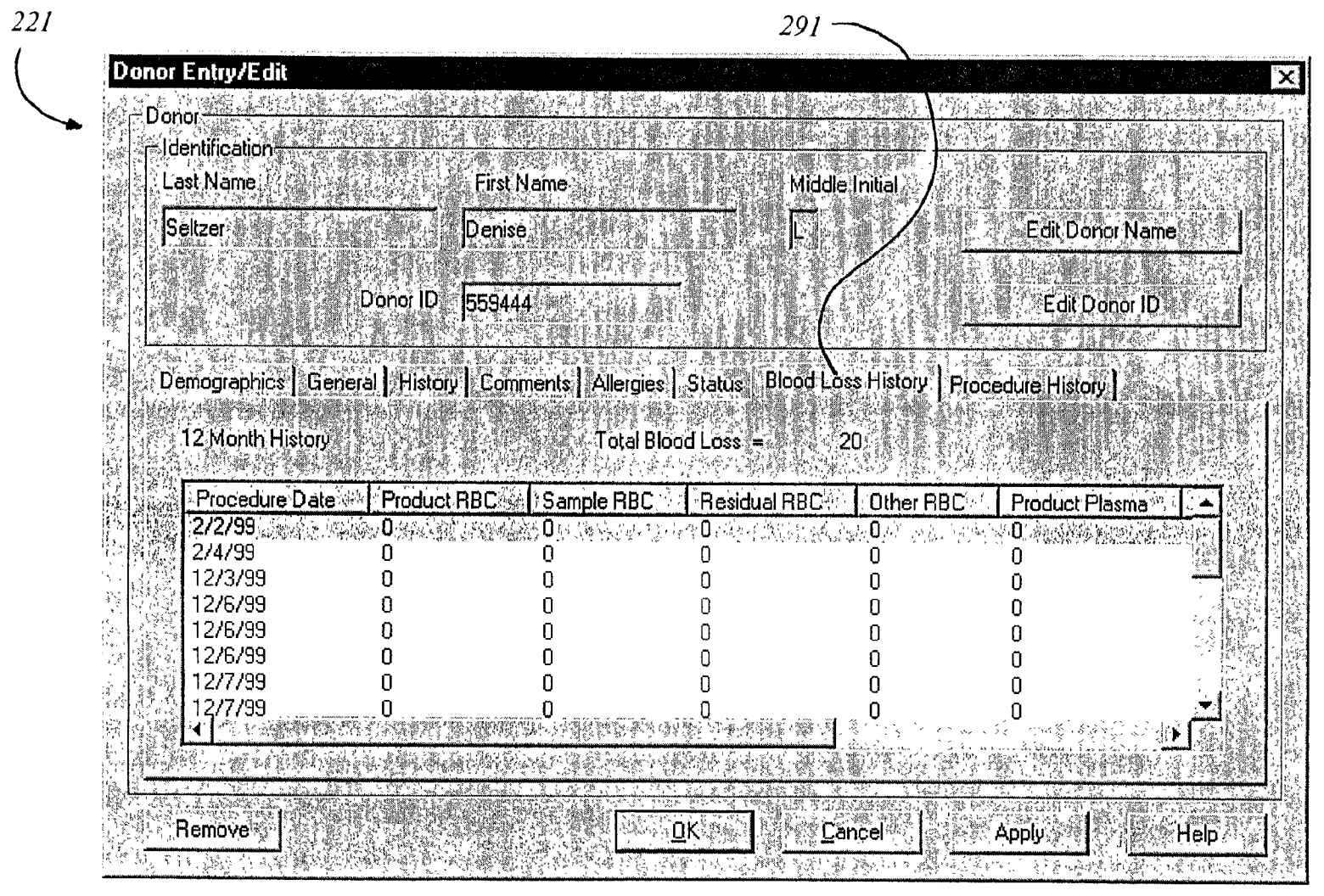
Figure 2I:
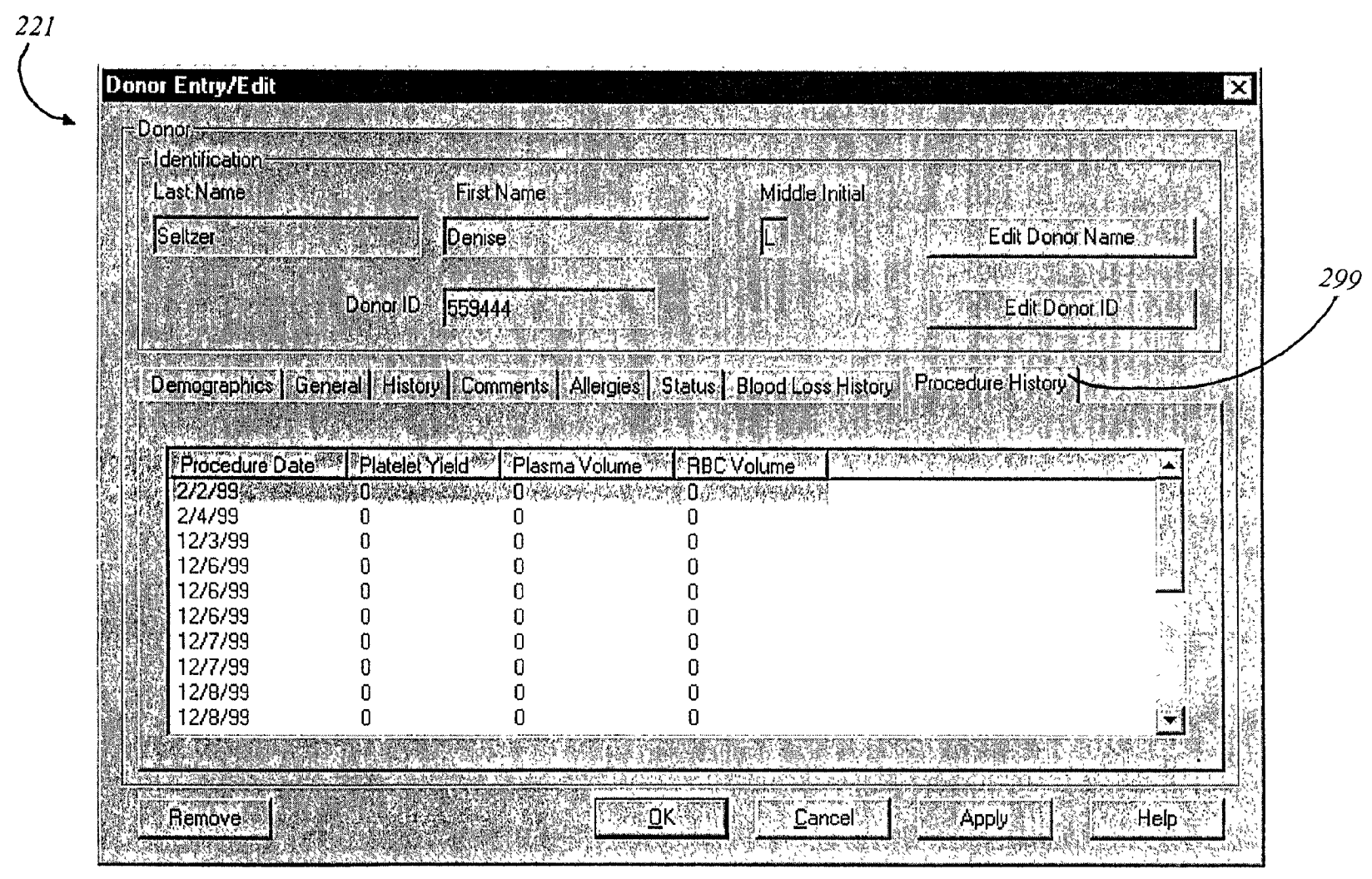

The operator may also decide to remove an allergy from the Donor Allergies list. The operator may then click the allergy in the Donor Allergies list, and then click the Remove Allergy button. The allergy is removed from the displayed list; however, the allergy is not permanently removed from the donor record until the operator then clicks Apply or OK button 229 or 230. The operator may decide to enter additional comments for an allergy currently in the Donor Allergies list. The operator clicks the allergy in the Donor Allergies list, and then clicks the Add Comment button. An Allergy Comment dialog box (not shown) may be made to appear. The operator can then enter a comment and click an OK option. The Donor Entry/Edit dialog box 221 reappears, still showing the Allergies tab 271 (FIG. 2F). The allergy listing in the Donor Allergies list is updated to show the new comment. The date and time the comment was created, as well as the user ID for the user who was logged on when the comment was created, will preferably appear with the comment in the Donor Allergy Comment box.

The operator may then optionally click the Status tab 281 (FIG. 2G) to enter/view the following donor status information: Donor Status—Active or Inactive; Donor Category (a drop-down list, preferably created by the System Administrator); Donor Since Date—date the donor started donating (preferably defaults to first procedure date, if not modified, which can be typed in text box or selected using a pop-up calendar); Last Visit Date—last date the donor attempted to donate (defaults from system records, preferably non-editable except by the System Administrator); Last Procedure Date—the last date the donor actually did donate (default from system records, non-editable except by the System Administrator); Last Contact Date—last date that the center contacted the donor (can be typed in text box or selected using pop-up calendar, default is preferably the current date).

The operator may then optionally click the Blood Loss History tab 291 (FIG. 2H) to view the total volume of blood the donor has lost from apheresis (not whole blood) activities for the previous 12-month period. All of the data in this tab is preferably non-editable in this module. It is downloaded as run data from the apheresis collection system 10 (preferably a Trima® system 10) for procedures run for this donor, and/or entered by an operator during procedure finalization (see below). The tab 291 preferably shows the Total Blood Loss the total volume (preferably in milliliters) of blood the donor has lost from apheresis (not whole blood) activities for the previous 12-month period); and a Procedure table which shows blood loss for apheresis procedures for which a procedure record exists in the central server system 140. Each procedure is preferably listed in a separate row in the table. The operator may need to scroll horizontally or vertically to view some of the data. For each procedure, the table preferably shows the following:

Procedure Date—The date the procedure was run.

Product RBC—The volume of RBC product collected during the procedure (total RBC volume less anticoagulant volume). This information is preferably determined based on the procedure that was run and the donor's hematocrit.

Sample RBC—The volume of sample RBCs collected during the procedure. This volume is either the default value set by the Administrator during system setup or a value entered by an operator during procedure finalization, according to the facility's SOPs (see the Finalize Procedure Record description below).

Residual RBC—The volume of residual RBCs remaining in the tubing set after the procedure. This information is determined based on the tubing set type, the procedure that was run, the donor's hematocrit, and whether or not rinseback was completed for the procedure.

Other RBC—Any other RBC volume (for example, estimated volume of a spill), entered by the operator in the Finalize Procedure Information dialog box, Blood Loss tab, according to the facility's SOPs. (see the Finalize Procedure Record description below).

Product Plasma—The volume of plasma product collected during the procedure (total plasma volume less anticoagulant volume). The information is determined based on the procedure that was run and the donor's hematocrit.

Sample Plasma (not shown in FIG. 2H; scrolled off the right side of the screen)—The volume of sample plasma collected during the procedure. This volume is either the default value set by the Administrator during system setup, or a value entered by an operator during procedure finalization, according to the facility's SOP's (see the Finalize Procedure Record description below).

Residual Plasma (not shown in FIG. 2H; scrolled off the right side of the screen)—The volume of residual plasma remaining in the tubing set after the procedure. This information is determined based on the tubing set type, the procedure that was run, the donor's hematocrit, and whether or not rinseback was completed for the procedure.

Other Plasma (not shown in FIG. 2H; scrolled off the right side of the screen)—Any other plasma volume (for example, estimated volume of a spill), entered by the operator in the Finalize Procedure Information dialog box, Blood Loss tab, according to the facility's SOPs. (see the Finalize Procedure Record description below).

The operator may then optionally click the Procedure History tab 299 to view product information for all procedures run for this donor since the donor record was created in the present system 140. The tab 299 shows product information only for apheresis procedures for which a procedure record exists in the database 142. All of the data in this tab is preferably non-editable. It is downloaded from the apheresis system (preferably a Trima® system) 10 run data for procedures run for this donor. The operator may need to scroll horizontally or vertically to view some of the data. For each procedure, this tab 299 preferably shows the following:

Procedure Date—The date the procedure was run.

Platelet Yield—The yield of platelets collected during the procedure.

Plasma Volume—The volume of plasma collected during the procedure (plasma product volume plus anticoagulant volume).

RBC Volume—The volume of RBCs collected during the procedure (RBC product volume plus anticoagulant volume).

Various alternative data entry/editing actions may also be preferred. For example, at any time while using the Donor Entry/Edit dialog box 221, the operator may click the Apply button 229 (see FIGS. 2B–2F, e.g.) to save all to-date changes to the donor record, without exiting the dialog box. Similarly, at any time while using the Donor Entry/Edit dialog box 221, the operator may click the Cancel button 228 to cancel the current entry session. The system 140 may then prompt the operator to confirm the cancellation. If cancellation is confirmed, the system may lose all unsaved changes and closes the Donor Entry/Edit dialog box 221. A Help button 227 is preferably also provided to present a corresponding help screen (not shown) when desired.

If the facility determines that a donor record no longer needs to be in the central database 142, the record can be permanently removed. This option is preferably only available when an operator with a high level clearance such as a System Administrator user role or the like is logged on to the system. This Administrator or high level operator may then search for and display the donor record in the Donor Entry/Edit dialog box 221, as described and then click the Remove button 226 (see e.g., FIG. 2B). A warning may first be made to appear, informing the operator that the record will be permanently removed from the database 142. If removal is still desired a Yes confirmation button (not shown) may be selected. The following may then occur: 1) both the warning message and the Donor Entry/Edit dialog box 221 may be closed; 2) the Search Results box 204 in the Select Donor task window 201 (see FIG. 2A) would no longer show a listing for the removed donor; 3) the donor record would preferably be permanently removed from the database; and/or 4) an internal record for this donor may be retained elsewhere in the system for reporting reasons.

Moreover, at any time while using the Donor Entry/Edit dialog box 221, the operator may change the donor's name, while retaining the current donor ID. To do so, the operator would preferably click the Edit Donor Name button 223 (see e.g., FIG. 2B) in the Donor Entry/Edit dialog box 221. An Edit Donor Name dialog box (not shown) would preferably be made to appear, displaying all previous names used by the donor, as well as the date the name was changed and the operator who was logged on to the system when the name change was made. The operator may then enter a new name for the donor in the Last Name, First Name, and/or Middle Name boxes, and conclude with an OK option (not shown). The Donor Entry/Edit dialog box 221 would then reappear, showing the changed name. The operator can still also decide to not change the name by selecting a Cancel option in the Edit Donor Name dialog box (not shown) to retain the current donor name; whereby, the Donor Entry/Edit dialog box 221 would reappear, showing the unchanged name. Note that a changed name is not saved in the donor record until the operator clicks the Apply or OK button 229 or 230 in the Donor Entry/Edit dialog box 221.

Similarly, at any time while using the Donor Entry/Edit dialog box 221, the operator may change the donor's ID, while retaining the current donor name. To do so, the operator would click the Edit Donor ID button 225 (see FIG. 2B) in the Donor Entry/Edit dialog box 221. An Edit Donor ID dialog box (not shown) would preferably be made to appear, displaying the current donor ID. The operator could then enter a new ID for the donor in the New Donor ID box, and click an OK button (not shown) to save the ID change. The Donor Entry/Edit dialog box 221 reappears, showing the changed ID. The operator can also decide not to change the donor's ID, and click a Cancel option in the Edit Donor ID dialog box (not shown) to retain the current donor ID; in this case, the Donor Entry/Edit dialog box 221 would again reappear, showing the unchanged ID. Note that a changed ID is not saved in the donor record until the operator clicks the Apply or OK button 229 or 230 in the Donor Entry/Edit dialog box 221.

At any time, the operator can search for and select the record for any donor who is already checked in to the system. However, if the donor is already checked in to the system, the following fields, inter alia, in the Donor Entry/Edit dialog box 221 may be preferably disabled and therefore cannot be modified: General tab: Gender; History tab: Blood Type; Status tab: Donor Status.

Once the appropriate/desired donor data is satisfactorily entered, edited and/or verified using screen 221 (FIGS. 2B–2I), the donor may then be checked-in to the next step in the process, the Prepare Procedure step/sub-procedure (described below). Donor check-in may be accomplished from any view of screen 221 by clicking the "OK" button 230 (or another appropriately labeled button, e.g., "Check-in" if so provided, not shown). This may then send the donor information to the Prepare Procedure portion of the software application (e.g., to the Prepare Procedure software module, if the software is so modulized as is preferred). Alternatively, a pop-up dialog box (not shown) can be made to appear for confirmation that donor check-in is desired. "Yes" or "No" options may be provided in such a pop-up dialog box to confirm the operator's desires. Clicking the "Yes" option will then pass the donor information to the Prepare Procedure Step, as described. Note, clicking the "No" option will provide for not passing the donor information to the next procedural step; however, it may be made to either save all edited/entered information while exiting the Donor Entry/ Edit screen 221, or it may be made to call up a further pop-up window to confirm whether the edited/entered information should be saved to the central memory 142 before exiting the Donor Entry/Edit screen 221. Note also that, as will be described below, the donor data entered/edited via screen 221 may be made further enterable/editable at later stages of the overall procedure after initial check-in, still preferably through use of a screen 221, or the like. Thus, provision (preferably through clicking the Select Donor icon 207 in bar 205; see FIG. 2A) may be made to return to screen 221 or the like at later stages of the procedure to enter new data or modify existing data, as may be desired. However, at such later stages, a check-in option would not preferably be made available if (as would be true in such a situation) the donor had/has already been checked-in. Thus, clicking the "OK" button 230 (see FIG. 2B, e.g.) would only save the information to the donor record in memory 142 and not proceed to a "Check-in" dialog box, if used (not shown).

FIG. 3A shows the next step in the overall general component collection procedure which would appear after donor check-in is completed as described above. This next step corresponds generally with the shown display screen 301 which would have been accessed via clicking on the Prepare Procedure icon 208 in the procedure icon area 205. This next step in the data entry/manipulation process shows, via the display screen 301, the donors who have been checked into the system and are now ready for selections of the desired collection procedures to be performed. The work area 202 of screen 301 in FIG. 3A then preferably displays a listing of donors (via a text list (not shown) or by representative icons as shown, or otherwise (not shown)), which have been checked-in according to the above-described procedures(s). This grouping or listing of checked-in donors may also be referred to as a "donor queue." A donor may then be selected from this queue by clicking the corresponding icon 302 or 303, for example. Once the donor is selected in screen 301 (selection being indicated by distinctive shading, see icon 303 in FIG. 3A), the next step can be accessed by clicking the "Prepare" button 304 in the main work area 202, or, in an optional embodiment, by again clicking the "Prepare Procedure" icon 208 in the icon area 205. Note, a "Remove" button 305 could alternatively be selected to remove the donor from the Checked-in Donor Queue, (ie., from the work area 202) if desired. Also, help may be obtained at any time by selection of the "Help" button 306. Note, in a preferred embodiment, the donor icon(s) 302 and/or 303 may include the donor's photo (i.e., as introduced above, the computer/database system 140 may also be equipped with a digital camera as is known in the art of computer systems generally).

There may be at least two general and perhaps overlapping preferences for separating the Donor Check-in functionality from the Prepare Procedure functionality. Specifically, a first such preference may derive from the three room scenario suggested/described above, wherein a donor may be greeted by a receptionist or receptionist-type of operator in a "Reception" room or area. Then, the donor information described generally above (see FIGS. 2A–2I, e.g.) may be entered and/or edited and/or verified at such a "Reception" point of the overall procedure. The donor may then be moved to a second, discrete room where a second, discrete operator may perform the Procedure Preparation steps described hereinbelow. These rooms/areas may be separate physically or rather may not actually be separate at all, depending upon the blood center and its preferred operating procedures and facility arrangements. The operators may also not be discrete; however, the second, likely overlapping preference for the functionality separation may be that there are two separate operators and the second operator may have different technical skills and/or qualifications from the first operator, i.e., the second operator may be qualified to run the actual collection procedure while the first, reception operator/person may not. Thus, by separating these functionalities (even if the "rooms" are not separated), the reception person or the reception area computer may be given access limited only to the Select Donor icon functionality, for example. At the same time, the perhaps higher qualified collection operator may be relieved of the data entry/edit tasks associated with initial check-in procedures.

Figure 3B:
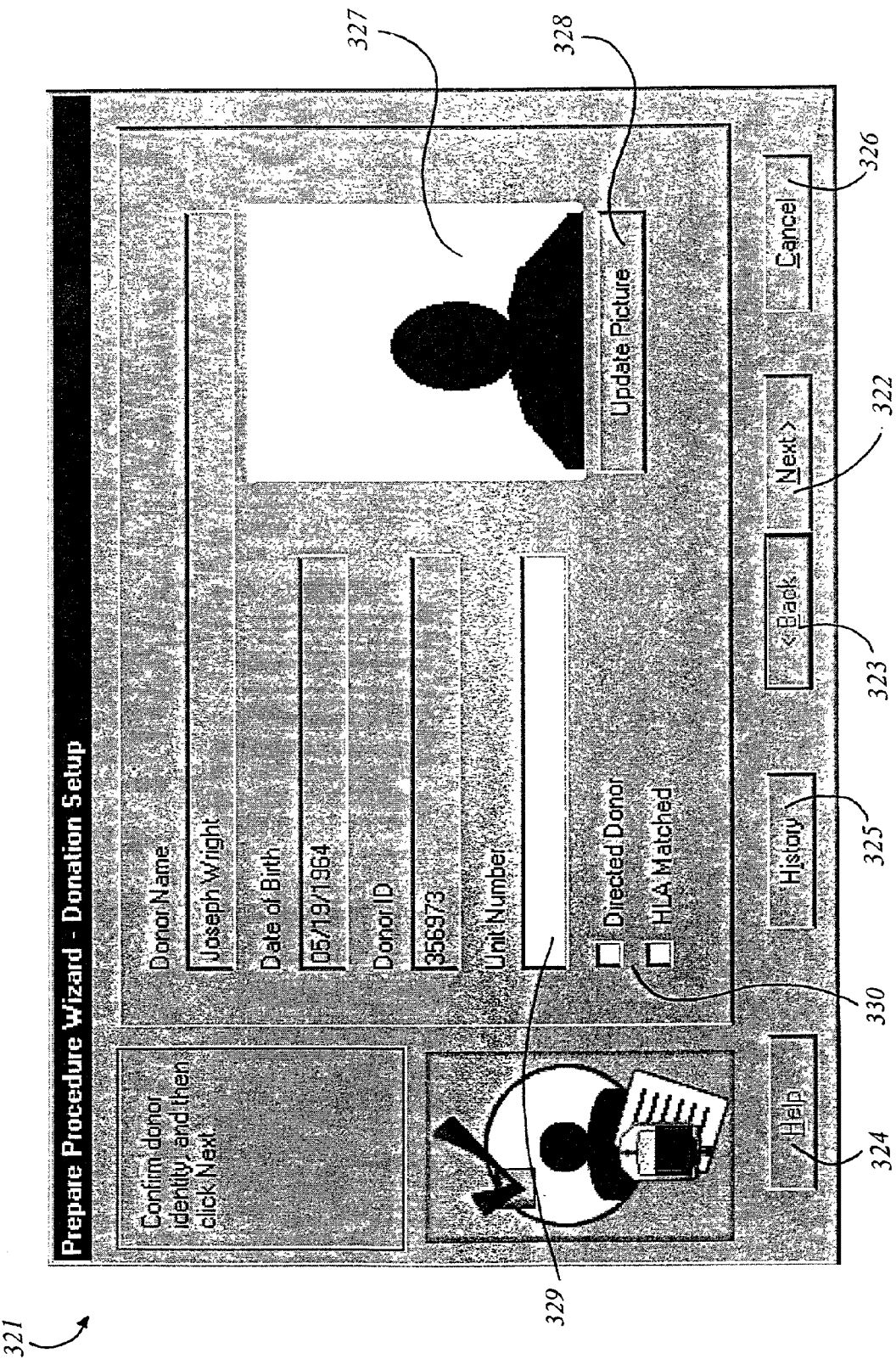

As a result of finishing the previous steps (data entry modification and donor check-in), the Prepare Procedure portion of the overall process may be performed next. As shown in FIG. 3B, a "Prepare Procedure" sub-procedure, preferably a "Prepare Procedure" Wizard, as depicted by a first Wizard display screen 321, may substantially automatically lead the operator through the procedure preparation process. Note, a wizard as known in the art generally, may be a software module or sub-procedure which includes a series of screens used to accomplish a particular task or operation. Note, this "Prepare Procedure" wizard screen and/or other such screens (as follow) may be sub-windows or full window-sized displays.

In particular, as shown here, respective screens 321, 331, 341, and 351 of respective FIGS. 3B, 3C, 3D, and 3E represent substantially sequential wizard screens accessed initially by the selection of the "Prepare" button 304 (after selection/highlighting a particular donor icon, e.g. icon 303) of screen 321 in FIG. 3A. These wizard screens 321–351 are then sequentially accessed, one to the next, by the selection of the respective "Next" buttons 322 (see lower portions of screens in FIGS. 3B and 3C, e.g.). Backtracking, in reverse order, of these wizard screens is also available by selection of the respective "Back" buttons 323, disposed preferably adjacent the "Next" buttons 322. Other general wizard buttons such as the "Help" button(s) 324, the "History" button(s) 325 and the "Cancel" button(s) 326 may be selected at any general point in this process to obtain respectively assistance/information, a history of data entry/ edits (and/or optionally displayed screen views 321–351, e.g.) and/or to cancel the Prepare Procedure wizard at any time.

Further details of preferred process for using these preferred and like screens will now be set forth.

The operator is presented with the first page of the "Prepare Procedure" module/wizard/ sub-procedure, the Donor Identification page 321 as shown in FIG. 3B. This page shows the donor's name, donor ID, date of birth (DOB), and photo (if previously taken and/or saved in the database 142). This page allows the operator to confirm the donor's identity and, optionally, to take or update a photo of the donor. An "update picture" button 328 may be supplied for providing a new or updated photo. Field specific behavior of these items is preferably as follows: the "Donor Name" is pre-populated with first and last name from the donor record data, and is preferably not editable here. The "Donor ID" is also pre-populated, and preferably not editable. The "Date of Birth" field is pre-populated using localized format, and not editable. And, the "Donor's photo" is also preferably pre-populated to further assist the operator confirm the proper donor is present for this procedure being prepared. If such a photo is not available for this particular donor, a generic male or female icon may be displayed. The operator may then click the "Next" button 322 to proceed to the next page of the wizard.

A Unit Number text box 329 may also be disposed in either of screens 321 or 331 (or elsewhere, see FIG. 3B). A Unit Number is preferably a required field entry. The operator may enter the unit number either by typing the number in the Unit Number box 329, or by using a barcode reader (not shown, e.g., by highlighting the unit number field 329 and then using the bar code reader to scan the supply bar code which would then populated this field 329). The unit number may be supplies related information or taken therefrom as related to the tubing set type used, or the bag identifiers to be used. The Directed Donor and HLA matched boxes 330 are further alternative fields which could be entered/edited at this (or a later) stage of the procedure. These fields are directed to noting whether this donor is providing a donation for a specific pre-identified recipient, and the HLA match box merely records whether the HLA types have already been matched for such a directed donation per pre-existing techniques. The operator may then click the Next button 322 to proceed to the next page, or the Back button 323 to return to the previous page.

Figure 3C:
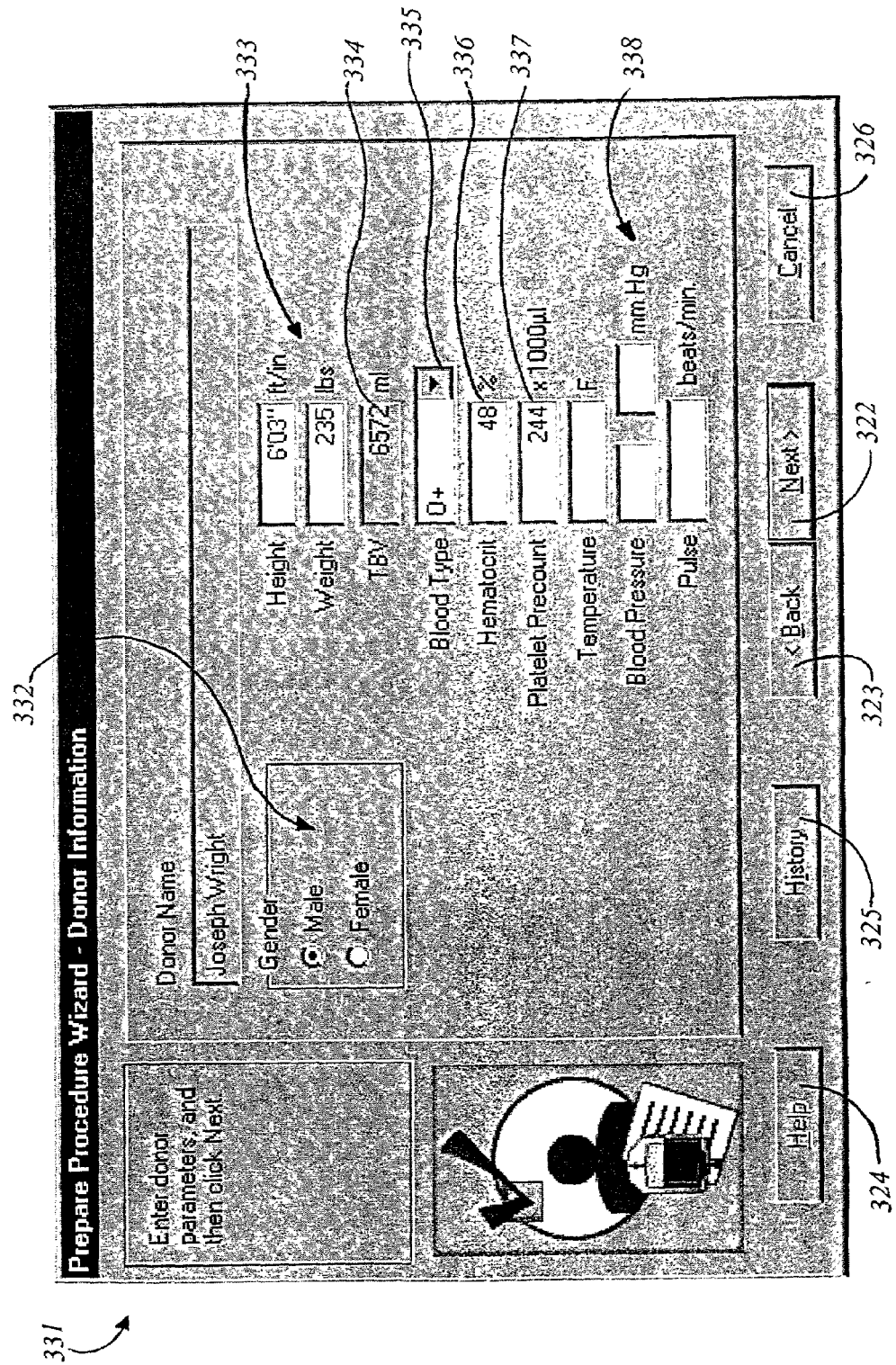
Figure 3D:
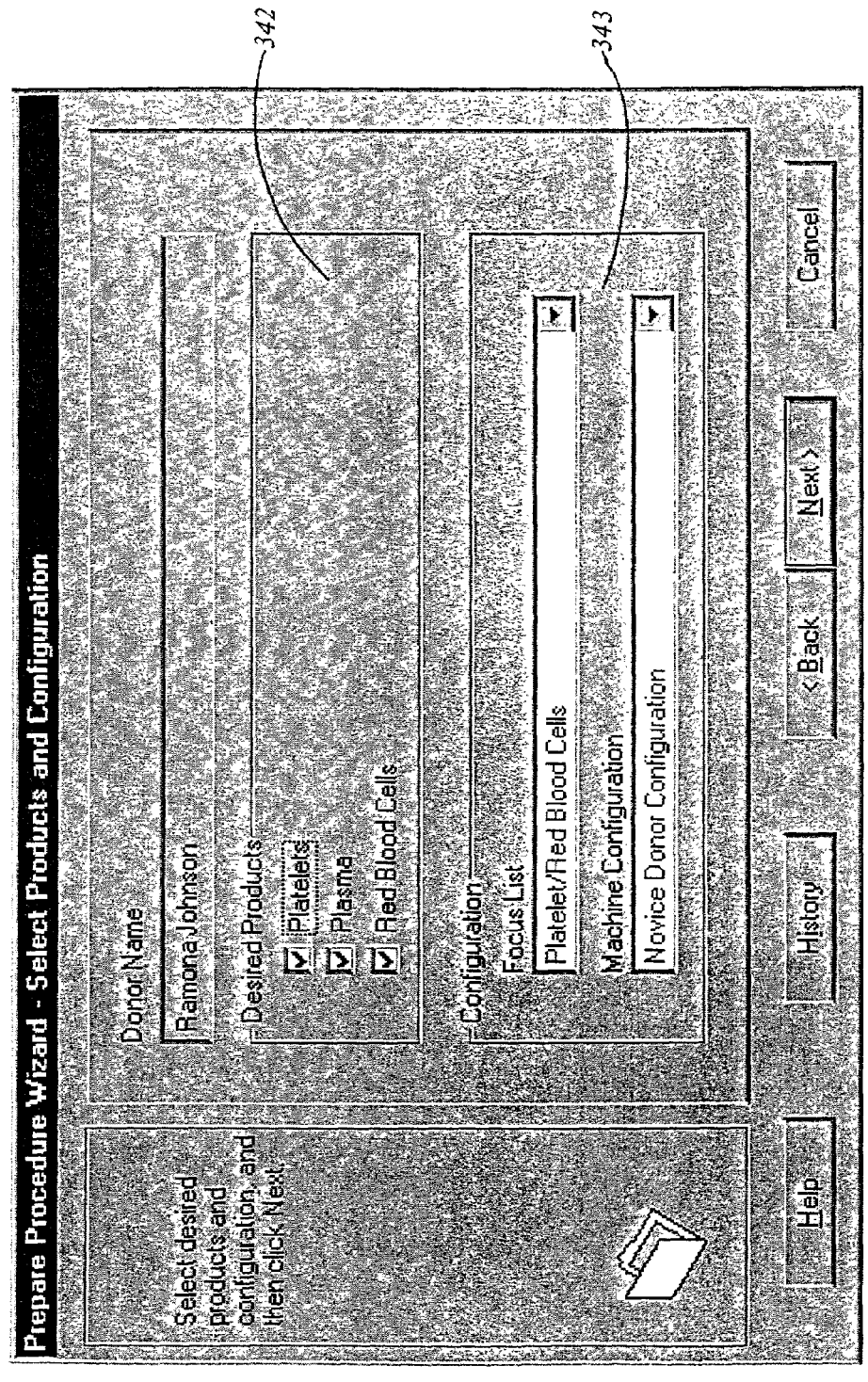

Then, as shown by the display screen 331 in FIG. 3C, gender, height, weight, hematocrit and platelet pre-count parameters will preferably be entered, if not already populated in the respective fields 332, 333, 336 and 337 as previously entered in and thus disposed in the database 142. In fact, even if these parameters are previously entered, these fields in this screen 331 may be made mandatorily re-entered here, or at least re-confirmed before the system 140 may allow the operator or donation process to proceed (note, if re-entered here, it may be that this data re-entry could rewrite the database information at this point or at the end of the collection process as part of the entire record which is saved to the central database 142 at that time). The other fields shown in this FIG. 3C are preferably entered as well, but may be made optional. As introduced above, and as will be understood from further description below, the required fields may be populated with historical data until the current lab values come back.

More particularly, the operator is presented with the Donor Information page 331 of the wizard, see FIG. 3C. Donor "vitals" are taken and entered on this page. The following items are preferably displayed on the Donor Information page 331. The Donor's Gender is preferably pre-populated in field 332, required, and editable via selection: Male or Female. The Donor's Height and Weight are preferably also pre-populated (see fields 333) with the last value (from database 142, if available) in localized units, editable, and required. The value written to the database will indicate if the value was changed. The "TBV" (Total blood volume) in field 334 is dynamically calculated (non-editable), based on the Height, Weight, and Gender fields 332, 333. The Donor Blood type is also preferably pre-populated in field 335, either from database 142 or (if unknown for this donor) pre-populated with Unknown. This field is preferably editable via a selection: O+, O−, A+, A−, B+, B−, AB+, AB−, or Unknown.

The Hematocrit/Hemoglobin field 336 is labeled either Hematocrit as shown or Hemoglobin (not shown), based on the system setup that is defined by the System Administrator. Data in this field is required, and may be entered by the operator, or a default value may exist. If the Administrator configures this field to use a default value, and historical data of the configured type is available for this donor, the field is pre-populated with the historical data. The type of historical data used as the default may be configured by the Administrator to be one of the following types: Average of last three pre-procedure values; Last visit's pre-procedure value; No default value; Gender-based default value; or blood center chosen default value. The value written to the database and displayed on the page indicates if the value is one of the configurable defaults above or if it is a measured value entered by the operator.

The Platelet Pre-count field 337 is also entered here. Data in this field 337 is required, and may be entered by the operator, or a default value may exist preferably as defined by the Administrator. If the Administrator configures this field to use a default value, and historical data of the configured type is available for this donor, the field is pre-populated with the historical data. The type of historical data which may be used as the default may be configured by the Administrator to be one of the following types: Average of last three pre-procedure values; Last visit's pre-procedure value; No default value; Gender or Center-wide default. The value written to the database and displayed on the page preferably indicates if the value is one of the configurable defaults above or if it is a measured value entered by the operator.

In addition to the above, preferably-required items, the operator may enter the appropriate optional donor vitals (see generally fields 338); Temperature (an optional field in localized units: Fahrenheit or Centigrade); Blood pressure; and Pulse (optional fields).

When all required information (and any optional information the operator chooses to enter) has been entered, the operator clicks the Next button 322 to proceed to the next page 341 or 351 (FIGS. 3D or 3E), or the Back button 323 to return to the previous page 321 (FIG. 3B). Note, if a required field does not have an entered value, an attempted click of the Next button 322 will preferably present a prompt that a value must be entered in this field before the wizard can proceed to the next page. Note, if the operator enters a value in a field that is above or below the allowable limits for that field (hard limits), or a value that is unusually high or unusually low (soft limits), a message will preferably be made to appear. If this is a soft limit, the message informs the operator that the value is outside the limits and asks if the operator wishes to proceed. The operator may click a Yes option to use the value and proceed, or No to enter a new value. If this is a hard limit, the operator may be required to enter a new value in order to proceed. Also, if the blood center uses a blood bank information system, a warning message will preferably be made to appear when the operator changes a donor demographic field on the Donor Information page 331 (FIG. 3C). This warning would indicate that the demographics data must be changed in the blood bank information system to be permanently saved.

In a simplified process (usually for operators with lower qualifications, or wanting or needing fewer choices), after the operator has clicked the "Next" button 322 (FIG. 3C), the operator is then presented with the Target Procedure page 351 (FIG. 3E) of the wizard. Screen 341 (FIG. 3D) is skipped in this simplified procedure. The operator may then accept the recommended target procedure (shown highlighted with a rightward-pointing arrow icon 355 in FIG. 3E). Note that the target procedure is obtained by the system 140 running the apheresis time and/or product yield optimization routines such as are run on the Trima® collection systems 10 (and as described below, see description accompanying FIGS. 7–10) in the present system application, and that the parameters for the highlighted procedure are preferably shown above the procedure list. The operator may then optionally click the Finish button 352 (FIG. 3E) to complete the "Prepare Procedure" apheresis procedure selection process.

Figure 3E:
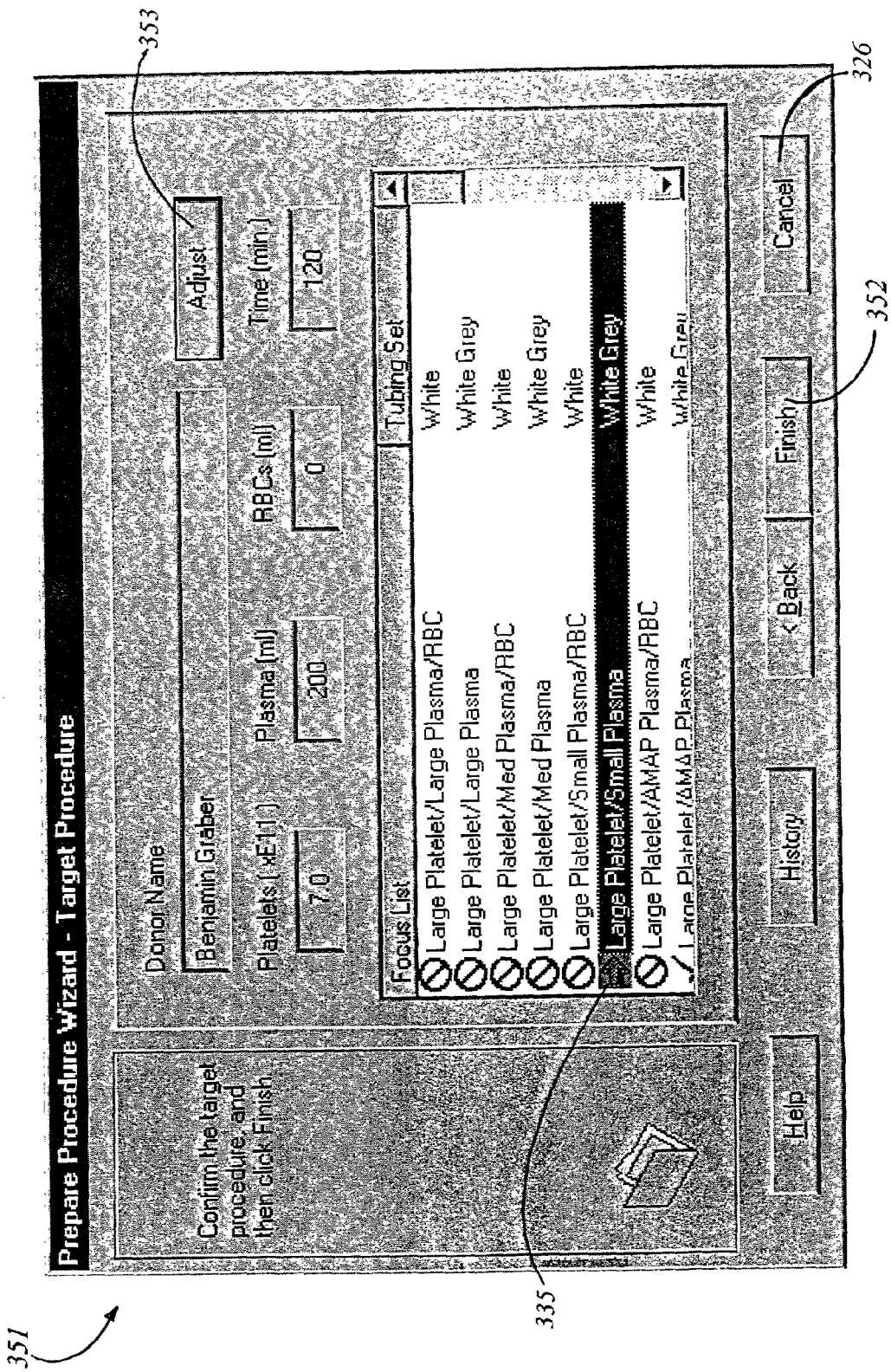
Figure 3F:
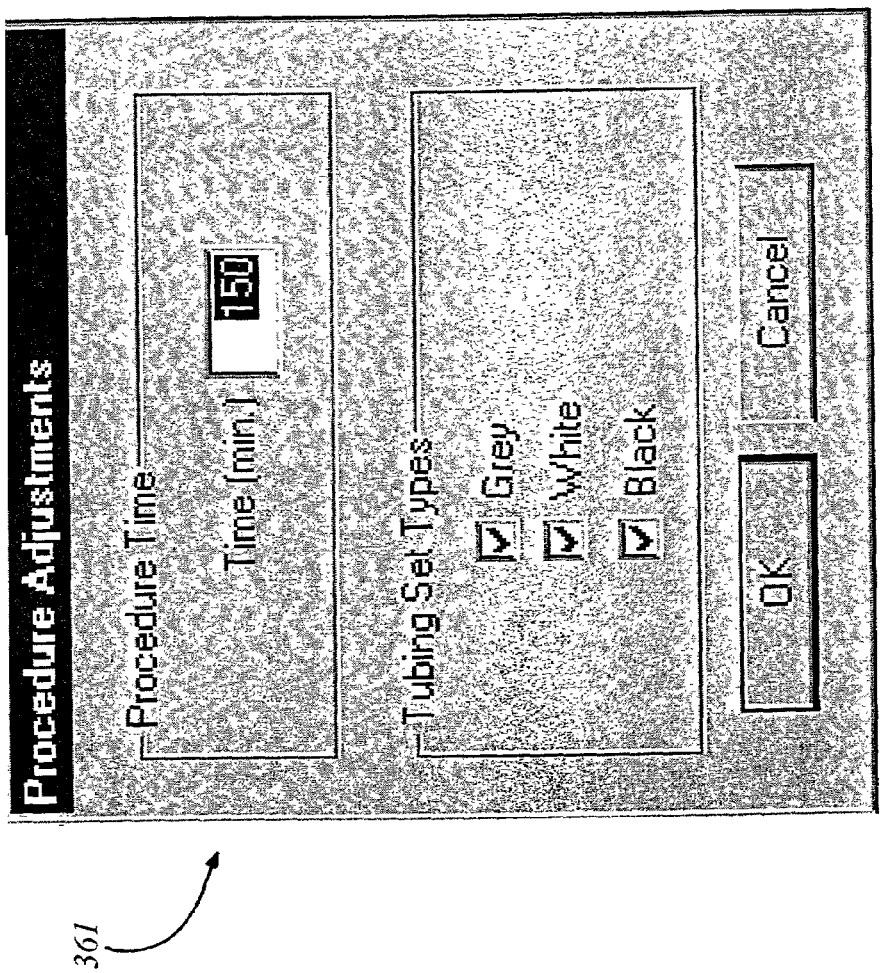

Note, the running of the apheresis optimization routines by system 140 preferably involves the use of data either from storage in the central memory 142 and/or as input into system 140 via input devices 149 at any station 148 (as described hereinabove) preferably through use of the sub-procedures described herein (i.e., using the screens shown in FIGS. 2A–2I and 3A–3C) and communicated through sub-system(s) 146 and then manipulated by the manipulation device 144. The manipulated data may then result in optimized data which can then be interpreted by the system as representing a system preferred target procedure (or procedures) such as is shown in FIG. 3E. Again, optimized data would provide usually either the largest yield in a certain time, or the shortest time to reach a minimum yield (see FIGS. 7–10, below). Other manipulations may provide for procedures which may not be either time or yield optimized, but which a blood center may find otherwise perhaps more desirable, such as platelet (or other component) preferences no matter what the optimization program(s) might suggest. Thus, the system 140 and manipulation device 144 can manipulate the donor statistics (vitals, etc.) against a large plurality of procedure types and compare with blood center prioritizations to obtain various sorts of procedure lists such as that shown in FIG. 3E. Preferably, the optimal procedure (optimized or merely manipulated according to system administrator preselections) may be returned with the rightward-pointing icon 355; however, preferably also other procedures will be listed also with various icon representations to signify prioritization. For example, as shown in FIG. 3E, numerous procedures are shown with a circle with a diagonal line which here preferably represents procedures which are not available due to physical (and/or safety) constraints such as the donor not meeting a minimum hematocrit or total blood volume preferred therefor. Green circles, inter alia, can be used to signify less than optimal procedures which would nevertheless be available for this donor to be subjected to. Question marks could be used to signify procedures which could be available options if the parameters (e.g., time, lab values, etc.) were to change (i.e., if more time were allowed for a collection).

Note several alternative actions may be presented. For example, in some instances it may occur that more than one target procedure may be indicated, whereby the operator may then choose the preferred procedure. Or perhaps the donor may be disqualified such that no procedures appear available. The donor can be disqualified for the donation based on the donor vitals or screening questions. In this situation, the operator may press the Cancel button 326 on any page in the Prepare Procedure Wizard to discontinue the prepare procedure process. The operator may then remove the donor from the Checked-in Donor Queue, as described in the "Prepare Procedure" sub-procedure above.

Otherwise, the donor may be unable to donate if the central system 140 cannot determine a valid apheresis procedure to run for this donor. If this is the case, the central system 140 preferably displays a dialog box (not shown) explaining the reason a procedure cannot be determined. Based on the blood center's policy, the operator may ask the donor if the donor can stay longer. The operator may then extend the procedure time, as described in the "Adjust Donation Time" alternative sub-procedure below.

As noted, the operator may adjust the donation time. If the donor can only stay longer or perhaps only a certain limited amount of time, the operator may change the default maximum procedure time by clicking the Adjust button 353 (FIG. 3E). The operator is presented with the Procedure Adjustments dialog box 361 (see FIG. 3F), in which the operator may enter a new maximum procedure time. The operator may then click the OK button to return to the Target Procedure page 351 (FIG. 3E) of the wizard. If the maximum procedure time is changed, the Target Procedure page is re-optimized and possibly recommends a different procedure. It is also possible that there are no procedures available as a result of the time change.

Similarly, the operator may adjust the tubing set type availability. If only certain tubing sets are available, the operator may change the tubing set type availability by clicking the Adjust button 353. The operator again is presented with the Procedure Adjustments dialog box 361, in which all three tubing set types (e.g. Grey, White, and Black options for the Trima® apheresis systems 10; other optional set types and/or designations may be used for other blood processing systems 10, as desired) are checked by default. The operator may uncheck one or more tubing set types. The operator may then click the OK button to return to the Target Procedure page 351 of the wizard. If the tubing set type availability is changed, the Target Procedure page is re-optimized and possibly recommends a different procedure. It is also possible that there are no procedures available as a result of the tubing set availability change.

Note, the operator may also select certain different procedures in the procedure list shown in screen 351 (FIG. 3E). The operator may select a procedure with an icon indicating that the procedure can be run for this donor (though perhaps not the optimal procedure according to the system 140), or a procedure with an icon indicating that the procedure can be run for this donor, but only if the donor's actual hematocrit and/or platelet precount change significantly from the values entered in screen 331 (or the default values used in screen 331). In any event, preferably the operator cannot select a procedure with an icon indicating that the procedure cannot be run for this donor. Note that when the operator selects a different procedure in the list, the parameters for the selected procedure are shown above the procedure list. Note, the operator may also view any of the listed procedure details. To do so, the operator may double-click a listed procedure to view a Procedure Details dialog box (not shown), which may provide more detailed information about the procedure. The operator may double-click either the currently-selected procedure, or any other procedure in the list. The operator may click an OK button to close the Procedure Details dialog box (not shown) and return to the Target Procedure page 351 of the wizard. If the operator double-clicked a procedure other than the currently-selected procedure, the procedure that the operator double-clicked would now preferably be selected (e.g., highlighted) in the Target Procedure page 351.

Note also that an operator may select different donation options, preferably after the step depicted by screen 331 (FIG. 3C), but prior to the step depicted by screen 351 (FIG. 3E). Preferably, however, this option would be limited to higher security users preparing the donation. Then an additional page 341 (FIG. 3D) would appear, allowing finer control of the donation. This page 341 would be presented only to individuals with the higher privilege level. The following two steps could be added for this operator. The operator would choose the blood product types eligible for this donation (e.g. platelets, RBC's or plasma). These choices would be used to disqualify one or more product types from being collected. By default, all product types are preferably eligible for a donation. Thus, a check in the corresponding box in area 342 of the "Select Products and Configuration" page 341 would indicate that the product type may be collected. If the corresponding box is unchecked, any procedure that would collect this product type is disqualified in the Target Procedure page 351 (FIG. 3E). The three choices are platelets, plasma and red blood cells. Any combination hereof may be checked. As shown in area 343, the operator may also select alternative apheresis system configurations or product focus lists to utilize for this donor's donation. Note that these changes would preferably only apply to this donation. For Focus Lists, the operator may select a product focus list from this drop-down list. The center-wide default focus list is preferably pre-populated in this drop-down list. All focus lists that have been defined by the Administrator will then appear in this drop-down list. For Machine Configuration, the operator may select an apheresis system machine configuration from this drop-down list. The center-wide default machine configuration is preferably pre-populated in this drop-down list. All machine configurations that have been defined by the Administrator will then appear in this drop-down list.

At any point while using the Prepare Procedure Wizard, the operator may click the History button 329 (see FIG. 3C) to view the donor's record. When the operator clicks the History button 325, the Donor Entry/Edit dialog box 221 (see FIGS. 2B–2I) appears, showing all information in the donor record. To return to the Prepare Procedure Wizard, the operator clicks the OK button in the Donor Entry/Edit dialog box 221.

Note, the sub-procedure depicted by the screens in FIGS. 3B–3E may be known generally as "screening" in suggesting that these functions may be performed in the second room, the "Screening" room, of the three room model described above.

Figure 4A:
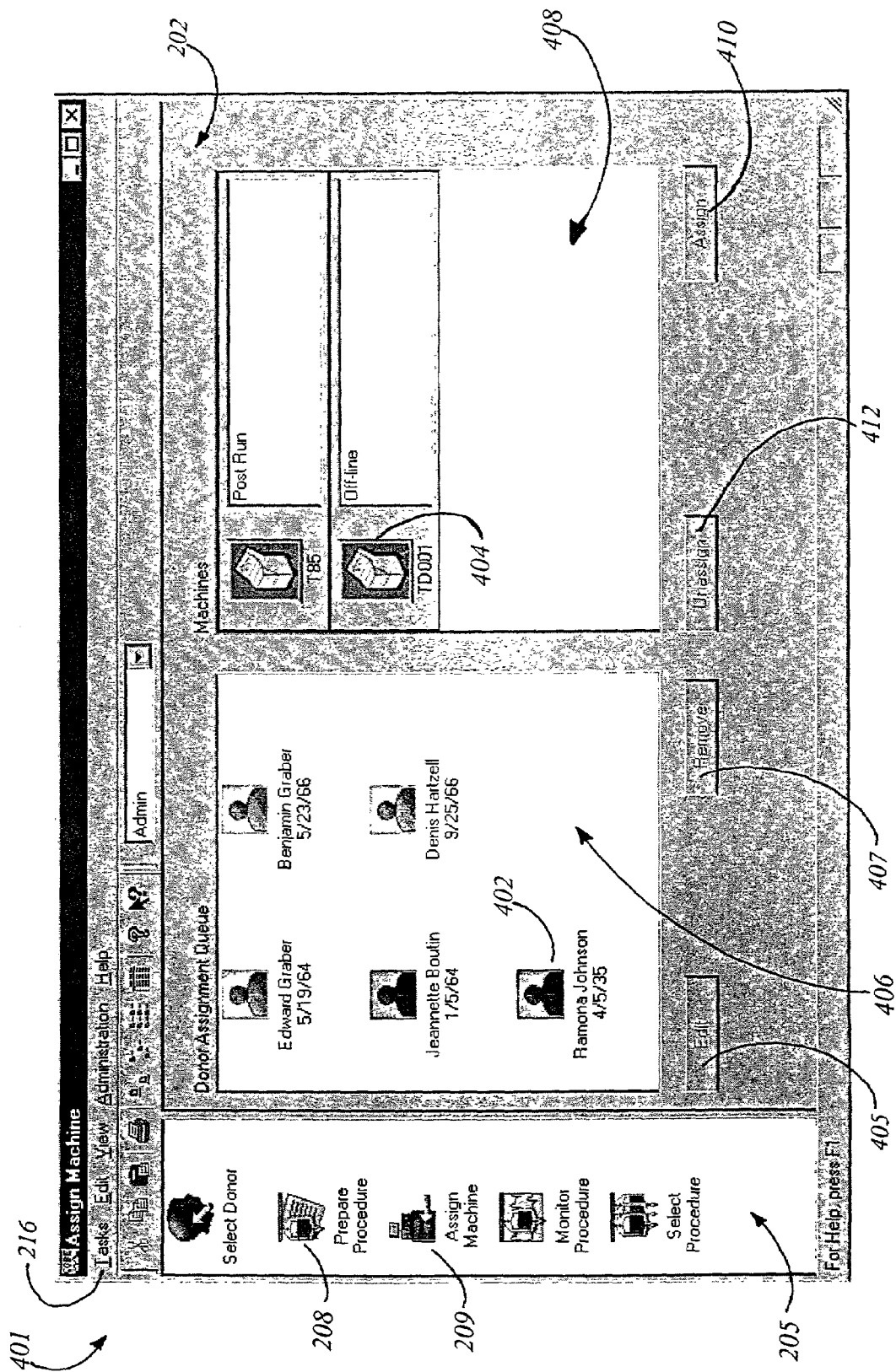
FIGS. 4A and 4B are still further display screen depictions of data entry, retrieval and/or manipulation display pages for use in accordance with the present invention.

Then, in the next procedural step as shown by the display screen 401 in FIG. 4A, the donor may be assigned to a blood processing machine 10. Screen 401 may be accessed via a button such as the "Finish" button 352 appearing on the last page 351 (FIG. 3E) of the "Prepare Procedure" wizard/sub-procedure, or more preferably by clicking the "assign machine" icon 209 appearing in the icon work area 205 (see FIGS. 2A and 4A, e.g.). Assigning a donor to a machine may be a simple matter of clicking and dragging the donor's icon 402 (with or without photo) to an available Trima® or like apheresis machine icon 404 as shown in the respective left and right portions 406, 408 of the main work area 202 in screen 401.

Note however, that any particular donor will preferably not be available (i.e., no icon will preferably show up) in the icon list 406 (also labeled as a "Donor Assignment Queue") until completion of the "Prepare Procedure" sub-procedure (i.e., as accessed using the "Prepare Procedure" icon 208, e.g.) as described for the wizard module in FIGS. 3B–3F. However, after the "Prepare Procedure" sub-procedure is completed, preferably after the clicking of the "Finish" button 352 on the last screen 351 of the wizard (see FIG. 3E), a donor icon for that donor, such as icon 402, e.g. is preferably automatically generated and automatically placed in the icon list 406. Thus, the donor, as represented by the icon, is then ready to be assigned to a particular apheresis assembly 10.

In more detail, to do so, the operator will first preferably double-click the Assign Machine task icon 209 in the main window task bar 205, or, alternatively, the operator may select the Assign Machine element (not shown) from the Tasks menu 216. The Assign Machine task window 401 is then displayed, showing two panes: the Donor Assignment Queue 406 and the Machines list 408. The Donor Assignment Queue 406 shows donor icons (e.g., icon 402) for all donors who are ready for machine assignment. Donor icons are preferably ordered in the queue based on the time an operator finished using the Prepare Procedure Wizard (see above) to prepare a procedure for the donor. The donor for whom the Prepare Procedure Wizard was finished the longest ago preferably appears at the top of the queue. The donor for whom the Prepare Procedure Wizard was finished most recently preferably appears at the bottom of the queue. The Machines list 408 shows an icon for each apheresis system in the facility that is enabled in the current network. To help the operator make a decision about which machine to select for a donor, the following information is preferably displayed as part of each machine icon: run status; time remaining if a procedure is currently running on the machine; name of the next donor queued for the machine; machine communications status (online or offline).

To assign a donor to a machine, the operator preferably selects a donor icon from the Donor Assignment Queue 406 and drags it to a machine icon in the Machines list 408. Alternatively, the operator may select a donor icon 402, e.g., (by highlighting/clicking it once, not shown) and a machine icon 404 and then click the Assign button 410 to make the assignment. A confirmation dialog box (not shown) may then be displayed with "Yes" and "No" options to ask the operator to confirm the assignment. If the operator clicks the "Yes," option, the system may then close the confirmation dialog box, and, in the Assign Machine task window 401, the following preferably occurs: the donor icon 402 is removed from Donor Assignment Queue 406 and the machine information in the Machines list 408 is updated to show that the donor is assigned to the machine. If the operator clicks the option "No," option, the system closes the confirmation dialog box, and, in the Assign Machine task window 401, the following occurs: the donor icon 402 remains in the Donor Assignment Queue 406, and the machine information in the Machines list 408 is unchanged. After a short delay, the donor information (and photo, if available) appear on the apheresis system. In addition, the donation-specific apheresis system configuration is in effect on the machine. At this point, the operator may continue using the Assign Machine task window or select another option in the system main window.

Some alternative process flows for donor/machine assignments are as follows.

It may be possible that all machines 10 are non-functional. If this is the case, the operator (or another member of the facility's staff) will need to fix the problem at those machines 10, to make at least one machine 10 available. If this is not possible, the operator may be required to remove all donors from the Donor Assignment Queue, as described below.

At any time prior to machine assignment, the operator may edit the information about a procedure by selecting the donor's icon (e.g., icon 402) in the Donor Assignment Queue 406 in screen 401 and clicking the Edit button 405. The Prepare Procedure Wizard (see FIGS. 3B–3E) appears, allowing the operator to edit the procedure information. Once the operator clicks Finish 352 on the last page 351 of the wizard, the Assign Machine task window 401 is redisplayed. (Alternatively, the operator may redisplay the Assign Machine task window 401 by clicking Cancel 326 on any page of the wizard; however, in this case, the modifications that were made in the wizard are discarded.)

At any time prior to machine assignment, the operator may remove a donor from the Donor Assignment Queue 406 by selecting the donor's icon (e.g., icon 402) in the Donor Assignment Queue 406 and clicking the Remove button 407. A Confirm Remove Donor dialog box (not shown) may be made to appear, allowing the operator to enter a reason for the removal and/or select a reason from a predefined list (preferably created by the Administrator). Once the operator clicks the OK option in the Confirm Remove Donor dialog box (not shown), the donor's icon is removed from the Donor Assignment Queue 406.

The operator may also unassign a donor from an apheresis system 10 under the following conditions; namely, if another donor is currently donating on the machine, and the donor the operator wants to unassign is queued to donate on the machine, and/or if the machine is offline. To unassign the donor, the operator may click the machine icon 404 in the Machines list 408 and then click the Unassign button 412. The machine icon 404 returns to its previous state. In addition, an icon (e.g., icon 402) for the unassigned donor reappears in the Donor Assignment Queue 406. To distinguish this donor from donors who have not yet been assigned to any apheresis system 10, this donor's icon is gray. The donor may then be reassigned to an apheresis system 10 as described in the basic procedural flow, or removed from the Donor Assignment Queue 406 as described in the "Remove Donor" alternative flow, above. Note: the Unassign button 412 is disabled when no machine icon is selected. If the operator then clicks a machine icon (such as icon 402, inter alia) the Unassign button 412 will remain disabled, the unassign feature not being available for that machine at this time.

If a donor is assigned to an apheresis system 10, but then is dismissed at the apheresis machine 10 using, for example, the touch-screen display 199, the machine icon 402 in the Machines list 408 in the Assign Machine task window 401 returns to the "Ready for Donor" state. In addition, an icon (e.g., icon 402) for the dismissed donor reappears in the Donor Assignment Queue. To distinguish this donor from donors who have not yet been assigned to any apheresis system 10, this donor's icon is "grayed-out". The donor may then be reassigned to an apheresis system 10 as described in the general sub-procedure for Assign a Donor, or removed from the Donor Assignment Queue 406 as described in the "Remove Donor" alternative sub-procedure, above.

Figure 4B:
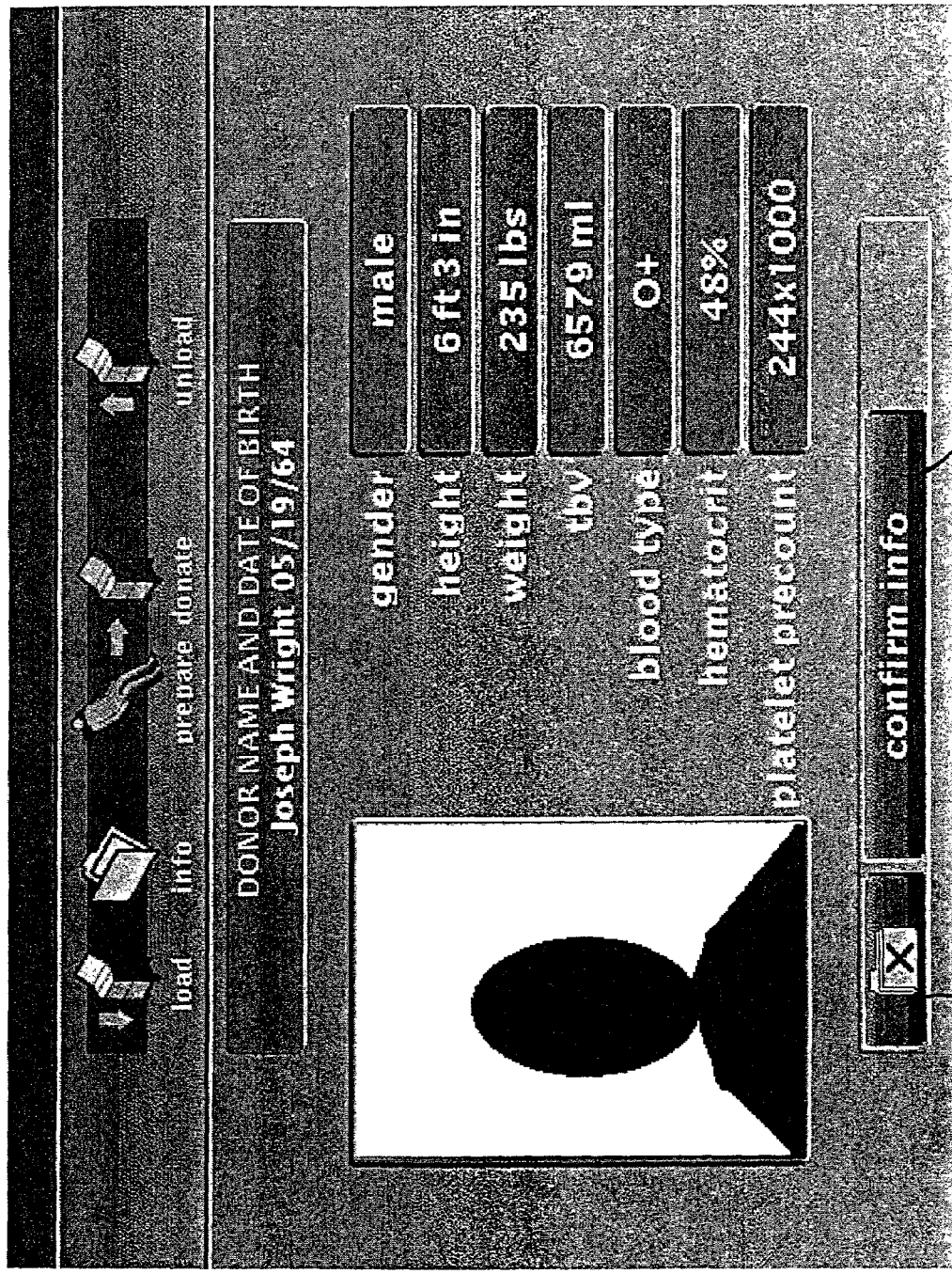

After assigning a donor to an apheresis machine 10 as described, the display screen 421 shown in FIG. 4B appears on the corresponding display area (e.g., touch-screen 199, if used) of the assigned blood component apheresis assembly 10 itself. The operator may then either confirm the information appearing on the apheresis screen 421 by depressing the "continue" button 422, or the like; or the operator may touch/push the box 423 marked with an "X" to decline the donor assignment, thus sending the donor data back to the central system 140 and figuratively send the donor back to the "waiting/screening" room. The apheresis screen 421 shown here may have touch-screen capabilities as understood in the art, or may accept input through other means such as mouse driven cursors, inter alia, which are within the skill of the art.

Note, it is still also conceived that though perhaps not preferable, there may be situations in which the system may be configured to allow the operator to enter data directly on the apheresis machine 10 itself and then perform data manipulation and/or optimization as is known for many existing machines 10 without requiring the use of a central computer/database system 140. Nevertheless, it is also conceivable that in such a situation it may be preferable to still collect data at a centralized system 140 for database or reporting purposes.

After the download of the information from the computer/database system 140 to the actual apheresis machine assembly 10 as described, then the computer/database system 140 may preferably only be used for monitoring and/or reporting. This follows a preference that all actual apheresis control during a procedure remains resident in the apheresis machine 10 itself. It is possible, however, if not preferable, to have computer/database system 140 exert control over apheresis machine functions, including process control manipulation and optimization, during procedures, as well. In either case, as shown in screen 501 of FIG. 5A, it is at this point that the computer/database system 140 can be used to monitor the procedure(s) occurring on one or more apheresis machines 10. All procedure interventions again would preferably occur directly on the apheresis machine 10 through its touchscreen 199 or other input mechanism as known in the art.

Figure 5B:
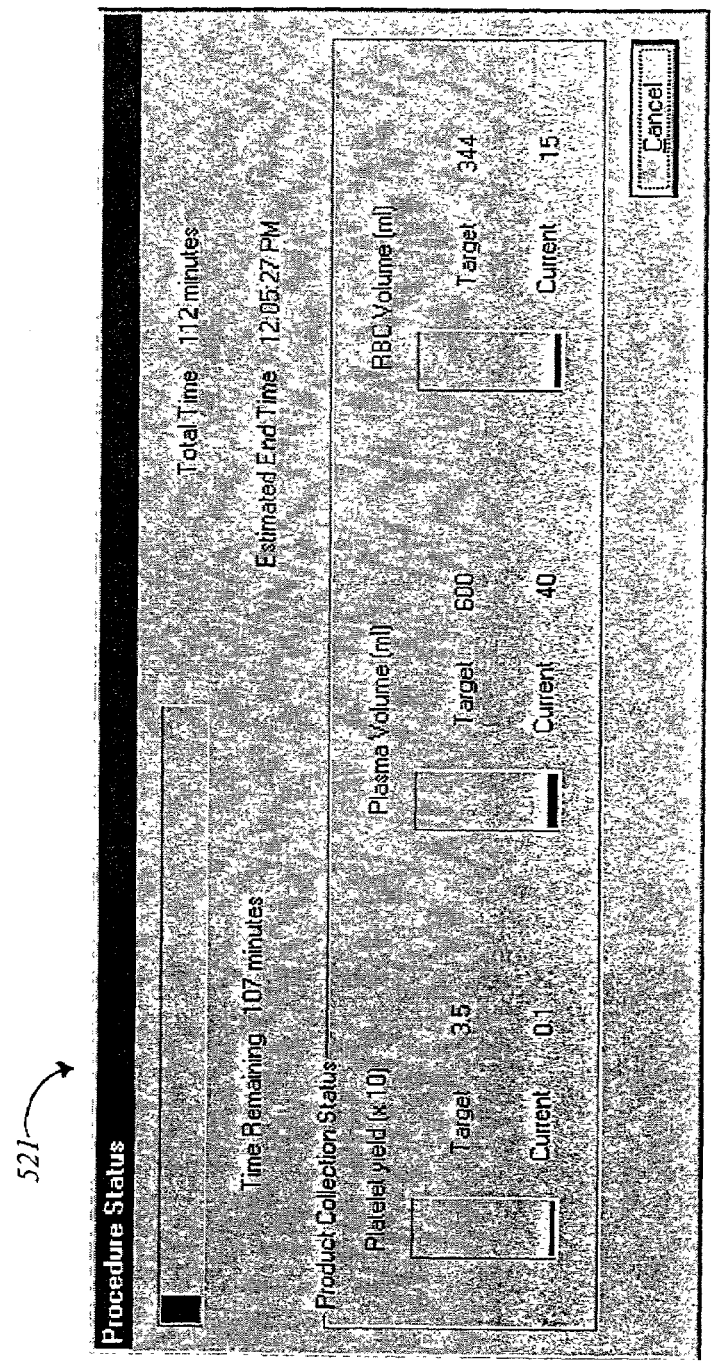

In monitoring mode, real time monitoring of procedures on the centralized computer/database system 140 allows the administrator to know the status of collection of any or all machines 10 at a glance. This can help with scheduling and management. Alarm states may also be displayed and/or all other occurrences and/or activities of each machine may be recorded (not specifically shown). As shown in screen 521, FIG. 5B, detailed data information can be called up to assess the status of a procedure. More details concerning these display screens and the information thereof will now be set forth.

In operation the operator preferably double-clicks the Monitor Procedure task icon 210 in the main window task bar 205 (FIGS. 2A and 5A), or, alternatively, the operator may select the "Monitor Procedure" element (not shown) from the Tasks menu 216.

The present system 140 preferably provides users with the ability to view the status of all procedures currently running on machines 10 connected on the local machine network 146A (see FIG. 1C), as well as procedures which have completed on a machine 10, but for which not all required finalization data has been added to the procedure record. Status information is supplied continuously from each machine 10 to visit status table (not shown) in the central database 142. The Monitor Procedure module scans an internal visit status table recurrently; the Monitor Procedure task window 501 is preferably updated based on the current data in the internal visit status table. Using the Monitor Procedure function, operators can enter a comment about a procedure; enter finalization data about the procedure, such as supplies data and operator roles; view more detailed information about a procedure's status; or force record completion, inter alia.

The basic flow for the monitoring sub-procedure is as follows. Two different general types of procedures are displayed in the Monitor Procedure task window 501; namely Active and Pending procedures. In Active procedures, all of the procedures currently running on machines 10 connected to the machine network 146A, including active procedures currently in an alarm state, are shown. Pending procedures are procedures that have been completed on the apheresis machine 10, but for which not all required finalization data may have been entered in the procedure record.

Note, procedures are considered active from the time that donor and procedure data is downloaded from central system 140 to an apheresis machine 10, until the time that the central system 140 receives indication from the apheresis machine 10 that either the procedure run has been completed, or the operator has indicated on the apheresis machine 10 that the procedure run is incomplete.

In the Monitor Procedure task window 501, procedures are preferably displayed in table format (as shown in FIG. 5A). For each procedure, the following information is preferably displayed: machine ID; collection stage and status; donor name; procedure name; and the time remaining. In addition, an icon (e.g., icon 503) next to each procedure description may preferably indicate if the procedure is in an active, pending, or even an alarm state.

The operator may then optionally select a procedure in the list and then click the Add Comment button 505 to enter a comment in the procedure record for that procedure. An Enter Procedure Comment dialog box (not shown), may then be made to appear. The operator can then select a comment from the pre-configured comment list (preferably created by the System Administrator) and/or enter a free-form text comment entry.

The operator may then optionally select a procedure in the list and then click the Procedure Information button 507 to enter data about the procedure, such as supplies data and operator roles. A "Finalize Procedure Information" dialog box may then appear, showing the Supplies tab. (For more information about this dialog box (not shown), see the "Finalize Procedure" descriptions (FIGS. 6C–6I, below).

The operator may also optionally select a procedure in the list and then click the Status button 509 to view more detailed information about the procedure. A Procedure Status dialog box 521 (see FIG. 5B) may then appear. (Optionally, the operator may double-click the selected procedure in the list to view this Procedure Status dialog box 521.) This dialog box 521 preferably shows the procedure time (time remaining, total time, and estimated end time) and the current collection status for each of the three blood product types (platelets, plasma, and RBCs) which may be in the process of being collected as part of a procedure.

Several alternative conditions and/or sub-procedures may be available in Procedure monitoring. For example, when an alarm, warning or alert condition occurs within an active separation and collection procedure, the system may change the icon next to the procedure description in the Monitor Procedure task window 501 to an "alarm" icon (not shown). The operator can view the alarm description (preferably uploaded automatically to central system 140 from the apheresis system 10 generated by the run data for the procedure) by selecting the procedure from the procedure list in the Monitor Procedure task window 501 procedures list 504, clicking the Procedure Information button 507, and then clicking a Procedure Log tab in the Finalize Procedure Information dialog box (see similar description in FIGS. 6C–6I, below). However, the alarm cannot be resolved in the preferred embodiment directly within the central system 140. The alarm must then be resolved at the machine 10. Once this alarm (and any other alarms on the machine) have been resolved at the machine 10, the central system 140 may change the icon next to the corresponding procedure description back to an "active procedure" icon such as icon 502, for example, as opposed to an inactive icon 503.

At any time, a procedure may no longer meet the active or pending criteria. An update to the visit status table in the central database 142 may cause a procedure that was previously displayed in the Monitor Procedure list on screen 501 of procedures to be removed from the list. Only procedures that have a status of active or pending are preferably displayed in the procedure list. If a procedure previously was active or pending, but no longer meets that criteria the next time central system 140 scans the visit status table, the procedure is no longer displayed in the Monitor Procedure task window 501.

At any point in monitoring procedures using screen 501, an operator may sort procedures in procedure list. In particular, the operator may click one of the column headings in the procedure list to sort the procedures using different criteria. Procedures may preferably be sorted by one of the following: Machine ID, Status, Donor Name (first name, last name), Procedure, or Time Remaining. The first time the column heading is clicked, the procedures are sorted in ascending alphanumeric order. Each subsequent click of the column heading results in a display of the elements in the opposite alphanumeric order (ascending or descending).

As a usual last step in the overall blood component separation and collection process using a central system 140, the record finalization and reporting function of the computer/database system 140 will now be briefly introduced. First, the computer/database system 140 is preferably capable of capturing a great deal of optional information from the apheresis system 10 as well as from manual entry. This end-of-run information may then be used in generating a multitude of optional reports in addition to standard run records, both of which optionally being formattable as desired by the operator (see FIGS. 6K, 6L and 6M, described below). Further, various types of data can be sorted and measured relative to each other as desired as well. For example, the time period of the entire collection procedure can be reported relative to the numbers and/or quantities of the products collected (volumes or contents). Or, certain quality measures may be reported against either or any of the other data collected by the computer/database system 140. In addition, certain data may be manipulated, edited or amended, or comments added thereto after a collection procedure. For example, certain additional information may be added such as information about the type of tubing set used or post procedure laboratory values. Nevertheless, the data generated by the apheresis machine 10, itself, very preferably would not be capable of being edited or changed in any way. As above, more details of the overall reporting functionalities will now be set forth.

The present invention allows operators to search for and select any procedure record in the central database 142, whether the procedure record is opened (as for active and pending procedures) or closed (as for finalized procedures). As shown, for example by screen 601 in FIG. 6A, operators can search for procedure records based on donor ID, unit number, or a range of dates. Once the desired procedure record has been found, the operator can access the procedure record to do one of the following: View and/or enter finalization data (see the "Finalize Procedure Record" sub-procedure described below); or, View and/or enter lab results data (see the "Lab Results Entry/Edit" description below; FIG. 6J)

The Basic Flow of this sub-procedure case follows the scenario that the operator preferably searches by either donor ID or unit number, and that the operator wants to view/enter finalization data for the procedure. The operator preferably double-clicks the Select Procedure task icon 211 in the main task bar 205 (FIGS. 2A and 6A), or, alternatively, the operator may select the "Select Procedure" element (not shown) from the Tasks menu 216 (FIG. 2A). The operator may then search the central procedure record database 142 for the desired procedure record(s), either by donor ID (see field 602) or unit number (field 603). Searching by a range of dates (see fields 604) is another preferred alternative. The operator clicks the desired radio button, which clears any information which may be currently shown in other selection option fields, and the operator then enters a full or partial entry of the donor ID or unit number or dates in the appropriate box. Logical and/or boolean-type searches are also preferably available. Alternatively, the operator may use the barcode reader (not shown) to enter the donor ID or unit number. For date searching, the operator may enter a starting date in the From box, and enter an ending date in the To box. Either date can be typed in the text box or selected using a pop-up calendar (see calendar 611 in FIG. 6B).

The operator may then click the Search button 610 or press the Enter key (on the keyboard, if used). The central system 140 then searches the central database 142 and displays all possible matching procedure records in the Search Results box 612. The search finds both open and closed procedure records. In date searching, the Search Results box displays all procedures that were performed within the specified date range.

Figure 6B:
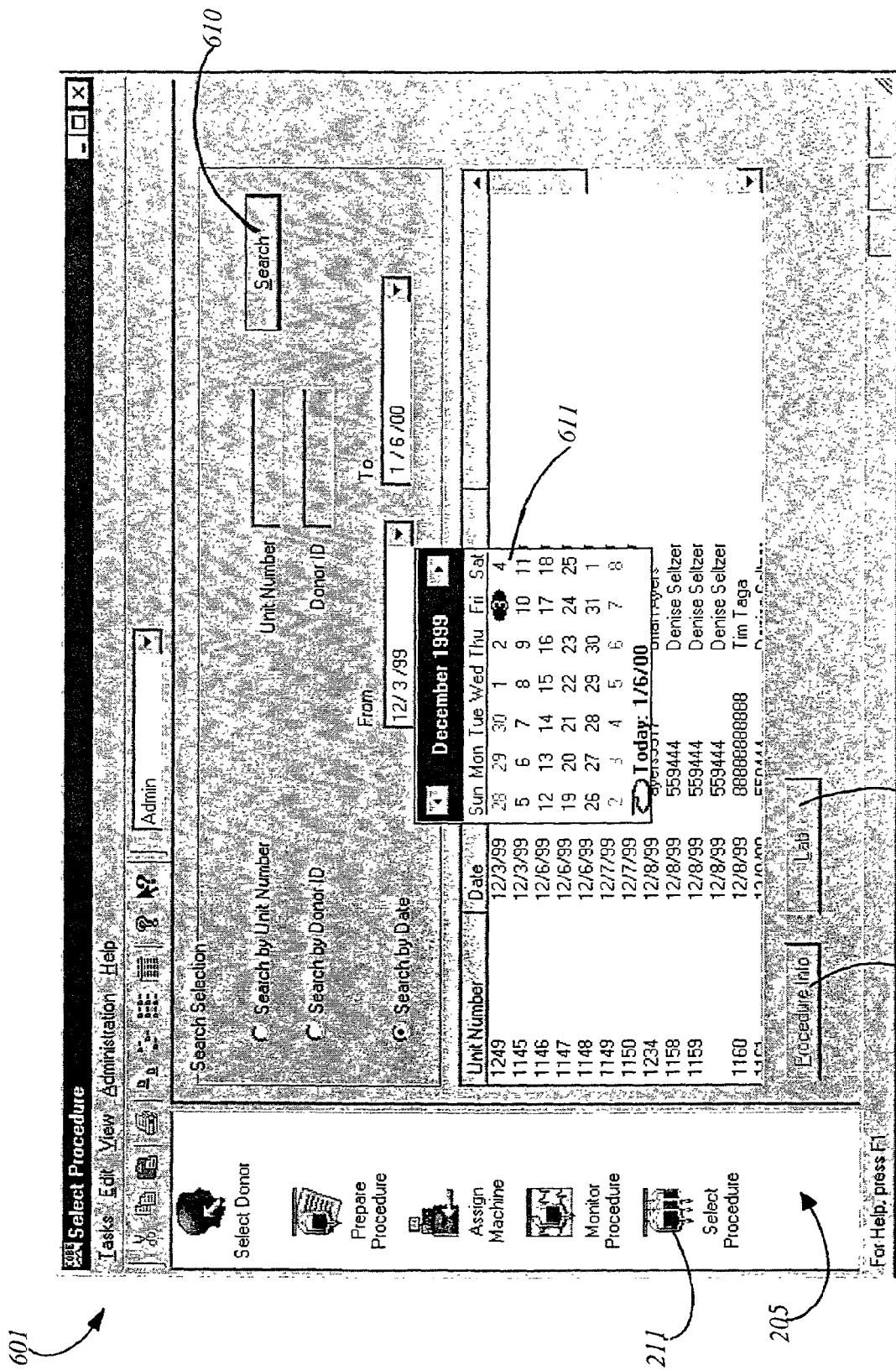
Figure 6C:
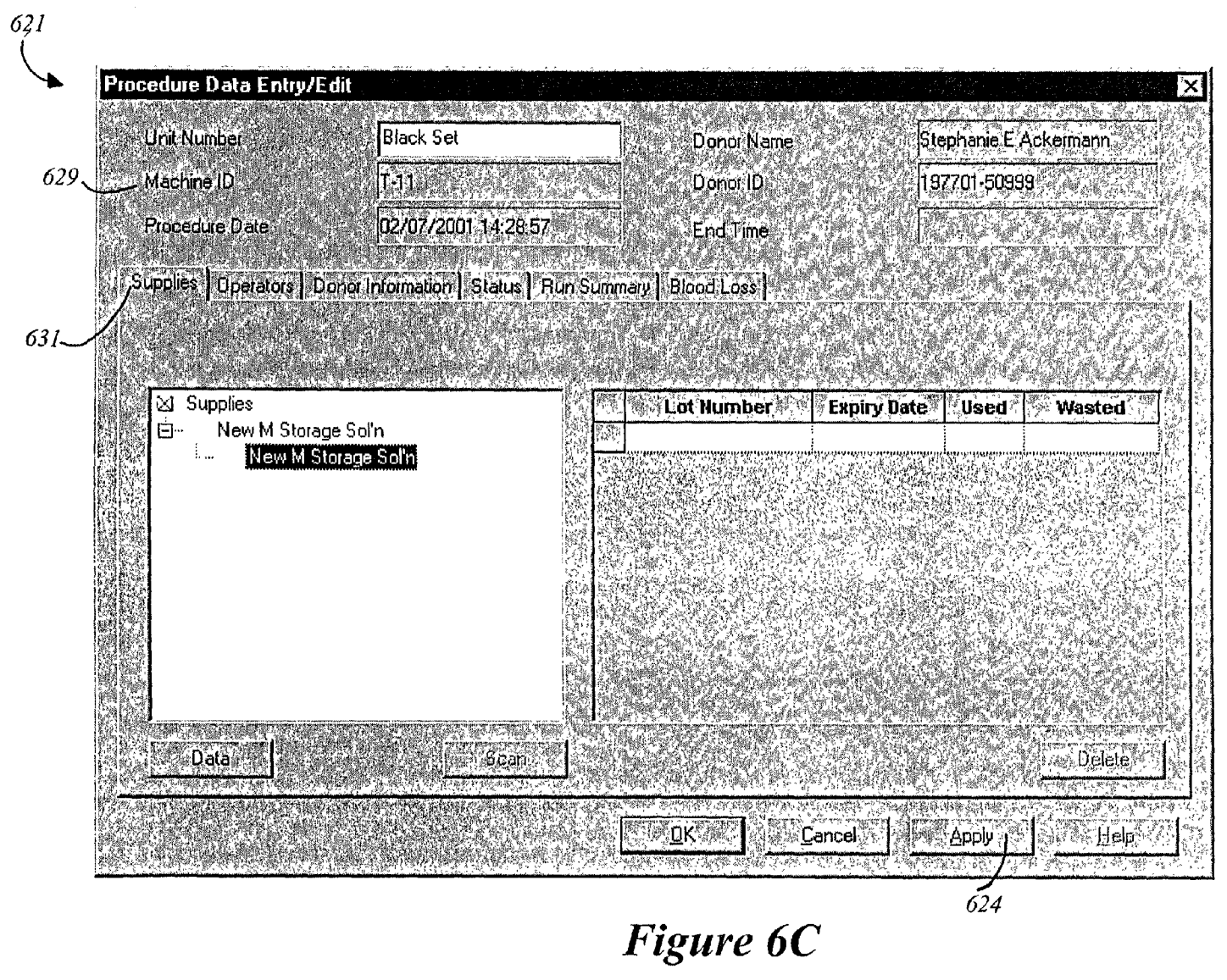
Figure 6D:
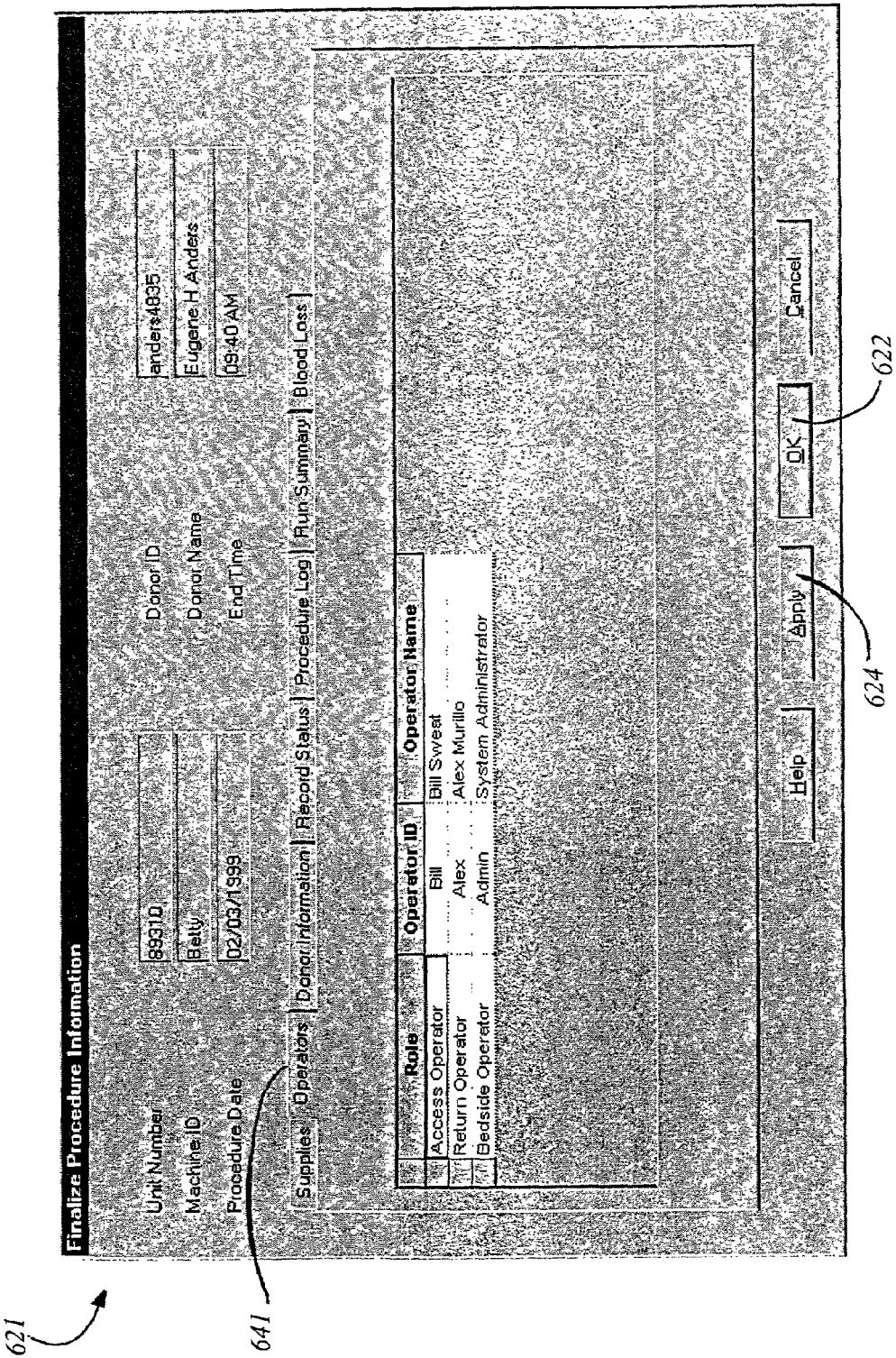
Figure 6E:
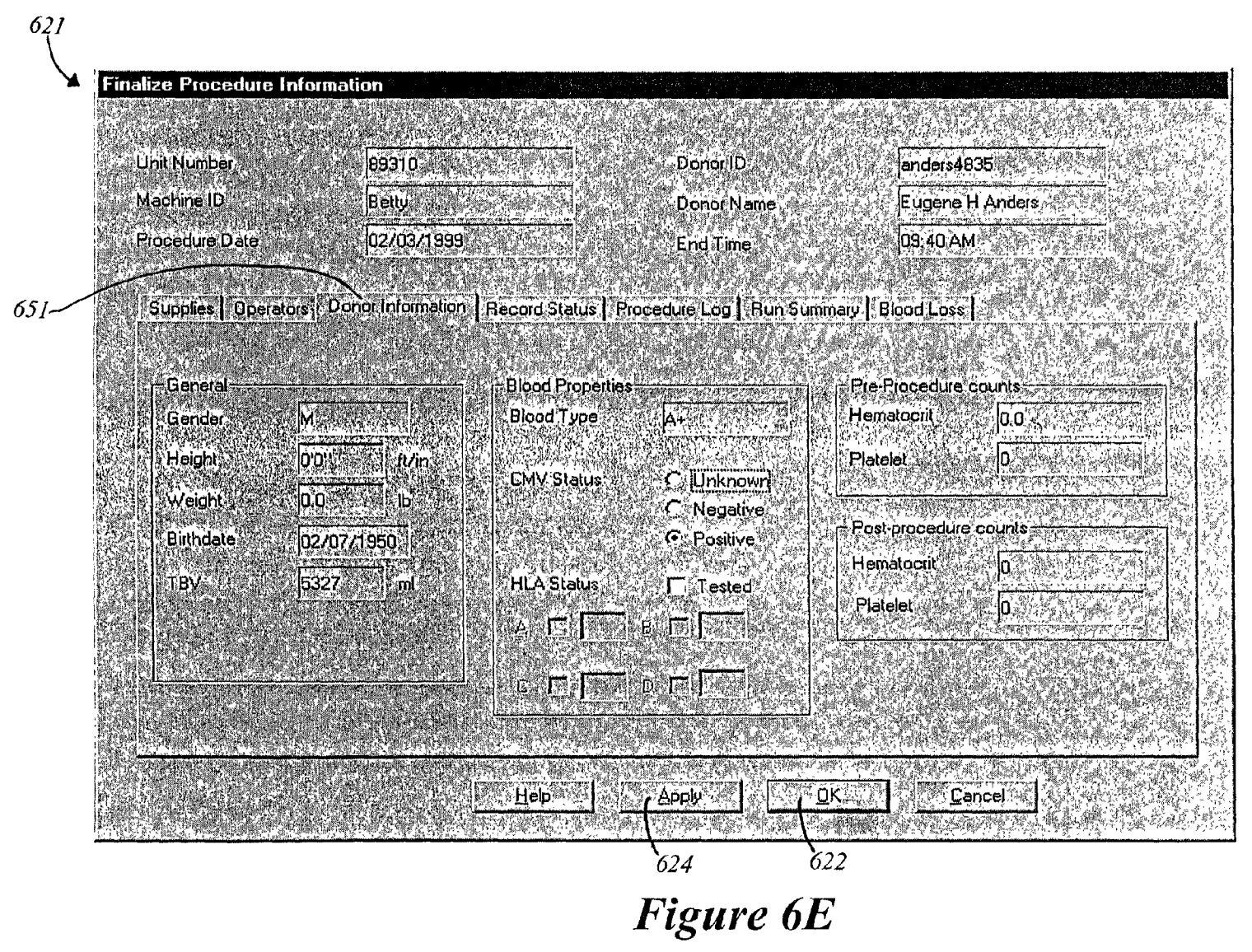
Figure 6F:
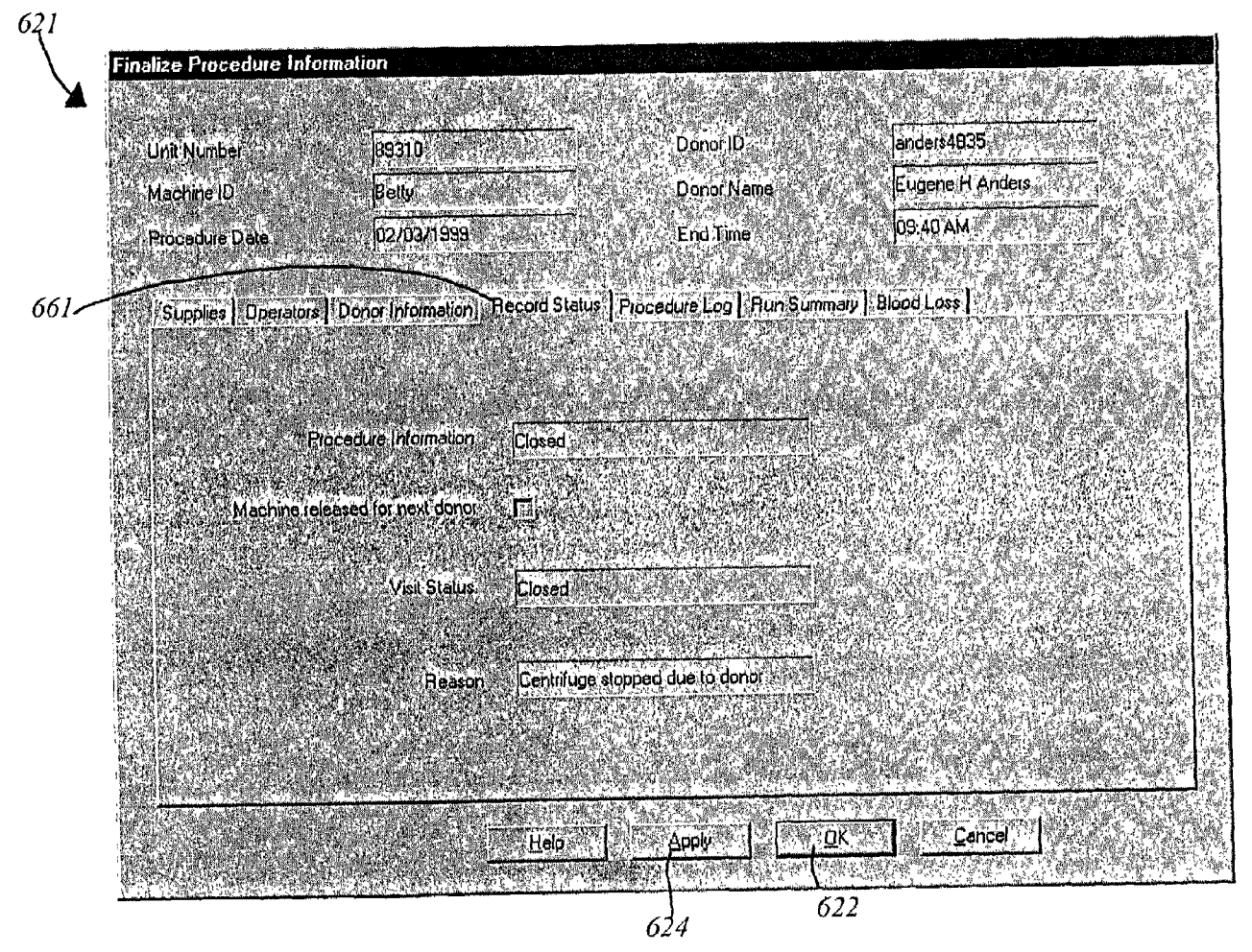
Figure 6G:
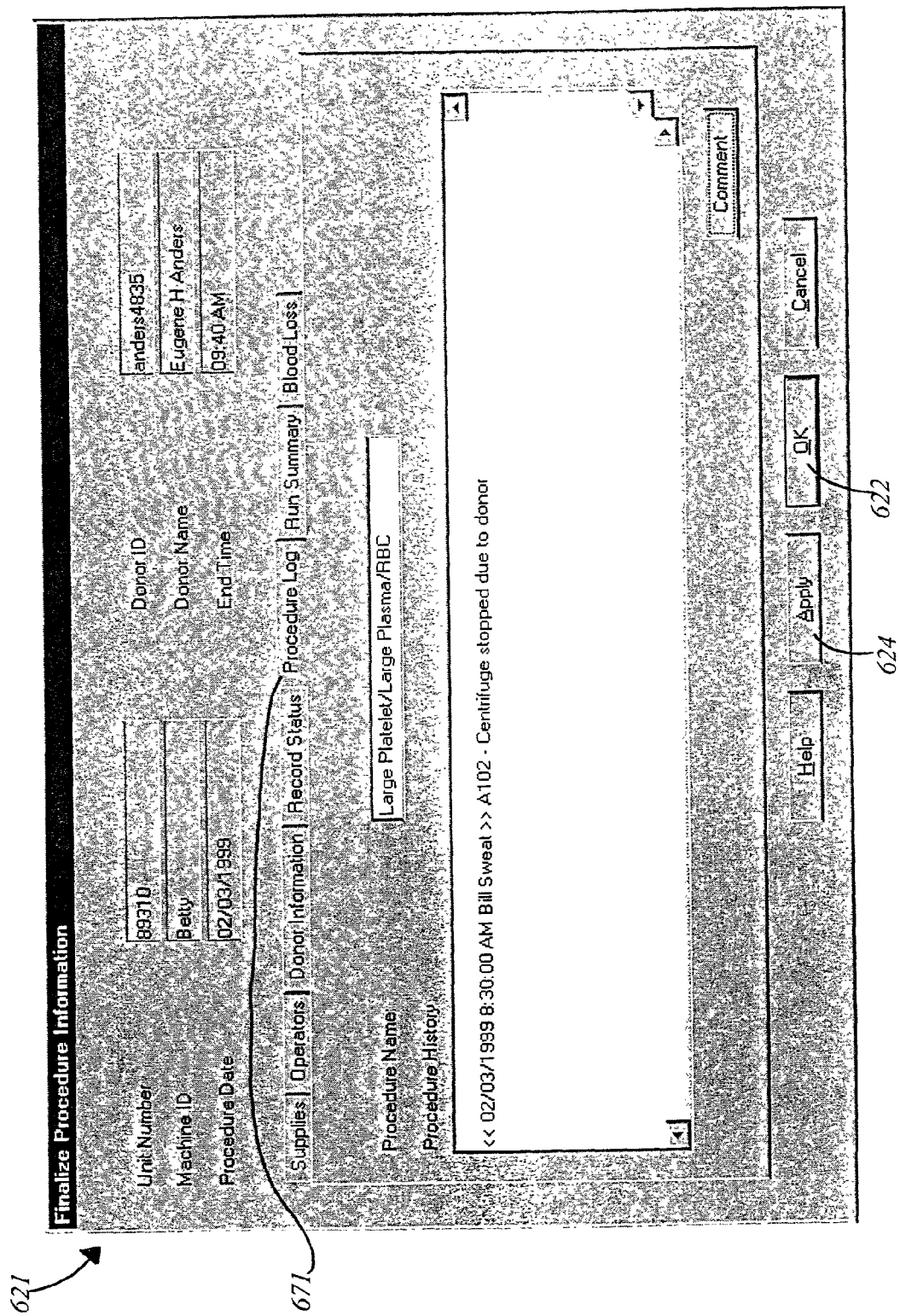

The operator may then click the desired procedure record in the Search Results box 612, and then click the Procedure Information button 614 (shown grayed-out in FIGS. 6A and 6B, since a record is not yet selected there, i.e., is not yet highlighted. A Finalize Procedure Information dialog box 621, which may also be known as a Procedure Data Entry Edit box 621 (see FIGS. 6C–6I) then appears (optional double-clicking of the procedure entry in the Search Results box 612 may also display the Finalize Procedure Information dialog box 62 1), here showing a Supplies tab 631. (For more information about this dialog box, see the "Finalize Procedure" sub-procedure described below.)

Note, alternative search steps may also be performed. For example, if the operator clicks the Search button 610 with no search criteria given, then the Search Results box 612 preferably displays all procedure records in the central database 142. Alternatively, the correct procedure record may not be found, in which case the operator may then perform a new search by entering new search criteria.

Also, the operator may sort procedure records in Search Result box 612 by clicking one of the column headings in the Search Results box 612. This will sort the procedure records using different criteria. Procedure records may preferably be sorted by one of the following: Unit Number, Date, Donor ID, or Donor Name (first name, last name). The first time the column heading is clicked, the procedure records are sorted in ascending alpha-numeric order. Each subsequent click of a column heading results in presentation of the records in the opposite alphanumeric order (ascending or descending). The operator may also view a Lab Results Entry/Edit Dialog box (see box 701; FIG. 6J) by clicking the desired procedure record in the Search Results box 612, and then clicking the Lab button 616 to view the Lab Results Entry/Edit dialog box 701 (FIG. 6J).

The operator may preferably access the Finalize Procedure Information dialog box 621 for a particular procedure using one of two methods, the Monitor Procedure sub-procedure described above (see FIGS. 5A–5B), and/or the Select Procedure sub-procedure (FIG. 6A). The operator can access the Finalize Procedure Information dialog box 621 via the Select Procedure task window 601 (see FIGS. 6A and/or 6B), preferably if the following is true; the procedure will be run, is currently running, or has been run under control of the central system 140. Note that while using Select Procedure, the operator can preferably access the Finalize Procedure Information dialog box 621 regardless of whether the procedure record is opened or closed (this is in contrast to Monitor Procedure; the procedure record must preferably be in open status in order to access it from the Monitor Procedure task window 501). In addition, once the procedure has been completed on the apheresis machine 10, the operator may use the Select Procedure task window 601 to access a Lab Results Entry/Edit dialog box 701 (FIG. 6J), allowing the operator to view/enter lab product results.

Moreover, the operator can preferably access the Finalize Procedure Information dialog box 621 any time after the Prepare Procedure Wizard (see description of FIGS. 3B–3F) has been completed for the donor/procedure. Thus, the operator may enter procedure information such as supplies and operator roles (see below) while the procedure is still running. However, even if all required data has been entered and saved in the procedure record, the procedure record is not considered closed until after the apheresis machine run has been completed (i.e., the central system 140 has detected a reboot or similar such signal from the apheresis machine 10). In addition, in order to update the status of a procedure record from open to closed, all required information must be present in the Finalize Procedure Information dialog box. Required information is preferably either or both dictated by the central system 140 (unit number, machine ID, donor ID, date), and determined by the System Administrator during system setup (required supplies, operator roles, etc.).

Once the central system 140 changes the status of a procedure record from open to closed, the central system 140 preferably removes the procedure from the Monitor Procedure list 504 (see FIG. 5A). After this point, the system 140 may require use of the Select Procedure task window 601 to revisit the procedure record. Note: a procedure is preferably also removed from the Monitor Procedure list 504 if a System Administrator forces record completion using button 511 in FIG. 5A (i.e., when the System Administrator determines that a record cannot or will not be closable in accordance with normal procedures as dictated herein).

Figure 6H:
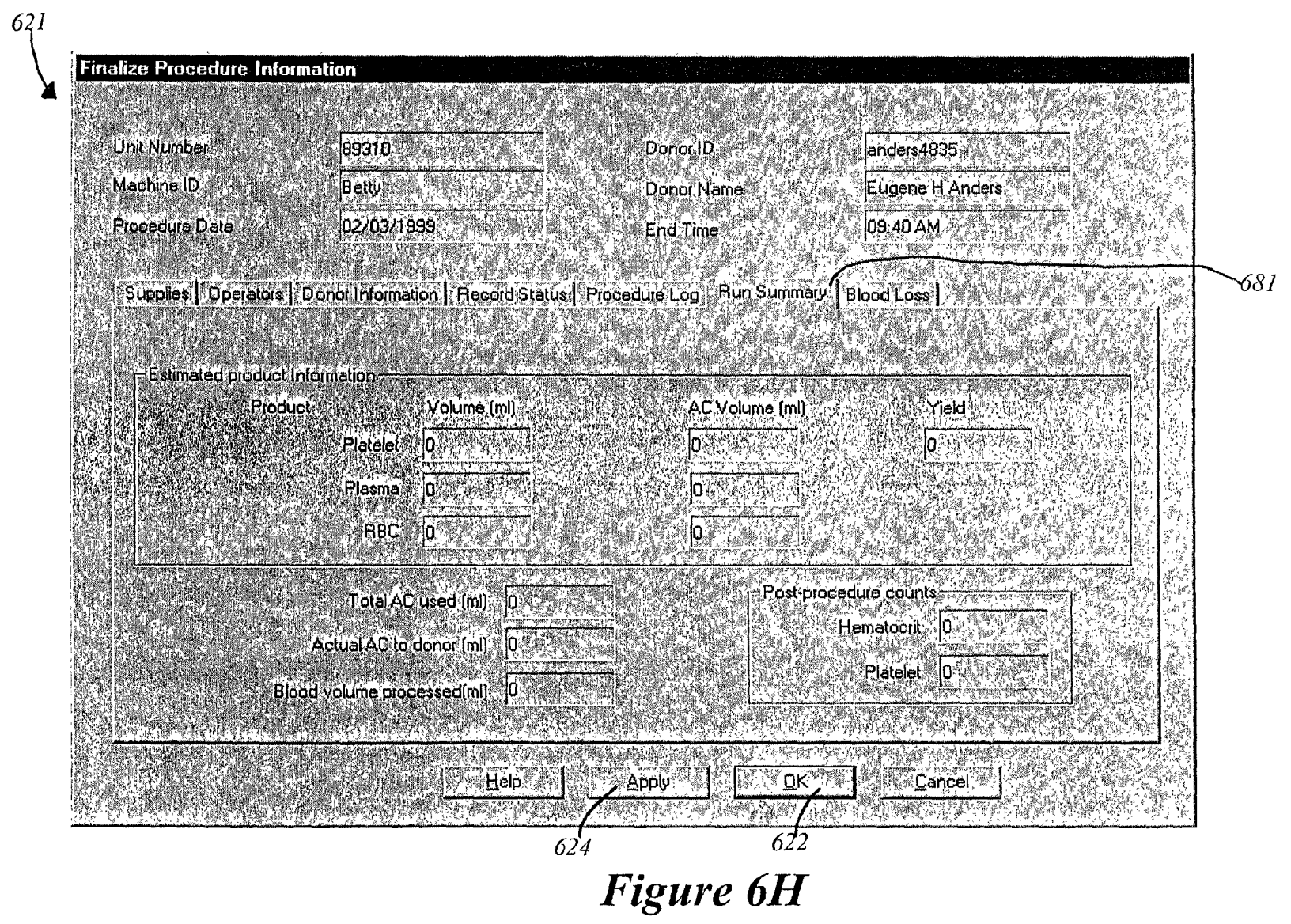
Figure 6I:
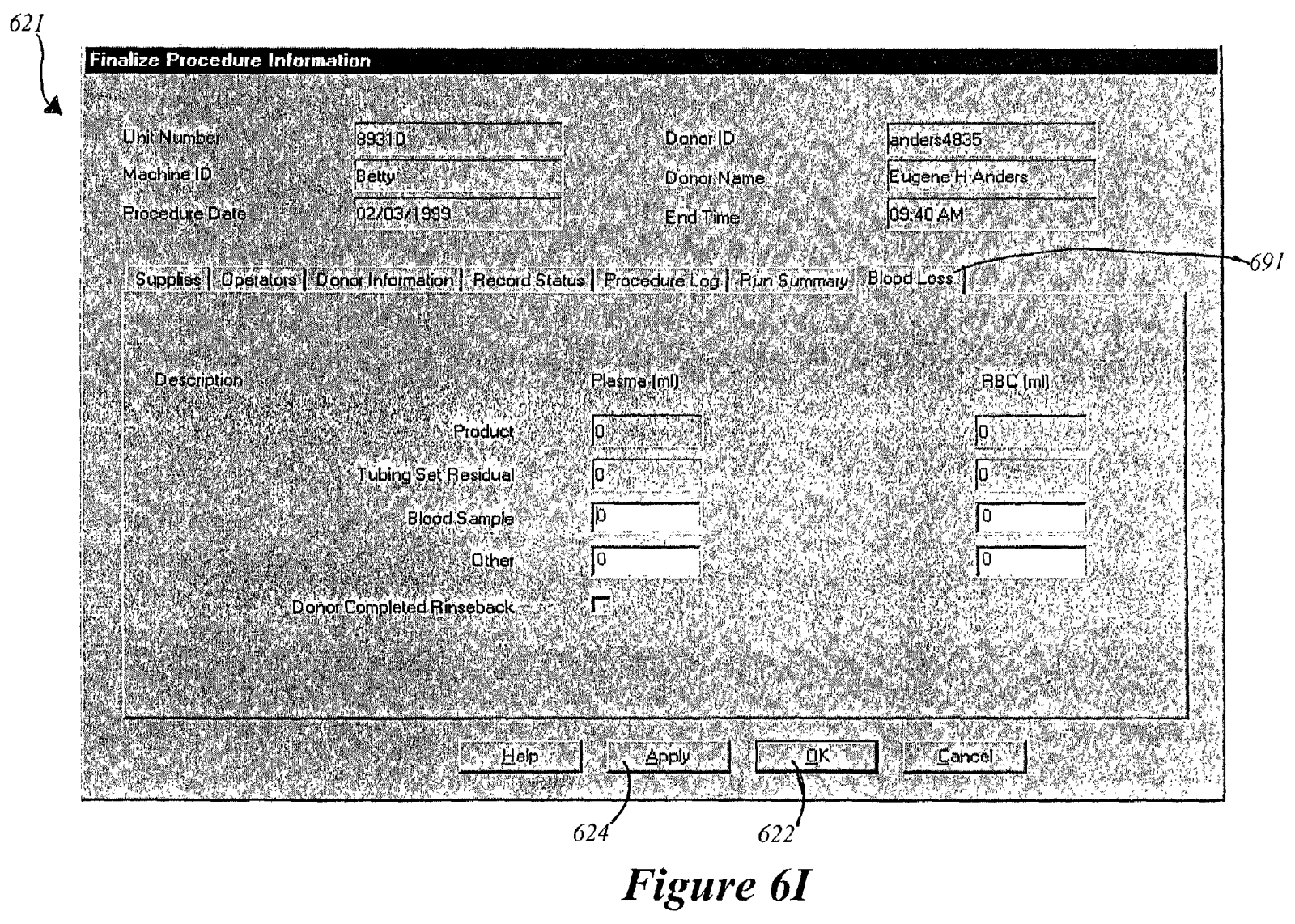
Figure 6J:
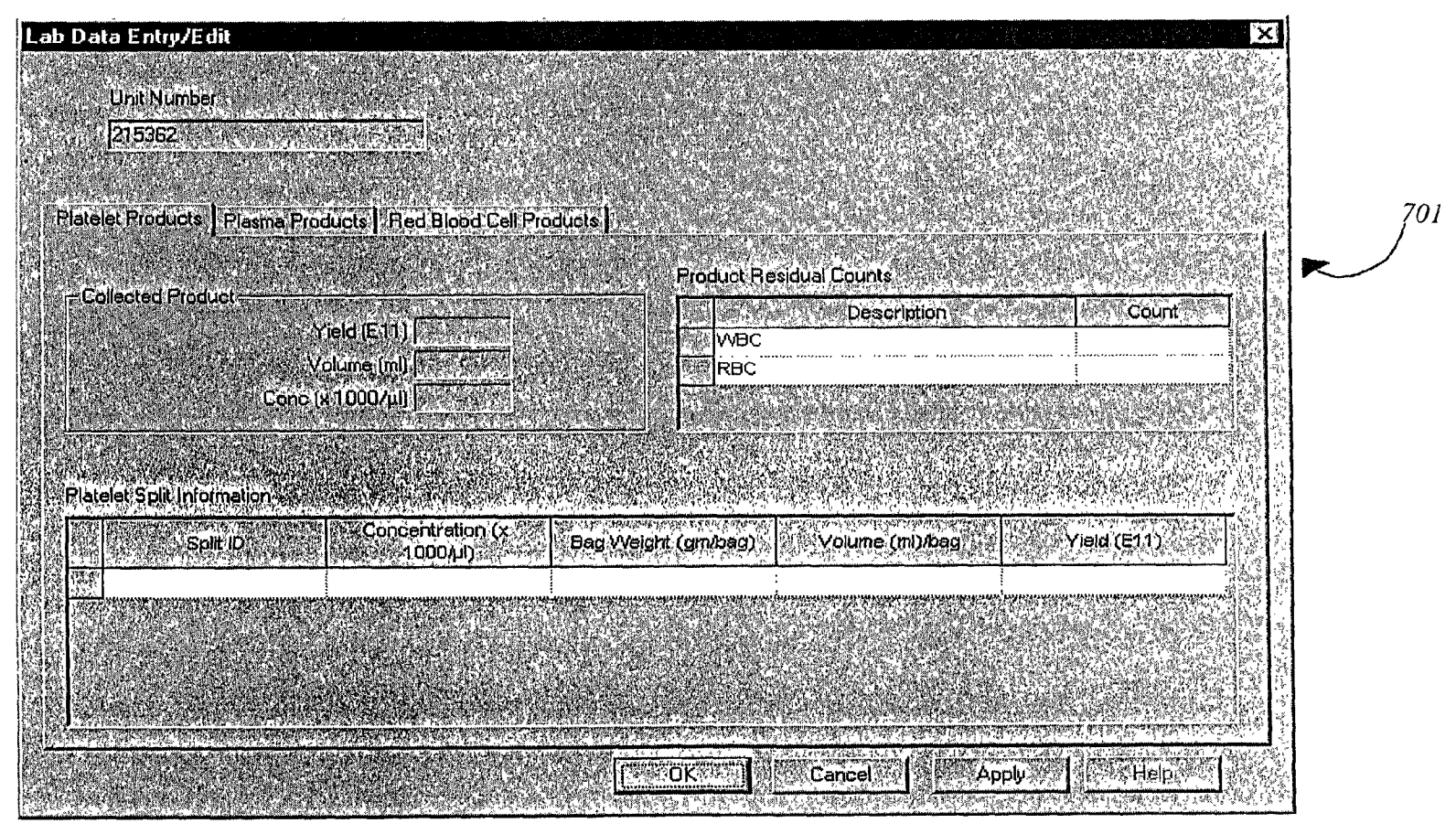

To finalize a procedure, the operator will preferably select a procedure listed in either the Monitor Procedure window 501 (FIG. 5A) or the Select Procedure task window 601 (FIG. 6A), and then open the Finalize Procedure Information dialog box 621 (FIGS. 6C–6I). The procedure record for the selected procedure is then displayed in the Finalize Procedure Information dialog box 621, preferably in initial form with a Supplies tab 631 as shown in FIG. 6C by default.

In the top portion 629 of the Finalize Procedure Information dialog box 621, the operator confirms all preferably required and pre-populated procedure information, as follows: Unit Number; Machine ID; Procedure Date; Donor ID; Donor Name; and End Time. All of the above information is preferably non-editable, and is preferably downloaded from the central database 142 and/or the apheresis system 10 run data for this procedure.

On the Supplies tab 631 (FIG. 6C), the operator may enter procedure supplies data. The supplies data entries may include the following: an "X" box or column, and various columns which may include a Description, a Lot number, an Expiration date, and a Manufacturer column, inter alia. In the "X" box/column, preferably the left-most column in the grid, the Administrator preferably defines which supplies entries are required, using an "X" in this cell for such required supply information. In the Description field, which is preferably non-editable as defined by an Administrator during setup, the Administrator preferably sets up supplies data by providing supplies descriptions and defining each supply as an optional or required entry. Each supply description the Administrator defines preferably appears in the Description column in the grid. The Lot number is preferably required if any supplies entry is a required entry. This can be typed into the box, or alternatively, the operator may use the barcode reader to enter this data automatically. The Expiration date is also preferably required if any supplies entry is a required entry. This also can be typed into the box, or alternatively, entered using a barcode reader to enter this data automatically. Similarly, the Manufacturer data is preferably required if any supplies entry is a required entry. Preferably a drop-down list, editable by selection only is used for entry here. Alternatively, the operator may use the barcode reader to enter this data automatically.

The operator may then optionally click the Operators tab 641 (see FIG. 6D) in the Procedure Data Entry/Edit screen 621 (also known as the Finalize Procedure Information screen 621; FIGS. 6C–6I) to access the operator role data entry area. Here, the operator may preferably enter information about operator roles. Each operator role entry may include the following: an "X" box or column; a Role column, and Operator ID and Name columns. The "X" box or column is again preferably the left-most column in the grid, with the Administrator having pre-defined an operator role entry as required such that an "X" appears in this cell for that role. The Role column is preferably non-editable, defined by the Administrator during system setup. The System Administrator preferably sets up operator roles data by providing operator role descriptions and defining each operator role as an optional or required entry. Each operator role description the Administrator defines appears in the Role column in the grid. The Operator ID and Name columns are preferably required if the operator role is a required entry. These may be drop-down lists, editable by selection only. When the operator selects an item in the Operator ID drop-down list, the corresponding Operator Name cell is preferably automatically populated with the operator's first and last names. Alternatively, an operator name can be typed in the box, but it reverts to match the currently-selected operator ID the next time the procedure record is displayed.

The operator may then optionally click the Donor Information tab 651 in screen 621 (FIG. 6E) to view the donor information for this procedure. The donor information is preferably supplied from the central donor database 142 and/or the blood bank information system, as well as information entered during the Prepare Procedure Wizard for this procedure. Once the central system 140 creates a procedure record for a procedure, the donor information becomes a part of the procedure record, providing a snapshot of this information on the date the procedure was run. This information is therefore preferably non-editable. The donor information preferably includes the following: Gender; Height; Weight; TBV (Total Blood Volume); Blood Type (if available); CMV and HLA status (if available); and Pre-procedure values for hematocrit and platelet count. In addition to the above information, this tab 651 preferably also shows the post-procedure values for hematocrit and platelet count. This information is preferably provided from the apheresis system 10 run data for this procedure and thus, like the other information in this tab, these values are preferably non-editable.

The operator may then also optionally click the Record Status tab 661 in screen 621 (FIG. 6F) to view the current central system procedure record status. The status options preferably update automatically during the procedure run and procedure record entry. The options, which are preferably non-editable within this module, may include the Procedure Record, the Machine Release, the Visit Status and the Reason. The Procedure Record preferably remains Opened until all required information has been entered in the procedure record; at that point, the central system may update this option to Closed. A check box can be used to indicate whether the machine has been released for the next donor. The Visit Status preferably shows the current status of the donor's visit (for example, if the procedure is currently running, this box shows the same status that is shown in the Monitor Procedure task window 501 (FIG. 5A) for this procedure). The Reason field may preferably be used to indicate whether and/or if the donor was removed from the Donor Assignment Queue 406 in the Assign Machine task window 401 (FIG. 4A) for any reason (incomplete procedure, dismissed at the apheresis system 10, etc.); the reason being displayed in this box.

The operator may then optionally click the Procedure Log tab 671 (see FIG. 6G) to view the procedure name and the procedure log (an event log of all machine alerts, alarms, warnings, and operator adjustments entered throughout the procedure). Procedure comments that have been entered by a system operator may be intermixed (according to timestamp) with the other information in this scrollable region. This information is preferably variable for active donations and remains at the final status display for pending and finalized procedures. The information is preferably non-editable and is preferably supplied by the apheresis machine 10 run data and by the operator entering procedure comments either in this dialog box 671 or via the Monitor Procedure task window 501 (FIG. 5A). The operator may optionally click the Comment button to enter a comment in the procedure record for that procedure. An Enter Procedure Comment dialog box (not shown) may be made to appear. The operator can select a comment from the pre-configured comment list (preferably created by the Administrator) and/or enter a free-form text comment entry. If the operator clicks the OK option, the Finalize Procedure Information dialog box 621, Procedure Log tab 671 is redisplayed, showing the date and time the comment was created, as well as the user ID for the user who was logged on when the comment was created. If the operator clicks Cancel, the Finalize Procedure Information dialog box 621, Procedure Log tab 671 is redisplayed, but the comment is not included in the procedure record.

The operator may then optionally click the Run Summary Tab 681 (FIG. 6H) to view the machine-estimated product volume information. This information is preferably provided by the apheresis machine 10 after the run is complete. Until the procedure is completed, all of the fields in this tab are blank. The information would then be non-editable and defaulted from the procedure run data (machine run summary). This information preferably includes the following: the estimated volume for platelet, plasma and RBC products; the AC volume in platelet, plasma and RBC products; the estimated yield for platelet products; the total AC volume used; the AC administered to the donor during the procedure; the total blood volume processed; and Summary remarks, preferably including one or more of the following: a reminder to label LRS platelet product as having less than 1×10e6 white blood cells (if so leukoreduced, as on the Trima® system 10; a reminder to count the product; a reminder to verify platelet yield; a reminder to verify platelet volume; a reminder to determine whether platelet concentration is out of range; a reminder to verify plasma volume; and/or a reminder to verify RBC product.

The operator may then optionally click the Blood Loss Tab 691 (FIG. 6I) to view blood loss entries. Blood loss information preferably includes the Product, the Tubing Set Residual, the Blood Sample and an Other column. A check box for Rinseback Completion is also provided. In more detail, the Product column shows product volume for plasma and RBCs. This information is preferably downloaded from the apheresis system 10 run data for this procedure, and is preferably non-editable. The information is determined based on the procedure that was run and the donor's hematocrit. Until the procedure is completed, these fields are blank. The Tubing Set Residual preferably shows the volume of plasma and RBCs remaining in the tubing set. This information is also preferably downloaded from the apheresis system run data for this procedure, and is preferably non-editable. During the procedure, this information is determined based on the collection status, the tubing set type, the procedure that is being run, and the donor's hematocrit. When the procedure is completed, this information is determined based on all of the above, as well as whether or not rinseback was completed for the procedure. The Blood Sample column presents the volume of blood, entered by operator for plasma and/or RBCs, according to the facility's SOPs. The default value if, used, is preferably specified by the Administrator. The Other column includes any Other volume of blood (for example, estimated volume of a spill), entered by operator for plasma and/or RBCs, according to the facility's SOPs. The Donor Completed Rinseback check box is checked if rinseback was completed for the procedure. Until the procedure is completed, this box remains unchecked. This information is also preferably downloaded from the apheresis system run data for this procedure, and is preferably non-editable.

After entering and/or confirming the above data (particularly as may be required by the SOP's of a particular blood center), the operator may then click the "OK" button 622 (FIGS. 6C–6I) to save the record. The central system 140 saves the procedure record. If all the required information has been entered, the central system 140 updates the status of the record to be closed. The central system 140 may then also close the Finalize Procedure Information dialog box 621 and redisplay either the Monitor Procedure task window 501 (FIG. 5A) or the Select Procedure task window 601 (FIG. 6A), depending on the method the operator originally used to open the Finalize Procedure Information dialog box 621.

Alternatively, the Operator may click the Apply button 624, at any point while the Finalize Procedure Information dialog box 621 is displayed to save the data in the procedure record up to that point, without closing the dialog box 621. The central system 140 saves the procedure record and, if all the required information has been entered, the system 140 updates the record's status to closed. Similarly, at any point while the Finalize Procedure Information dialog box 621 is displayed, the operator may click the Cancel button to cancel the current entry session. The central system 140 may then discard all unsaved changes in the procedure record, and close the Finalize Procedure Information dialog box 621 and redisplay either the Monitor Procedure task window 501 or the Select Procedure task window 601, depending on the method the operator used to open the Finalize Procedure Information dialog box 621.

Various alternative actions are also available. For example, the Operator may view a record for a procedure which has not yet begun. The central system 140 creates a procedure record as soon as the operator completes the Prepare Procedure Wizard for a procedure (see FIGS. 3B–3E). However, the procedure does not appear in the Monitor Procedure task window until the donor and procedure information is downloaded to the assigned apheresis system 10. Prior to that time, if the operator wants to view the procedure record, he/she can search for the procedure record using the Select Procedure task window 601. The operator may also view and/or edit information in the Finalize Procedure Information dialog box 621, as described here; i.e., at any point in the overall process, however, in most instances, doing so at before a process has begun or during the process would be premature.

However, Lab data entry/edit may also be performed from screen 601 (as introduced above) at any time in the overall process; generally after such data has been processed and returned from the Laboratory. Again, the Lab Data Entry/Edit screen 701 (FIG. 6J) is preferably accessed by selecting the Lab button 611 in screen 601 (FIG. 6A). Then, lab information may be entered/edited in screen 701 according to the product types (see the three tabs for Platelet Products, Plasma Products and Red Blood Cell Products). Then, Lab data entry/editing may be performed according to the information on hand. For example, Collected Product information can be entered/edited (although this information may be downloaded from the apheresis machine 10, and thus may be made non-enterable/non-editable, here); Residual Count information can be edited/edited (as may be applicable); and Split Product information may be entered/edited (Split ID numbers; concentrations, bag weights, volumes and/or yields, e.g.), here.

During use of the Select Procedure task window 601, the operator may click one of the column headings in a grid to sort the entries using different criteria. The first time the column heading is clicked, the entries are sorted in ascending alphanumeric order. Each subsequent click of the column heading results in the opposite alphanumeric order (ascending or descending).

Note, the Donor may be dismissed at the Machine 10 after the central system has initiated a record. In such a case, the central system 140 preferably automatically closes the procedure record if both of the following are true: The donor is assigned to an apheresis system, but then is dismissed using the apheresis system touch-screen display 199 before the procedure is begun; and, the operator does not assign the donor to a different machine 10, but instead removes the donor from the Donor Assignment Queue 406 in the Assign Machine task window 401 (See FIG. 4A). For more information, see the following alternative actions described relative to the "Assign Machine" sub-procedure relative to FIGS. 4A and 4B.

The central system may also detect an Incomplete Run, in which case, the system 140 preferably automatically closes the procedure record if both of the following are true: the donor is disconnected from the apheresis system 10 and the operator indicates on the machine that the run is incomplete, and the operator has completed all information necessary to finalize the procedure record. If the operator has not yet completed all information necessary to finalize the procedure record, the procedure record remains opened until such information has been entered, as described, above.

Note, throughout the descriptions of preferred options above, there are set forth a plurality of described instances of data/information preferably being communicated to and from the central system 140 from and to the apheresis system(s) 10. Nevertheless, it is understood that not all of these particular types of data or information may be used or captured or communicated by many available blood processing systems. Thus, it should be understood that all such instances in the above description are intended as the preferred embodiment, and that lesser direct communications and mere manual data transfer from and to a central system 140 and associated blood processing systems 10 are also intended within the scope of the present invention. Thus, for example, data may be manipulated and/or optimized on/in a central system 140, and the results of which may not be readily transferred to a blood processing system 10 (see perhaps systems 10B and/or 10C as shown in FIG. 1B, e.g.), and therefore the resulting manipulated and/or optimized data or information may have to be operator entered into such a system 10 for use thereby. Similarly, the results of the processing/collection procedure performed by a lesser compatible system (see again, perhaps systems 10B and/or 10C, e.g.) may not be automatically communicatable to the central system 140, but may be operator transferred (i.e., manually entered) upon procedure completion. Instances of preferably non-editable fields or data, as set forth above, would thus not be applicable here. Rather, such data fields would indeed be editable/enterable depending upon which type of blood processing system 10 were being used. A further similar process for data handling may be performed for whole blood collection systems (see e.g., the whole blood representation 10D in FIG. 1B), wherein a data communicating machine is often not used (at least not in the initial collection process; a needle connected to a receptacle/bag by a tube may be the collection device 10D). However, data/information may still be captured by manual data entry throughout the process, for example, from initial Reception and Screening through to Collection completion. Moreover, subsequent (or chair-side, or bed-side) processing may even be performed such as to separate the collected whole blood into components which may be desirably tracked in a central system 140. The data would rather only be manually entered, or perhaps even certain subsequent (or chair-side, or bed-side) processing machines may have data communication abilities so as to communicate with a central system 140. The quantity and/or quality of data would then only differ as to the type of procedure performed (e.g., whole blood separated into which components).

Figure 6K:
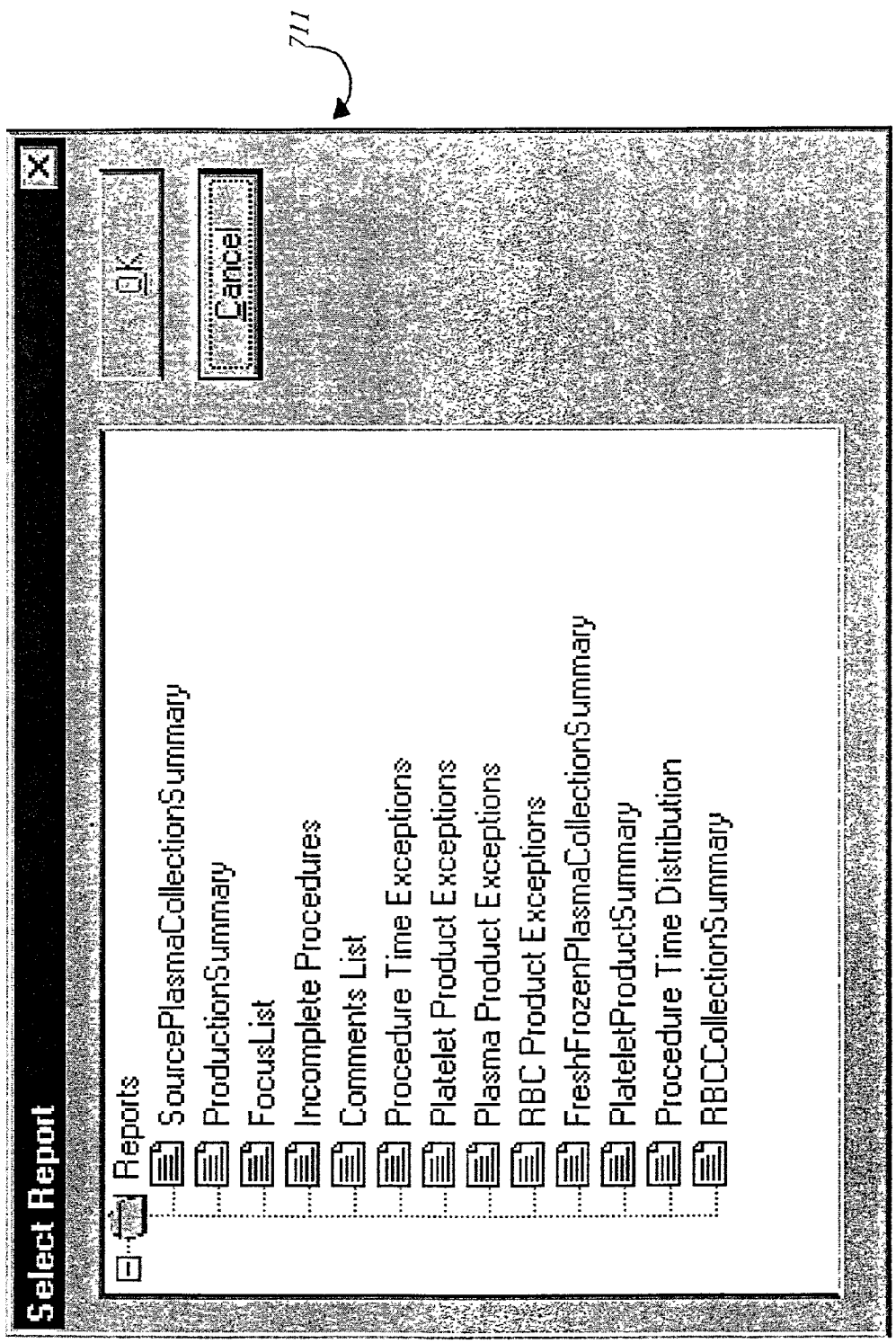
Figure 6L:
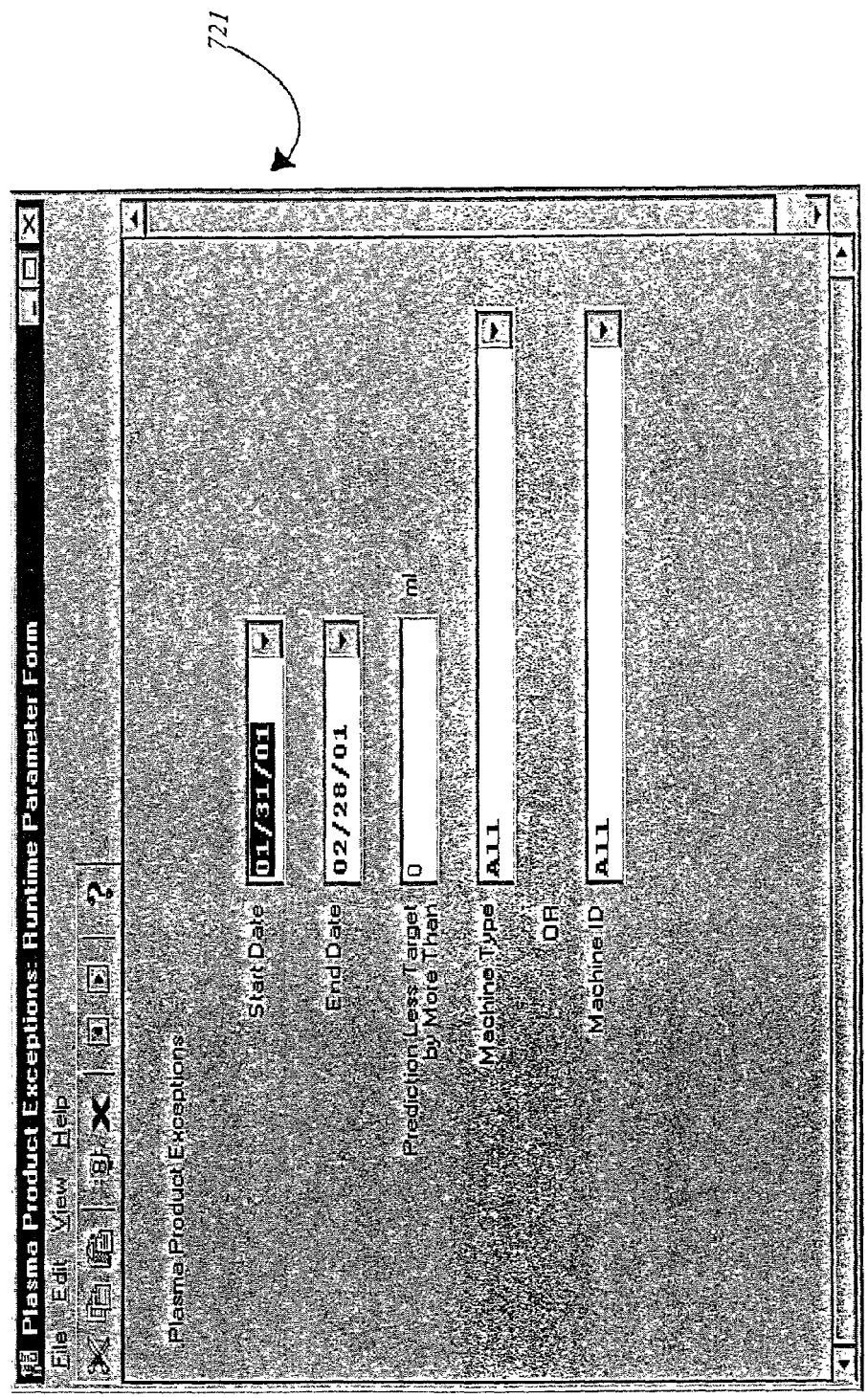

Lastly, if the operator desires to view and/or print an End-of-Run report when the procedure is complete, he/she may do so using the Reports feature of the Everest software (see generally FIGS. 6K, 6L and 6M, for example). Various pre-defined and/or system administrator defined reports are preferably generatable about donors, procedures and collected blood products, inter alia. The reports command may be an icon in the icon task bar 205 (though not shown as such here), or may be accessible through the Tasks menu 216 (see FIG. 2A, e.g.), inter alia. A list of previously configured reports may then be made to appear as for example is shown in dialog box 711 of FIG. 6K. Upon selection of a report from the list in box 711, a report generating dialog box such as box 721 (FIG. 6L) may then be made to appear. After entry of the prompted-for information, a report may then be generated. An example report is shown in the report previewer screen 731 (FIG. 6M). The presently preferred report generator is based on the Oracle® Reports platform which is a readily-available software application (from the Oracle Corporation, Redwood Shores, Calif.). Thus, data from the central may be transferred to such a Report generating platform to create reports of any desirable format in fashions known and understood by those skilled with Oracle® Reports or like software applications.

As mentioned throughout, an important element of the overall system 140 is the communication subsystem 146 which provides communication between and/or among the various other devices/elements. As described above, subsystem 146 may involve hardwire or cable connections between the various elements; and/or it may involve other devices and/or software. A further communication alternative with the computer/database 140 may generally involve the internet. As is known in the art, the internet provides a "common language" through which multiple different systems can communicate without requiring special tailoring of each system. For instance, various protocols have been established to facilitate data communication on what has become known as the internet. In particular, the TCP-IP (Transmission Control Protocol—Internet Protocol) is an internet protocol structure which was developed in a 1973 Department of Defense research project designed to link a "network of lowest bidders"; now in wide commercial usage since about 1988. In particular, the TCP ensures that the information goes to its destination correctly; verifies the correct delivery of data from client to server; and provides a common way of sharing information among different types of systems (PC, MAC, SUN workstation, etc.). Further, the IP also ensures the information goes to the right location; moves packets of information from node to node; and provides unique IP addresses assigned by InterNIC (NSF, AT&T, & Network Solutions, inter alia.). The Internet then provides a web of information which can be accessed through a single interface (web browser). The internet can also provide a communication medium between a computer/database system 140 and various other computer information systems such as those shown in FIG. 1B; and ostensibly provide communication protocols to or with the apheresis machines 10 as well.

As an example, as inventory is withdrawn or replenished within the hospital or blood bank, this information can be recorded via bar code. By connecting the information to the hospital information system (HIS) and on through to bloodaccess.com, or a like internet connection address, a blood donation center can then access and monitor local inventory levels. When one hospital needs a stat or immediate order for a given blood component, the blood center may then locate and arrange transfer of the units from one center or one hospital to another. The blood center can then replenish the units taken from the hospital within a short period of time (such as 24 hours) using flexible collection through automation. Moreover, this is not merely an inventory tool, it may also be tailored to fill specific needs such as in the "dosing" model introduced herein.

Similarly also, donor recruitment and/or eligibility and/or qualification can be run by a centralized system to determine which donors may be able to provide certain products at a certain time. The data may be obtained by data input as above, or with data already existing in the memory 142 and/or as may be obtained by communication with a discrete information system. Most preferably, these procedures could be performed without the specific potential donor present to predict what the donor could yield, and then if a desirable product is predicted (i.e., the potential donor is eligible or qualified to give the desired product(s)), the potential donor could then be contacted to recruit them to undergo the procedure. In this fashion, a blood center could better tailor its blood and blood component supply to better match demand.

Figure 7A:
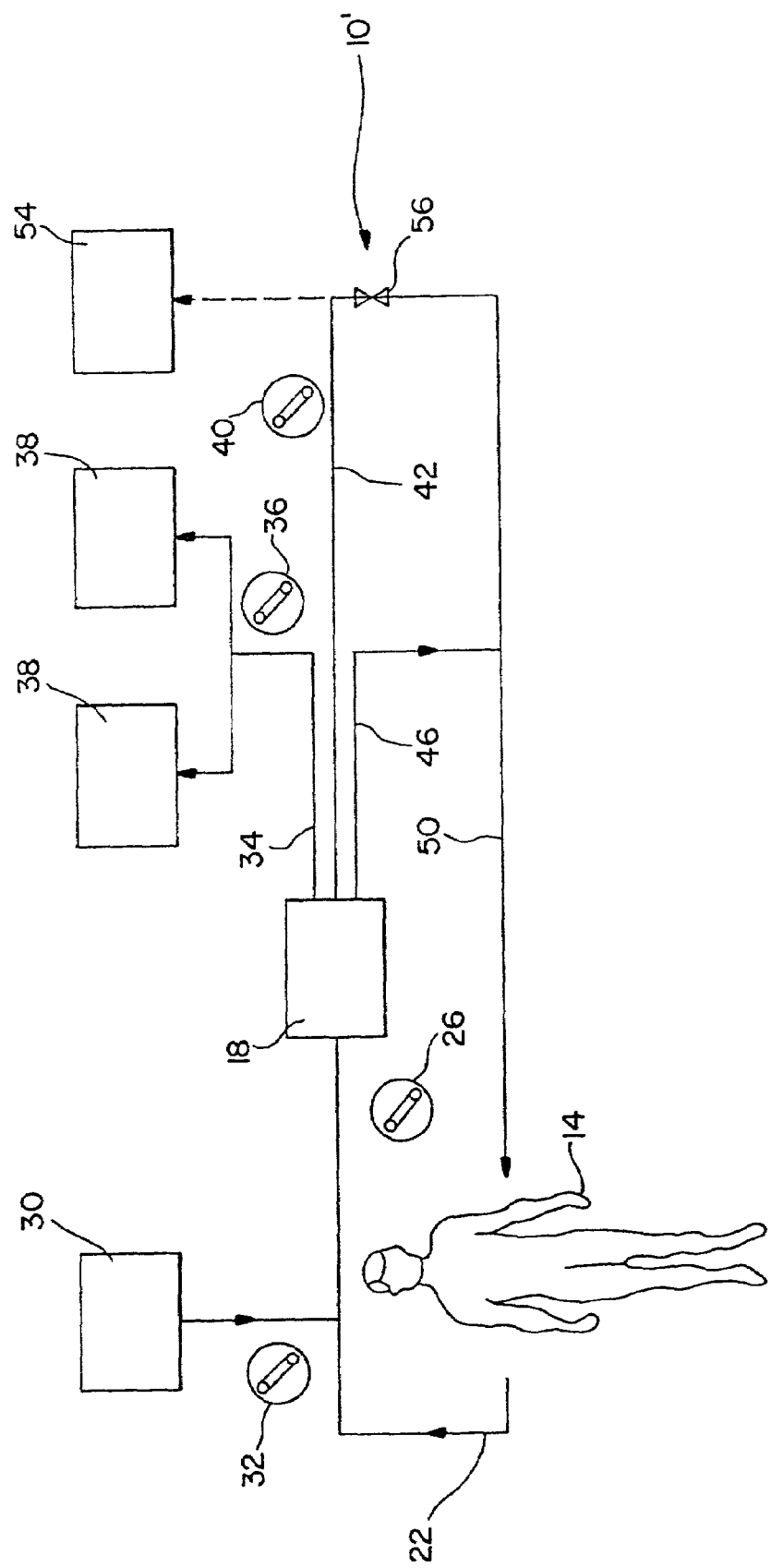
FIG. 7A is a schematic representation of one embodiment of a blood component separation assembly which utilizes a dual needle configuration and which may be incorporated into the blood component collection systems of FIGS. 1A–1D.

By way of background and provision of a detailed application of the present invention, a description of the blood apheresis process and associated machinery will now be set forth. Various embodiments of blood component collection assemblies may incorporate principles of the present invention. However, as noted above on-line techniques have been determined to be quite effective and thus the present invention is being described with reference to such techniques. One embodiment of an on-line technique and attendant apparatus which may be incorporated into the blood component collection system 2 of FIG. 1A is illustrated in FIG. 7A. An on-line technique herein refers to the use of a blood processing device which is controlled by parameters entered directly therein and calculated or manipulated thereby to achieve all necessary control parameters. Off-line techniques refer to the use of data entry and/or data manipulation performed by devices not resident on or within the particular blood processing device; though which are preferably disposed in data communication therewith.

The blood component collection assembly 10' of FIG. 7A utilizes an on-line technique in that a donor 14 (e.g., the whole blood source) is directly integrated with the system 10' by fluid interconnection with the blood component collection device 18. This particular on-line technique is more particularly referred to as a dual needle configuration since there are two fluid interconnections between the donor 14 and the blood component collection device 18.

The donor 14 is fluidly connected to the blood component collection device 18 by an inlet line 22 and appropriate needle assembly (not shown). Whole blood from the donor 14 is thus continuously provided to the blood component collection device 18 through the inlet line 22 for separation of the desired blood component(s) therefrom, utilizing an inlet pump 26 (e.g., a peristaltic pump) to maintain this flow if desired/required. Prior to the blood of the donor 14 entering the blood component collection device 18, anticoagulant from an anticoagulant ("AC") container 30 may be provided to the whole blood, utilizing an AC pump 32 (e.g., a peristaltic pump) to maintain this particular flow if desired/ required. Consequently, the inlet flow to the blood component collection device 18 typically includes both a flow of whole blood from the donor 14 and a flow of anticoagulant from the AC container 30.

The blood component collection device 18 separates the whole blood provided on-line by the donor 14 into three primary constituents, namely platelets, a combination of red and white blood cells ("RBC/WBC"), and plasma. The platelets collected from the blood component device 18 are directed through a platelet collect line(s) 34 to one or more platelet collect bags 38 via a collect pump 36. The plasma and RBC/WBC are provided back to the donor 14 through a plasma line 42 and RBC/WBC line 46, respectively, both of which are interconnected with a second needle assembly (not shown) on the donor 14 via a donor return line 50. The plasma line 42 includes a plasma pump 40 (e.g., a peristaltic pump) to maintain the flow of plasma if desired/required. Although plasma may be provided back to the donor 14 in the above manner, it may be desirable to collect the separated plasma in some cases. In this regard, a plasma collect bag 54 may be provided and interconnected with the plasma line 42 (interconnection shown in phantom). In this case, appropriate valving 56 may be incorporated in the plasma line 42.

Figure 7B:
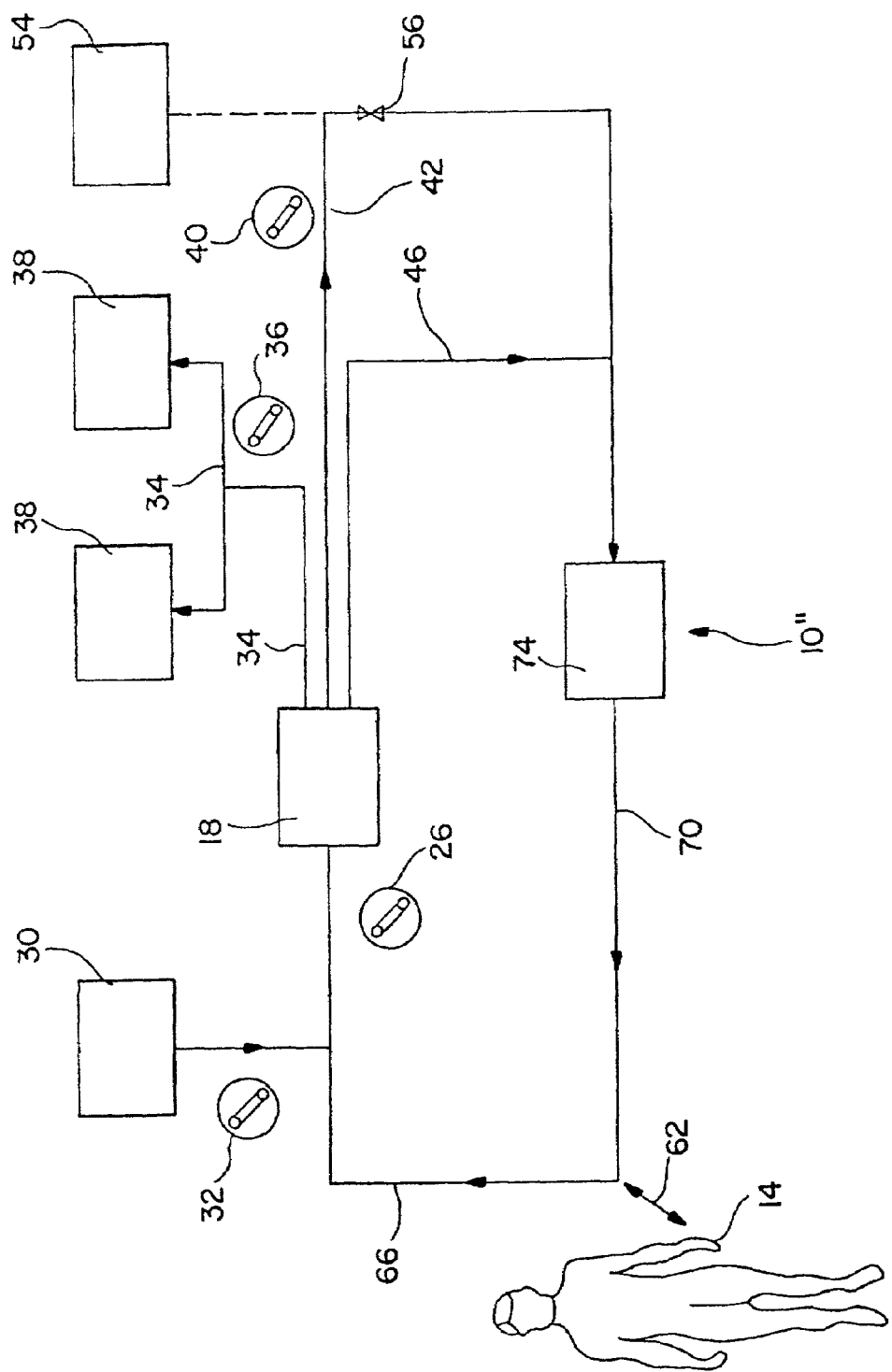
FIG. 7B is a schematic representation of one embodiment of a blood component separation assembly which utilizes a single needle configuration and which may be incorporated into the blood component collection systems of FIGS. 1A–1D.

The blood component separation assembly 10" of FIG. 7B is similar to that of the dual needle configuration of FIG. 7A except that a single needle assembly (not shown) integrates the donor 14 within the blood component collection assembly 10". Consequently, similar components are similarly identified where appropriate. With regard to the single needle configuration of FIG. 7B, whole blood of the donor 14 initially flows through a donor access line 62 and into an inlet line 66 which is fluidly connected with the blood component collection device 18 such that the platelets are separated and collected in the above-described manner. The plasma and RBC from the blood component collection device 18 flow through the plasma and RBC/WBC lines 42, 46, respectively, both of which are fluidly interconnected with a return flow controller 74. As above, however, the plasma may alternatively be directed to a plasma collect bag 54. In the event that plasma is not collected, the RBC/WBC and plasma are provided back to the donor 14 through the return flow controller 74 via a donor return line 70 which is interconnected with the donor access line 62. As can be appreciated, since only a single line is directly connected to the donor 14, namely the donor access line 62, blood is either being removed from or provided back to the donor 14 such that the procedure is effectively two-step versus continuous in relation to the donor 14.

Figure 8A:
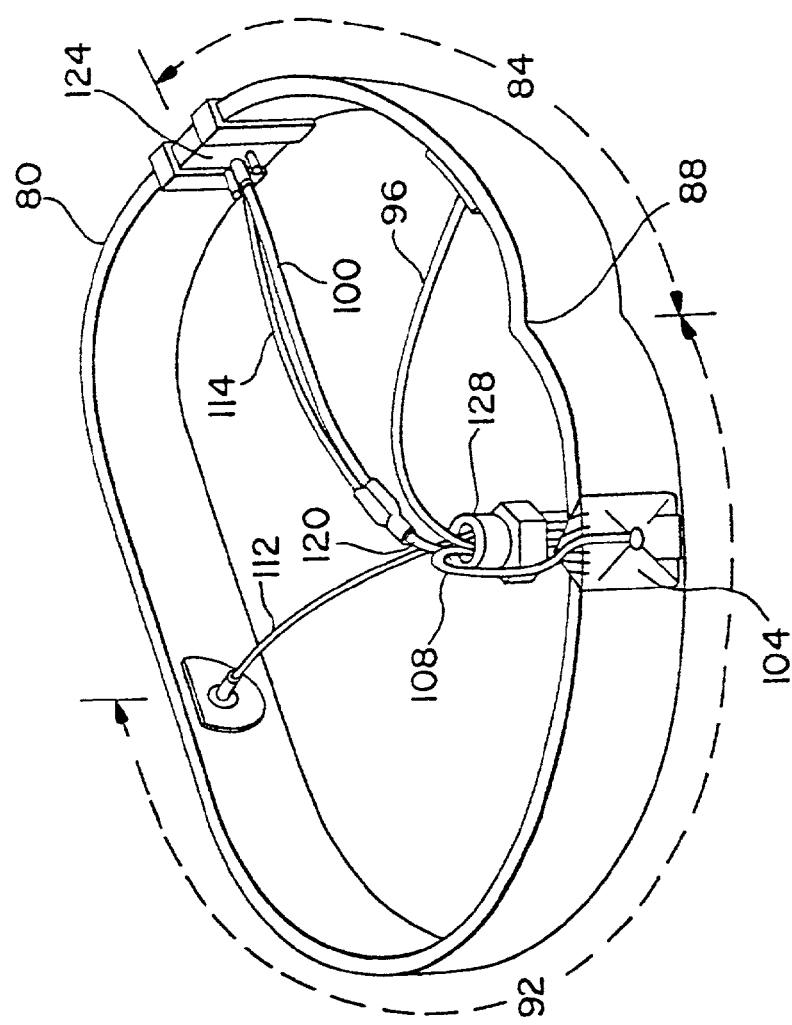
FIGS. 8A and 8B are isometric and top views, respectively, of one type of a disposable blood processing channel which may be used in the blood component collection device of FIGS. 7A and 7B.
Figure 8B:
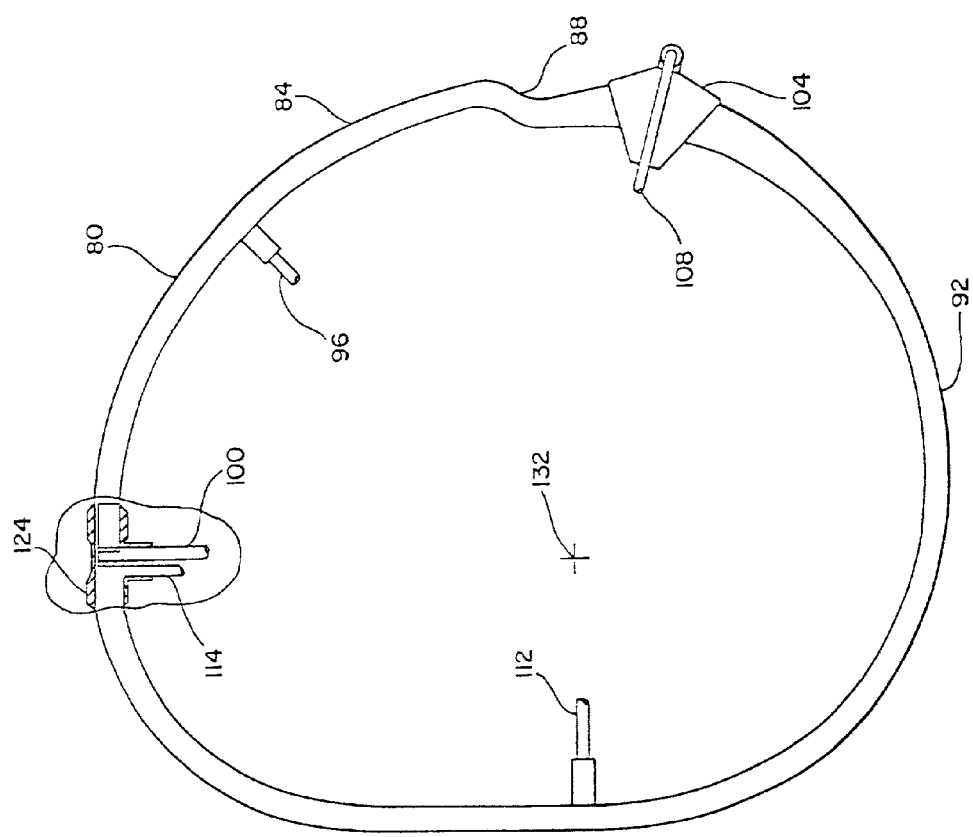

An exemplary blood component collection device 18 which may be used in the blood component collection assembly 10 is more particularly illustrated in FIGS. 8A–8B. This and like devices 18 are the subject of various U.S. Patents, see particularly U.S. Pat. No. 4,387,848 to Kellogg et al., entitled Centrifuge Assembly, issued Jun. 14, 1983, and U.S. Pat. No. 4,708,712 to Mulzet, entitled Continuous-loop Centrifugal Separator, issued Nov. 24, 1987; inter alia, the disclosures of which are incorporated by reference in entireties herein. Such devices 18 are also commercially available from the assignee of the present application as such may be incorporated in the COBE Spectra® and/or Trima® apheresis systems.

Referring to FIGS. 8A–8B, the blood component collection device 18 utilizes a processing channel 80 to provide the desired disposable extracorporeal circuit. The channel 80 is positioned preferably within a groove formed directly or indirectly in a centrifuge rotor (not shown) (e.g., a separate filler may receive the channel 80 and be attached to the centrifuge rotor), and is illustrated in the two-stage shape which it assumes during processing (i.e., during flow of blood therethrough). Although a two-stage channel 80 is shown and described further herein, the present invention is not so limited; rather, the present invention may be used also with single-stage and/or any other centrifugal configuration as well as with non-centrifugal separation machines or devices.

As shown and described herein, the two-stage processing channel 80 generally includes a first stage 84 for collectively separating red blood cells ("RBC") and white blood cells ("WBC") from platelet-rich plasma, a second stage 92 for thereafter separating platelets from the platelet-rich plasma, a transition portion 88 defining a separation between the first stage 84 and second stage 92, and a control chamber 124 for maintaining a proper interface between the first stage 84 and second stage 92, namely the position of the interface between the RBC/WBC and platelet-rich plasma within the transition portion 88.

The first stage 84 extends from one end of the control chamber 124 along an arcuate path generally inwardly, toward the axis 132 about which the processing channel 80 rotates via the centrifuge rotor, until terminating at the transition portion 88. Specifically, the end of the first stage 84 adjacent the control chamber 124 is positioned at a greater radial distance from the axis 132 than the end of the first stage 84 adjacent the transition portion 88. An inlet tube 96 is fluidly connected with the first stage 84 between its two ends to introduce whole blood into the processing channel 80 and a RBC/WBC tube 100 is provided in the control chamber 124 for removing the separated RBC/WBC from the channel 80. Both the inlet tube 96 and RBC/WBC tube 100 extend externally of the rotatable device 18 for interconnection with the donor 14 and/or collection bags 38, 54.

As RBC/WBC sediment against the outer wall in the first stage 84 during rotation of the centrifuge rotor they are directed and counterflow toward the RBC/WBC tube 100 for removal from the channel 80 due to the increased centrifugal forces at the RBC/WBC tube 100 in comparison with the transition portion 88. That is, since the first stage 84 extends along an arcuate path generally outwardly away from the axis 132 proceeding from the transition portion 88 to the control chamber 124, the centrifugal force differential along the first stage 84 establishes the described counterflow of the separated RBC/WBC. Moreover, the transition portion 88 also assists in providing for this counterflow since it extends along an arcuate path generally inwardly toward the axis 132 proceeding from the first stage 84 to the second stage 92.

The platelet-rich plasma, which has a lower density than the RBC and WBC, flows beyond the transition portion 88 from the first stage 84 into the second stage 92 for further processing, while the RBC/WBC are directed back toward the RBC/WBC tube 100 in the above-described manner. The second stage 92 initiates at the radially inwardmost part of the transition portion 88 and extends along an arcuate path generally outwardly away from the axis 132 to a platelet collection chamber 104. Platelets are removed from the processing channel 80 at the platelet collection chamber 104 by a platelet tube 108 which interfaces with the outer wall of the processing channel 80 at the platelet collection chamber 104. Thereafter, the second stage 92 extends along an arcuate path generally inwardly toward the axis 132 until terminating at the plasma tube 112. Both the platelet tube 108 and plasma tube 112 extend externally of the rotatable device 18 for interconnection with the platelet collect bag(s) 38 and donor 14/plasma collect bag(s) 54, respectively.

Platelets which do not separate from the plasma in the initial portion of the second stage 92 between the transition portion 88 and platelet collection chamber 104 are separated in the portion of the second stage 92 between the platelet collection chamber 104 and the plasma tube 112. These platelets will flow back towards the platelet collection chamber 104 in the opposite direction of the flow of platelet-rich plasma/platelet-poor plasma through the second stage 92 due to the configuration of this portion of the second stage 92. That is, the platelet collection chamber 104 assumes the radially outwardmost position in the second stage 92 such that all platelets, regardless of where separation occurs in the second stage 92, flow towards the platelet collection chamber 104 for removal from the channel 80.

Platelet-poor plasma exits the second stage 92 and flows out through the plasma tube 112 which interfaces with the inner wall of the processing channel 80 and/or continues to flow through the remaining portion of the processing channel 80 to the control chamber 124. Plasma which flows to the control chamber 124 exits the channel through the control tube 114 which joins with the RBC/WBC tube 100 into a single outlet tube 120. The positionings and diameters of the RBC/WBC tube 100 and control tube 114 and the joinder of such into the common outlet tube 120 regulate the position of the RBC/WBC-platelet-rich plasma interface within the transition portion 88 using conservation of mass principles.

As noted above, each blood component collection device 18 may include a prediction model appropriately interfaced with the operator input module 16 and/or disposed on or within the manipulation device 144 or in an associated memory device 142 as shown in FIGS. 1A–1D any and/or all of which may be used to configure the prediction model and/or to allow operator input of various parameters to be used by the prediction model for predicting a yield of a particular blood component to be collected before a collection procedure is initiated using a compilation of algorithms. The preferred prediction model and the optimization algorithms which are associated with the present invention are described in detail in U.S. Pat. Nos. 5,496,265; 5,658,240; 5,712,798; and 5,970,423; inter alia, all of which being commonly assigned to the assignee of the present invention, the disclosures of which being incorporated herein in their entireties as if fully set forth here by this reference thereto. The algorithms and disclosures thereof will thus be only briefly described herein.

The prediction model is typically configured by the site (e.g., the blood bank/center) for a particular blood processing or component collection procedure (e.g., single or dual needle) used by the site. Both single-needle and double needle procedures as shown in FIGS. 7A and 7B will be used in the following general description, particularly in relation to a platelet-collecting procedure (although of course, any collection procedure can be understood as being substitutable herein). In this regard, an AC infusion rate (i.e., the rate at which anticoagulant is provided to the donor 14 per the blood volume of the donor 14) and the AC ratio (i.e., the collective flow of AC and blood through the inlet line 22 in relation to the flow of AC through the line 22) must be specified (through configuration or modified input as will be discussed below). Moreover, in the event that plasma is to be collected into the plasma collect bag 54 in the collection procedure, the maximum amount of plasma which should be collected considering the medical and physical characteristics of the donor 14 must also be provided.

And, as described in the above-mentioned patents, there are two alternatives for establishing the plasma volume limit. These will not therefore be described further here.

Further information is required by the prediction model prior to performing its yield prediction function. For instance, the total procedure time is typically input by the operator or pre-configured by the site (e.g., the blood bank/center). Moreover, the total procedure time may be affected by whether a stepdown option is utilized for the blood component collection device 18 so as to enhance separation of the various blood components. When this stepdown option is selected, the angular velocity of the blood component collection device 18 is incrementally reduced during the platelet-collection procedure. For instance, the stepdown option could provide for angular velocities for the device 18 of 2400, 2200, and 2000 RPM, each of which would be for a specified duration.

Based upon the foregoing, the configuration of the prediction model in relation to the blood component separation assembly 10' and associated protocol in effect standardizes site protocol for purposes of "normal" operations. However, for a particular donor 14 it may be desirable to alter the "configuration" for one processing run. Consequently, the prediction model may utilize a procedure in which certain parameters utilized in the following equations may be adjusted on a one-at-a-time basis. Such is referred to as modified input data and the associated parameters are procedure time, inlet flow rate to the device 18, AC ratio option, the desired platelet collect volume, the desired platelet collect concentration, and the desired source plasma volume to be collected. Moreover, other parameters such as AC infusion rate, stepdown option (yes or no), needle option (single or double), and high flow option (yes or no) may also be entered as modified input data by an operator.

Having configured the prediction model in the above-described manner, the following additional information is provided and is utilized in the various calculations of exemplary Equations 1–22 presented below: (1) needle option, namely whether the procedure is dual needle (FIG. 7A) or single needle (FIG. 7B); (2) run identification number for purposes of associating the data/output generated by the various equations with a particular donor 14 and processing run; (3) the gender of the donor 14; (4) the height of the donor 14; (5) the weight of the donor 14; (6) the total blood volume as calculated in Eq. 10 below; (7) the hematocrit of the donor 14, either based upon an initial estimation and thereafter updated based upon analysis of the donor's 14 blood sample (e.g., by a cell counter) or input directly from such an analysis; (8) the platelet pre-count, either based upon an initial estimation and thereafter updated based upon analysis of the donor's 14 blood sample (e.g., cell counter) or input directly from such an analysis; and (9) whether plasma collection is desired in conjunction with the platelet collection.

Based upon the above initial configuration and subsequent data input (except when entered as modified input data), the following output is generated by the prediction model: (1) platelet yield; (2) inlet flow rate; (3) AC ratio; (4) procedure time; (5) platelet collect volume; (6) platelet collect concentration; (7) source plasma volume; (8) AC in the platelet and plasma collect bags 38, 54; (9) platelet post-count; (10) AC infusion rate; and (11) output approval. This information is utilized at least in part in the following equations to generate, inter alia, the predicted platelet yield value of the collected platelets for the case of the dual needle procedure of FIG. 7A and also for the case of the single needle procedure of FIG. 7B. The differences between those procedures with regard to the prediction model are identified herein. As will be appreciated, some of the equations are utilized in the calculation of the predicted platelet yield, whereas other equations are used to generate additional information for output and informational purposes. The variables or parameters and the units associated therewith of the equations are presented after the equations in the Variables Index.

Platelet Yield:

$$Y = 1 \times 10^6 C_{PR} V_B F_Y [1 - \exp[-E_c(f_{BP} - 0.12)]] \quad \text{(Eq. 1)}$$

where:

$$f_{BP} = (Q_{IN} t_E + 50)(1 - 1/R)/V_B \quad \text{(Eq. 2)}$$

and where:

$$Q_{IN} = R Q_{AC} = 0.001 I V_B P R \leq 150 \quad \text{(Eq. 3)}$$

Alternatively, the platelet yield may be expressed as:

$$Y = 1 \times 10^6 C_{PR} V_B F_Y [1 - \exp[-E_c(0.001 I (R-1) P t_E + 50(1 - 1/R))/V_B - 0.12]] \geq 0 \quad \text{(Eq. 4)}$$

Platelet Collection Efficiency:

$$E_c = C_1 - C_2 \exp[9.91(1 - 1/R) H] Q_{INA} \geq 0 \quad \text{(Eq. 5)}$$

where the constant $C_1$ is defined as follows:
$C_1 = 0.803$—dual needle, without stepdown
$C_1 = 0.840$—dual needle, with stepdown where the constant $C_2$ is defined as follows:
$C_2 = 4.08 \times 10^{-5}$—dual needle, without stepdown
—dual needle, with stepdown and where:

$$Q_{INA} = Q_{IN}(t_E/t_P) \quad \text{(Eq. 6)}$$

In Eq. 6, $t_P$ may be provided as configuration data or modified data as provided above, or alternatively may be derived from the solution of Eq. 4 for $t_E$.

Effective Procedure Time:

$$t_E = t_P, \ Q_{IN} \leq 45 = t_P - 500(1/45 - 1/Q_{IN}), \ Q_{IN} > 45 \quad \text{(Eq. 7)}$$

Only high-flow protocol is used for $Q_{IN} > 45$.

AC Infusion Rate Constant:

$$I = 1000 Q_{IN}/(P R V_B) \quad \text{(Eq. 8)}$$

Alternatively to the use of Eq. 8 for the derivation of the AC infusion rate constant I, such may be provided as configuration or modified input data pursuant to the above.

AC Ratio:

Initially, the AC ratio may be provided as configuration or modified input data pursuant to the above. In configuration, it is defined as follows:

$$R = 1 + 2.51/H \ \text{low} = 1.33(1 + 2.51/H) \ \text{medium} = 1.67(1 + 2.51/H) \ \text{high} \quad \text{(Eq. 9)}$$

Total Blood Volume:

$$V_B = 604 + 0.006012 \ L^3 + 14.6 \ W \ \text{ml (male)} = 183 + 0.005835 \ L^3 + 15.0 \ W \ \text{ml (female)} \quad \text{(Eq. 10)}$$

Plasma Collect Factor:

AC infusion rate control maintains the AC flow to the donor as:

$$Q_{ACD} = 0.001 \ IV_B \quad \text{(Eq. 11)}$$

where the inlet flow associated with this is:

$$Q_{INO} = R Q_{ACD} = 0.001 \ IRV_B \quad \text{(Eq. 12)}$$

$Q_{IN}$ is proportional to the total AC flow, as given by Eq. 3, which includes the AC that flows to the platelet collect bag 38 and the plasma collect bag 54. P (Eq. 13) is the factor by which $Q_{IN}$ is increased by collecting AC, relative to not collecting AC. That is, $$P = Q_{IN}/Q_{INO} = (\text{average } Q_{AC})/Q_{ACD} \quad \text{(Eq. 13)}$$

where:

$$P = 1 + (f_{ACP}/Q_{ACD})[V_C/(t_P - 150/Q_{IN}) + V_{SP}/(t_P - 500/Q_{IN})] \quad \text{(Eq. 14)}$$

and where:

$$f_{ACP} = [(R-1)(1-H)]^{-1} \quad \text{(Eq. 15)}$$

Platelet Collect Volume:

$$V_C = 1 \times 10^{-6} Y/[C_B(1 + f_{ACP})] \quad \text{(Eq. 16)}$$

Source Plasma Volume:
The four choices provided are as follows:

$$\left. \begin{array}{l} V_{SP} = 0 \\ = V_{CON} - V_C \\ = f_{SP} V_B - V_C \\ = \text{specified as modified input} \end{array} \right\} \geq 0 \quad \text{(Eq. 17)}$$

where:

$$V_{CON} = V_{CONL}, \ W < W_C = V_{CONH}, \ W \geq W_C \quad \text{(Eq. 18)}$$

and where:

$$0.01 \leq f_{SP} \leq 0.15 \quad (Eq.\ 19)$$

Donor Post-count:

$$C_{PO}=C_{PR}\exp[-E_C(0.001I(R-1)Pt_E+50(1-1/R)/V_B-0.12)] \leq C_{PR} \quad (Eq.\ 20)$$

A warning is given if $C_{PO}<100$.

Collect Volumes:

$$V_{CB}=V_C(1+f_{ACP}) \quad (Eq.\ 21)$$

$$V_{SPB}=V_{SP}(1+f_{ACP}) \quad (Eq.\ 22)$$

The primary equation to be solved for purposes of the yield prediction by the prediction model is Eq. 4. Consequently, Eqs. 1–3 and 5–22 are ancillary to Eq. 4 although they may be used to calculate other output data and/or information required by Eq. 4. With regard to the manner in which Eqs. 1–22 are solved, all the iteration loops are preferably based on the technique of successive approximation, in which each iteration is a repeat of the previous one, but using updated parameter values calculated in the previous iteration. This process continues until all the convergence criteria are met. The convergence criteria are that, on successive iterations, the variable difference is $\leq 1$ for $V_c$, $\leq 0.2$ for $t_E$, and $\leq 10$ for $C_B$.

As noted above, the foregoing was based upon a dual needle configuration as illustrated in FIG. 7A. In the event that a single needle configuration such as that illustrated in FIG. 7B is utilized, the following Eq. 7' is used in place of Eq. 7 and the constants $C_1$ and $C_2$ for Eq. 5 are as follows:

$$C_1=0.803$$

$$C_2=8.54\times 10-5$$

$$=t_E=t_P,\ Q_{IN}\leq 20=t_P-215(1/20-1/Q_{IN}),\ Q_{IN}>20 \quad (eq.\ 7')$$

Variables Index

Symbols for Equations:

$C_1$, $C_2$=constants in platelet collection efficiency equations $C_B$=platelet concentration in collect bag, expressed as $10^3$ platelets/microliter $C_{PO}$=donor post-count, expressed as $10^3$ platelets/microliter CPR=donor pre-count, expressed as 103 platelets/microliter EC=platelet collection efficiency fACP=AC expressed as a fraction of pure plasma volume fBP=fraction of VB processed in platelet collection procedure fSP=VCON expressed as a fraction of VB FY=user-specific (e.g., blood bank/center) yield calibration factor H=hematocrit of donor or patient I=AC infusion rate constant L=donor or patient height, inches P=plasma collect factor QAC=AC flow, ml/min QACD=AC flow infused into donor for platelet collection procedures, ml/min QIN=inlet flow, ml/min QINA=average inlet flow for platelet procedures, ml/min QINO=RQACD=inlet flow associated with QACD, ml/min AC=ratio tE=equivalent procedure time, min tP=procedure time, min VB=total blood volume of donor or patient, ml V=volume of pure plasma in platelet collect bag, ml VCB=total volume in platelet collect bag, ml VCON=volume constraint for total pure plasma collected, ml VCONH=higher value of VCON, ml VCONL=lower value of VCON, ml VSP=volume of pure plasma in source plasma bag, ml VSPB=total volume in source plasma bag, ml W=donor or patient weight, lbs WC=weight constraint associated with VCON, lb Y=platelet yield, number of platelets.

As noted above, the computer/database assembly 140 associated with principles of the present invention interfaces with or at least provides information to one or more blood component collection assemblies 10 to provide a blood component collection system 2. That is, although there are definite advantages to having an interface between the computer/database assembly 140, and the blood component collection device 18, the optimization procedure may be performed at any location and input into the blood component collection device 18 in any manner. Since the general principles of the blood component collection assembly 10 were described with relation to the collection assemblies 10', 10" (FIGS. 7A and 7B) which included the blood component collection device 18 and its various features, the computer/database assembly 140 will be described in relation to such assemblies 10', 10". However, it will be appreciated that the fundamental optimization principles of the present invention are not limited to these collection procedures and/or apparatus.

As noted (FIGS. 1A–1D), the computer/database assembly 140 generally includes a central station 148, as well as a manipulation device 144 and a memory device 142 (not separately shown). Initially, it should be noted that the manipulation device 144 is preferably separate from the internal control of the blood component collection device 18. Device 18 also preferably remains accessible by the operator interface device 16 (which could include the touch screen introduced above). However, typically the manipulation device 144 will be integrated with (e.g., put in data communication relationship with) this internal control device 16. The central memory device may also be separate from the central manipulation device 144 (as well as from the individual blood processing machines 10 and/or their control elements 16). The memory device need only be put in data communication relationship with the data manipulation device 144 and/or one or more control elements of the central computational/database assembly 140 and/or one or more blood processing machines 10.

Figure 9A:
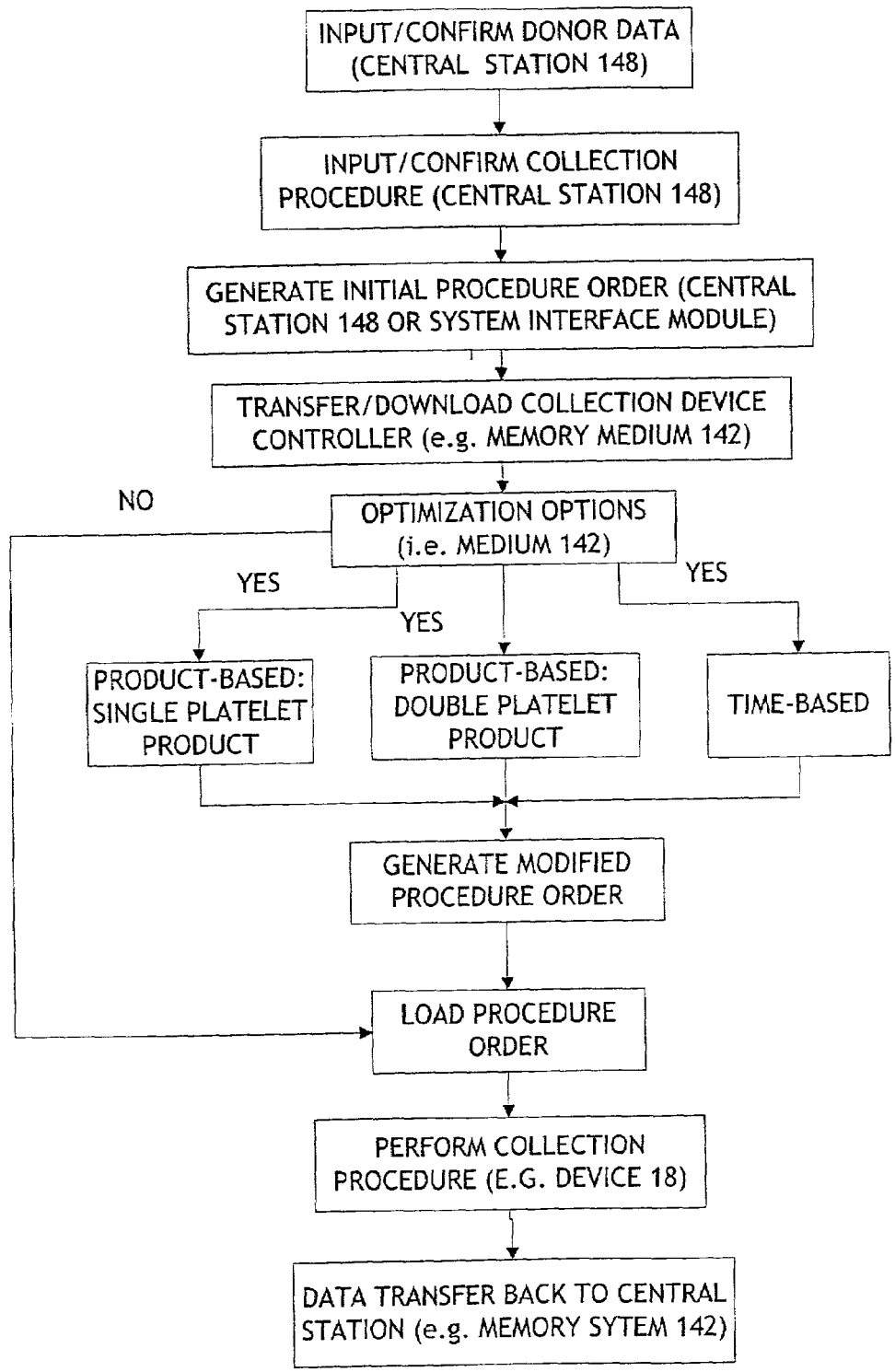
FIG. 9A is a flow chart of a blood component collection procedure utilizing principles of the present invention.

Referring now to FIG. 9A, the computational/database assembly 140 will be described with regard to a standard exemplary procedure. The central input station 148 will typically be used by blood banks/centers as the primary means for donor data input and donor data management. As introduced above in the relation to FIGS. 2A–2E, information relating to a donor such as gender, height, weight, total blood volume, blood type, temperature, pressure and demographics will preferably be input at the central input station 148, or could be easily downloaded to the computer/database assembly 140 from a disparate system such as systems 3 and/or 4 as shown in FIG. 1B. Moreover, information relating to the donor's hematocrit and a blood component pre-count (such as platelet pre-count), both of which may be obtained from a donor blood sample and determined by known techniques such as cell counters, may also be entered at the central station 148. In addition to donor-related data, the particular type of collection procedure to be used for the donor (e.g. single needle or double needle) may be input/confirmed at the central input station 148. These also could be downloaded from a disparate system. Based upon this information and certain site-standardized conditions (e.g., total procedure time, collection efficiency, AC infusion rate), an initial procedure order is thereafter generated preferably by the manipulation device 140 which specifies the various process control parameters associated with the selected collection procedure.

The initial procedure order may be transferred/downloaded onto the internal control of a blood component collection device 18 by a computer network system (FIGS. 1A and 1B) or by other methods such s floppy disk transfer (not shown). The operator interface module 16 may be used to assist this process if required/desired. When this operator interface module 16 exists, it may of course still be used as an alternative for the initial donor data input and/or to generate the initial procedure order including optimization and thereby alleviate the need for a central input station 148. However, it is believed that it will be more efficient to use the central input station 148 and the associated central data manipulation device 140, preferably in conjunction with the central memory database. Although this initial procedure order may be used in the collection process, the initial procedure order may also be optimized in accordance with principles of the present invention to obtain one or more optimal values for the process control parameters. This optimization may also be performed on the individual blood processing machines 18, but is preferably conducted on/by the central data manipulation device 140. As noted, this optimization process may be utilized before the collection procedure is actually initiated, but may also be initiated during a given collection procedure and such is referred to as downstream optimization although if performed after initiation, and though possibly performed at the central computer/database 140 on by manipulation device 140, it is preferred that post-initiation changes be effected only at or by the individual machines 10.

With regard to the various optimization options, process control parameters may be derived for a product-based optimization. More particularly, the computer/database assembly 140 and specifically the manipulation device 144 derives process control parameters for achieving a predetermined yield of blood components through a maximization of at least one process parameter as will be discussed below in relation to the optimization models 152 (FIG. 9B), and 172 (FIG. 9C), for example, as noted above, in the United States a single platelet product (SPP) is $3\times10^{11}$ platelets and a double platelet product (DPP) is $6\times10^{11}$ platelets. Consequently, the manipulation device 144 may be configured to provide a number of product-based optimizations such as SPP and DPP. Although the exact values for a current U.S. SPP and DPP could be configured into the manipulation device 144, in order to increase the probability that the actual yield will equal or exceed the yield requirements for a current U.S. SPP or a DPP, the site may configure a SPP to be 3.5×1011 platelets and a DPP to be 7.0×101 platelets (e.g., to effectively provide a given confidence level over the minimum that the specified yield will actually be met).

The manipulation device 144 may also be configured to provide a time-based optimization. That is, for a given amount of time which a donor is available, the manipulation device 144 will derive those process parameters which allow for the collection of a "maximum" amount of platelets in this time period in relation to a maximization of at least one of the process control parameters.

Once the optimization is complete, the values for the various process control parameters generated thereby, as well any ancillary/previously specified values, are downloaded to the internal control of the blood collection device 18 such that the collection procedure may be initiated or reinitiated (downstream optimization) as the case may be in accordance with these values. Once the procedure is completed, certain data is transferable (electronically through the communication subsystem 146 or otherwise as noted, e.g., floppy disk) back to the manipulation device 144 and/or the central memory/database and/or the central input station 148 for further use with regard to the particular donor. In addition, this information as well as the initial input may be used to generate various types of reports which may further assist in the management of the blood bank/center (e.g., individual run, donor/patient, summary reports, etc.). That is, this information may be used in the derivation of subsequent procedure orders for the particular donor or even for improved efficiency for entire pool of donors. For instance, in the event that a certain AC infusion rate was used in the collection procedure which had certain effects on this particular donor, this may be recorded in the central memory/database 142 such that a lower AC infusion rate would be suggested/required for subsequent donations by this donor and perhaps also for the entire pool.

Figure 9B:
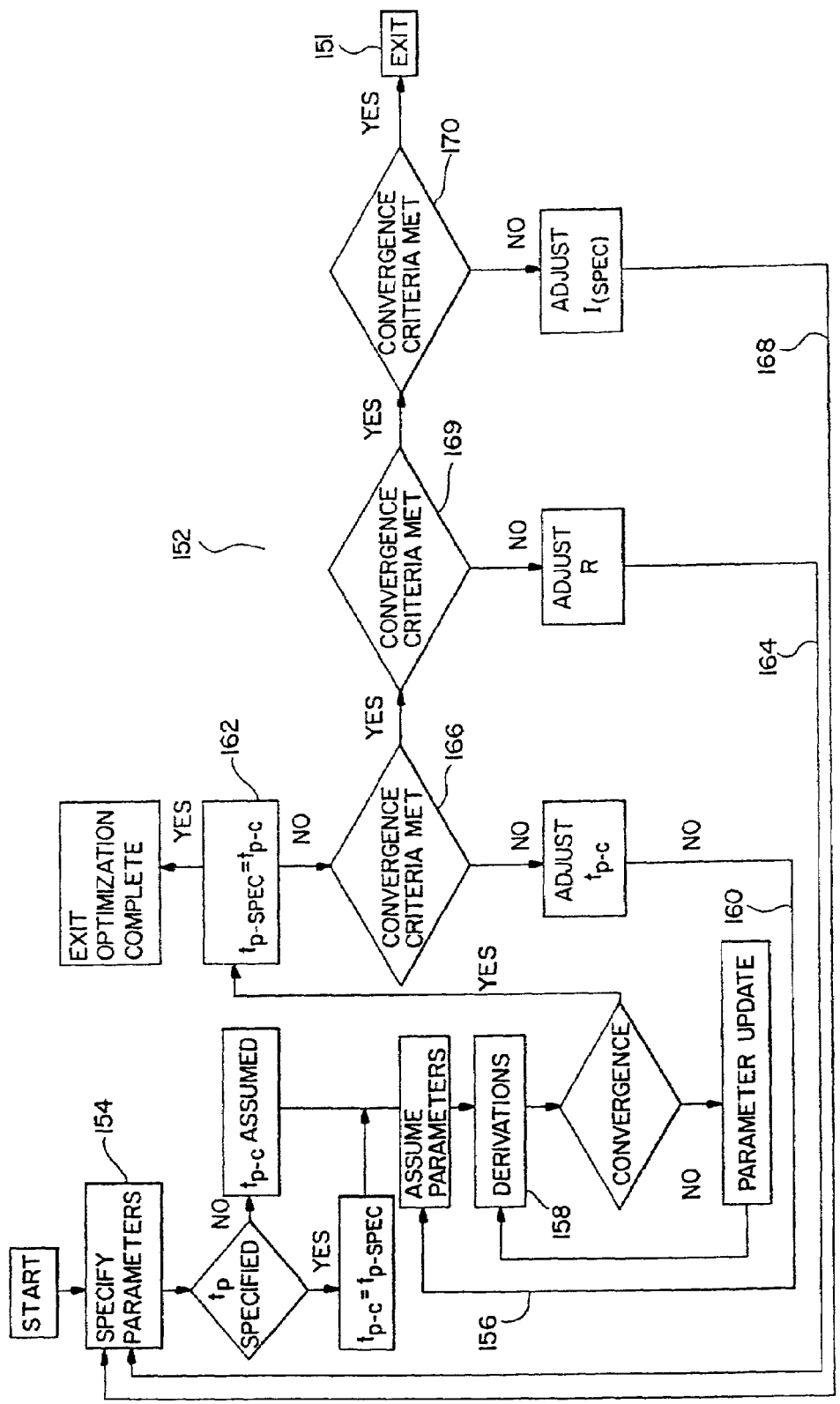
FIG. 9B is a flow chart of one optimization model for deriving at least one optimal process parameter from a desired blood component yield or from a total procedure time in accordance with principles of the present invention.

One model which may be incorporated into the manipulation device 144 is illustrated in FIG. 9B and will be described with regard to platelet collections in accordance with the dual needle configuration of FIG. 7A, although the device 144 may be used with a variety of other collection procedures and including the single needle configuration of FIG. 7B, as well as with various other blood components. Initially, it should be noted that all references in FIG. 9B to "derivations" are actually provided by the prediction model discussed above such that there is either an appropriate communication interface between the prediction model and manipulation device 144 or the manipulation device 144 actually includes the prediction model disposed thereon or therein. Moreover, as noted the prediction model described here is specific to the blood component collection machine 18 and to platelet collections. Therefore, if other machines are used, the associated prediction model would also likely change as noted. Moreover, the associated prediction model may also vary in the case where different blood components such as red blood cells are to be collected.

The optimizer model 152 of FIG. 9B may be used for both product-based and time-based optimizations. Initially, the optimizer model 152 will be described with regard to a product-based optimization. That is, the fundamental premise of the optimization is to achieve a predetermined platelet (or other blood component type) yield (or within a yield range), preferably in the minimum amount of time.

The optimizer model 152 of FIG. 9B is comprised of four iterative loops. Generally, the first loop 156 is a derivation of an inlet flow ($Q_{IN}$) associated with a specified AC infusion rate ($I_{SPEC}$) which is typically set at a maximum value for purposes of the present invention and which is entered at the input station 154. This derivation is thereafter performed by the processing station 158 and includes the solution of Eqs. 4, 8, 14, and 16 and/or equations ancillary thereto by the prediction model as discussed above.

There are of course various convergence criterion/criteria which may be incorporated into the first loop 156. For instance, convergence may be based upon the current inlet flow ($Q_{IN-C}$) in the first loop 156 through use of a binary search technique. In this case, in solving the noted equations at the processing station 158 certain parameters remain fixed in the iterative derivation of the inlet flow ($Q_{IN}$) which achieves the specified AC infusion rate ($I_{SPEC}$) and these parameters are also specified at input station 154. These include the total blood volume ($V_B$) which can be calculated using Eq. 10 since the donor's height, weight, and gender are entered at the central input station 148, and the AC ratio (R), which can be calculated using Eq. 9 since the donor's hematocrit (H) has been determined, or may be specified at some value. Moreover, the total procedure time ($t_P$) remains fixed in each iterative derivation of the inlet flow ($Q_{IN}$) associated with the specified AC infusion rate ($I_{SPEC}$) in the first loop 156. However, since the total procedure time ($t_P$) is not known in the case of a product-based optimization and thus cannot be specified at the input station 154, a current total procedure time ($t_{P-C}$) initially will be assumed (e.g., this assumption is configured in the optimizer model 152 and since a range of total procedure times is provided in the prediction model 20 as noted above, the mean total procedure time ($t_P$) is typically configured into this portion of the optimizer model 152 as the initial current total procedure time ($t_{P-C}$)). The "current" designation is used for the total procedure time in this case since the optimizer model 152 provides for an adjustment of the total procedure time after each iterative determination of the inlet flow ($Q_{IN}$) which provides the specified AC infusion rate ($I_{SPEC}$) in the second loop 160 in order to achieve the desired yield (Y) if required in the case of a product-based optimization as will be discussed in more detail below Generally, the inlet flow-based binary search technique convergence may be provided by assuming a current value for the inlet flow ($Q_{IN-C}$), calculating a current plasma collect factor ($P_C$) using the current total procedure time ($t_{P-C}$), calculating a current AC infusion rate ($I_C$) using the current inlet flow ($Q_{IN-C}$) and current plasma collect factor ($P_C$), and adjusting the current inlet flow ($Q_{IN-C}$) (at the parameter update in the first loop 156) in accordance with the selected binary search technique until there is a predetermined convergence between the two most recent values for the current inlet flow ($Q_{IN-C}$) (i.e., wherein the difference between the two most recent values of $Q_{IN-C}$ is less than some predetermined amount which means that the convergence criterion is met). In the case of a binary search technique, there will always be convergence (i.e., the convergence criterion will always be met) such that the optimizer model 152 will always exit the first loop 156 and enter the second loop 160.

As an alternative to the noted inlet flow-based convergence criterion/criteria and the noted binary search technique, another possibility is to base convergence on the specified AC infusion rate ($I_{SPEC}$) and use an iterative derivation to determine the desired inlet flow ($Q_{IN}$). In this case, the first loop 156 is used to once again iteratively derive the inlet flow ($Q_{IN}$) which provides the specified AC infusion rate ($I_{SPEC}$) at the processing station 158 from certain specified parameters. That is, the first loop 156 is still a maximization of the inlet flow ($Q_{IN}$) based upon the specified AC infusion rate ($I_{SPEC}$) which should be associated with the donor 14. This is again primarily through the solution of Eqs. 4, 8, 14, and 16 and/or equations ancillary thereto by the prediction model discussed above.

For purposes of solving the above-identified equations in relation to the infusion rate-based convergence criterion, certain parameters remain fixed in the iterative derivation of the inlet flow ($Q_{IN}$) which achieves the specified AC infusion rate ($I_{SPEC}$) in the first loop 156 and these parameters are also specified at the input station 154. These include the specified AC infusion rate ($I_{SPEC}$) which is known and which is typically a maximum value for the donor 14, the total blood volume ($V_B$) which can be calculated using Eq. 10 since the donor's 14 height, weight, and gender are entered in the central input station 148 or downloaded from a disparate information database, and the AC ratio (R) which can be calculated using Eq. 9 since the donor's 14 hematocrit (H) has been determined and input in the central input station 148 or otherwise downloaded, or may be entered as modified input data. Moreover, the total procedure time ($t_P$) remains fixed in each iterative derivation of the inlet flow ($Q_{IN}$) associated with the specified AC infusion rate ($I_{SPEC}$). However, once again the total procedure time ($t_P$) is not known in the case of a product-based optimization and thus cannot be specified at the input station 154. Therefore, a current total procedure time ($t_{P-C}$) initially will be assumed (e.g., this assumption is configured in the optimizer model 152, and since a range of total procedure times is provided in the prediction model as noted above, the mean total procedure time ($t_P$) is typically configured into the first loop 156 of the optimizer model 152). The "current" designation for the total procedure time is used for the above-identified reasons relating to the adjustment of the total procedure time in the second loop 160 if required to attain the desired yield (Y).

The solution of Eqs. 4, 8, 14, and 16 also requires that certain values be assumed for certain of the remaining parameters with still other parameters being derived from this assumption. In this case, an iterative procedure is used and updated/current values are used in the next iterative calculation(s). All parameters which change on each iteration of the first loop 156 are identified herein with a "c" subscript to designate that the most current value is to be used. Although the derivation of that inlet flow (QIN) which provides the specified AC infusion rate ($I_{SPEC}$) may be accomplished in a variety of manners via Eqs. 4, 8, 14, and 16, one way is to assume a current value for the plasma collect factor ($P_C$), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat this procedure with the current values until there has been acceptable convergence on the current inlet flow ($Q_{IN-C}$) in relation to the specified AC infusion rate ($I_{SPEC}$) (e.g., when the particular convergence criterion/criteria is met/established). When there is acceptable infusion rate-based convergence, the optimizer model 152 exits the first loop 156 and enters the second loop 160. In order to offer protection for cases when there is no such convergence, a maximum number of iterations for the first loop 156 may be specified (not shown).

The second loop 160 of the optimizer model 152 is a total procedure time ($t_P$) iteration. That is, the second loop 160 is an iterative adjustment of the current total procedure time ($t_{P-C}$). Initially, in the second loop 160 and in the case of a product-based optimization the model 152 will never exit at the first comparator 162 since a total procedure time ($t_P$) is not specified at the input station 154. Consequently, the optimizer model 152 proceeds to the second comparator 166 where convergence criteria (i.e., more than one check) is made. One convergence criterion which is checked at the second comparator 166 is whether the current yield ($Y_C$) is greater than or equal to the desired and specified yield (Y). in this case, the current yield ($Y_C$) may be calculated based upon the values specified at the input station 158, values derived at the processing station 158, and the current total procedure time ($t_{P-C}$) for comparison with the desired and specified yield (Y) (in some cases, this current yield calculation ($Y_C$) may have been performed in the first loop 156 and need not be repeated in the second loop 160). If the yield convergence criterion is met, the model 152 exits the second loop 160 and actually exits all the way through to the exit 151, as will be discussed below. In this case, the specified/derived values are "optimal" and the collection procedure could be performed on the device 18 using the noted values for the various control parameters.

In the event that the yield-based criterion is not met at second comparator 166, the second comparator 166 looks to a total procedure time-based convergence criterion which may be similar to that discussed above with regard to the inlet flow-based criterion (e.g., using a binary search technique with the convergence criterion then being a predetermined difference between the two most current values of the total procedure time ($t_{P-C}$)). On the first time through the second loop 160 after the noted yield-based convergence criterion has failed and the total procedure time convergence criterion has failed, the current total procedure time ($t_{P-C}$) is adjusted and the model 152 returns to the first loop 156. That is, each time that the current total procedure time ($t_{P-C}$) is adjusted in the second loop 160, the entirety of the first loop 152 is repeated (i.e., a new inlet flow ($Q_{IN}$) associated with the specified AC infusion rate ($I_{SPEC}$) is derived using the current total procedure time ($t_{P-C}$) provided by the adjustment in the second loop 160). Other convergence criterion/criteria could be used in the second loop 160, such as specifying a maximum number of iterations to be performed by the second loop 160.

In the event that the yield-based convergence criterion is not met on the second loop 160 and the total procedure time-based convergence criterion is met at the second comparator 166 in the second loop 160, the optimizer model 152 exits the second loop 160 and enters the third loop 164. The third loop 164 is an iterative adjustment of the AC ratio (R). However, the model 152 initially enters the third comparator 169 where convergence criteria (i.e., more than one) are checked. One convergence criterion is again the above-noted yield-based convergence criterion. If this yield-based convergence criterion is again not met, an AC ratio-based convergence criterion is checked at the third comparator 169. This may be similar to the inlet flow-based criterion discussed above (e.g., using a binary search technique with the convergence criterion being the two most current values of the AC ratio). On the first time through the third loop 164 after the yield-based criterion has failed and the AC ratio-based convergence criterion has failed, the AC ratio is adjusted and the optimizer model 152 returns to the first loop 152. That is, each time that the AC ratio (R) is adjusted in the third loop 164, the entirety of the first and second loops 156, 160, respectively, is repeated. Other convergence criterion/criteria could be used in the third loop 164, such as specifying a maximum number of iterations of the third loop 164.

In the event that the yield-based convergence criterion is not met in the second or third loops 160, 164, respectively, and the second and third comparator 166, 169, respectively, and the AC ratio-based convergence criterion is met at the third comparator 169 in the third loop 164, the optimizer model 152 exits the third loop 164 and enters the fourth loop 168. The fourth loop 168 is an iterative adjustment of the specified AC infusion rate ($I_{SPEC}$). However, the optimizer model 152 initially enters the fourth comparator 170 where convergence criteria (i.e., more than one) are checked. One convergence criterion is the noted yield-based convergence criterion. If the noted yield-based convergence criterion is not met at the fourth comparator 170, an AC infusion rate-based criterion is checked at the fourth comparator 170. This may be similar to the inlet-flow based criterion discussed above (e.g., using a binary search technique with the convergence criterion being the two most current values of the AC infusion rate). On the first time through the fourth loop 168 after the yield-based criterion has failed and the AC infusion rate-based convergence criterion has failed, the AC infusion rate is adjusted and the model 152 returns to the first loop 152. That is, each time that the specified AC infusion rate ($I_{SPEC}$) is adjusted, the entirety of the first, second and third loops 156, 160, 164, respectively, is repeated (with the AC ratio set back to its initial value as entered at the input station 154 on each iteration of the fourth loop 168). Other convergence criterion/criteria could be used in the fourth loop 168, such as specifying a maximum number of iterations of the fourth loop 168. In cases where the specified AC infusion rate ($I_{SPEC}$) is actually the maximum AC infusion rate, typically the fourth loop 168 will execute only a single time with a one-time increase in the AC infusion rate of, for instance, 20% (e.g., may be site-configured).

In the foregoing loops where a yield-based convergence criteria are identified, when the criteria are met the optimizer model 152 exits to exit 151 and the specified/derived (i.e., current) values for the various process control parameters may be provided to the device 18 for performing the collection procedure. However, there may be cases where no optimization occurs, such as when the optimizer model 152 exits to the exit 151 based upon the AC infusion rate based convergence criterion being met.

The optimizer model 152 may also be used for a time optimization. That is, the optimizer model will derive optimal process parameters for a predetermined total procedure time ($t_P$) through maximization of at least one of the process parameters in order to maximize the platelet collection (or for other blood component types). In this case, the optimizer model 152 only executes the first loop 156 to derive the inlet flow ($Q_{IN}$) associated with a specified AC infusion rate ($I_{SPEC}$) (typically a maximum value) using the input total procedure time ($t_P$) in this iterative derivation instead of the assumed total procedure time ($t_P$) referenced above. Once there is acceptable convergence as defined above in the product-based optimization such that model 152 exits the first loop 156, the current yield ($Y_C$) may be calculated in the first loop 156 (but again may already have been calculated in the first loop 156 at the processing station 158 such that no further calculation is required) and the convergence criterion will be met at the first comparator 162 when entering the second loop 160 (i.e., in a time-based optimization when a total procedure time is specified at the input station 154, the model 152 will exit when entering the second loop 158). As a result, the inlet flow ($Q_{IN}$) and AC infusion rate (I) will be optimal and the collection procedure may be performed with such values.

Figure 9C:
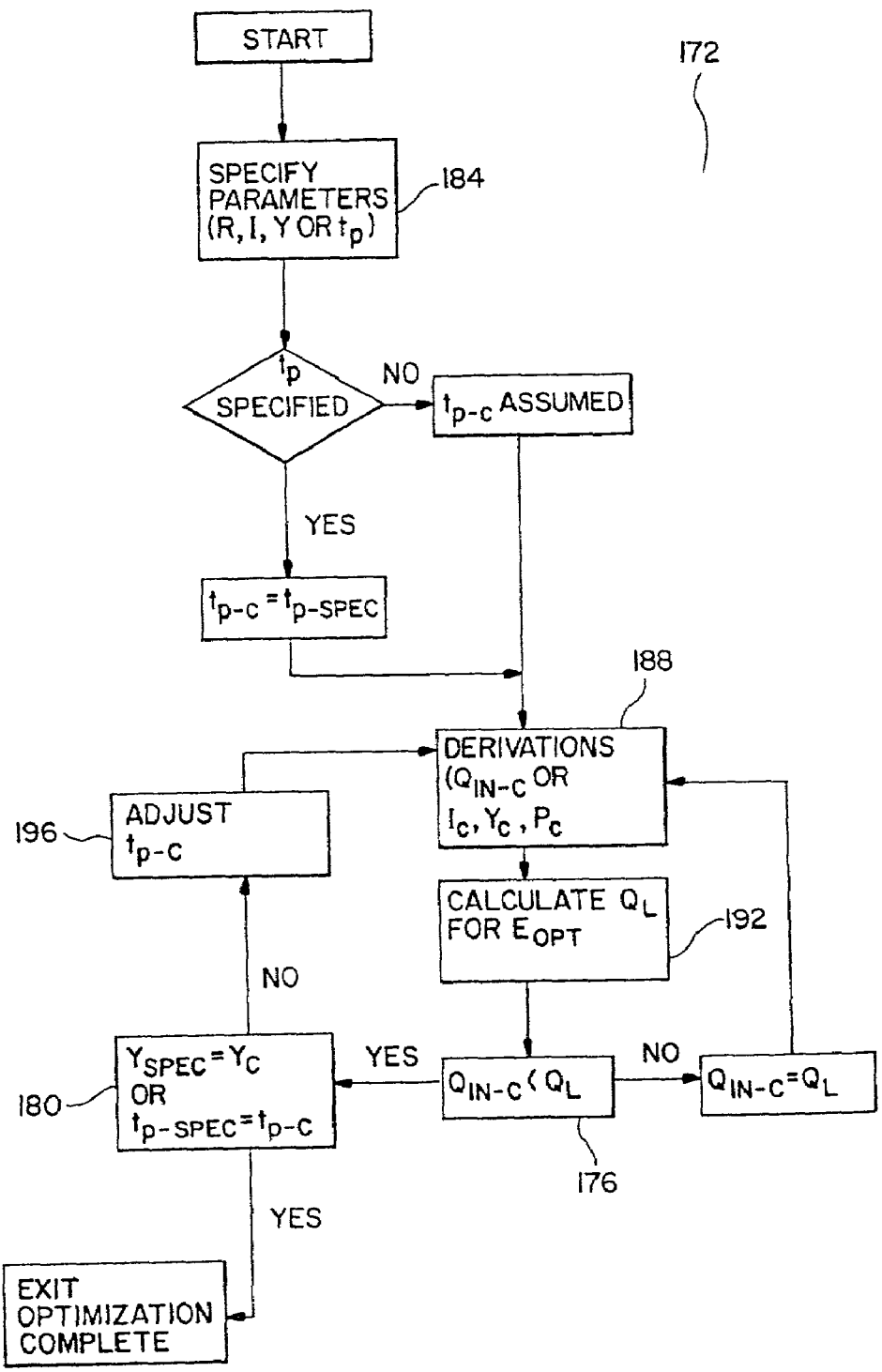
FIG. 9C is a flow chart of one optimization model for deriving at least one optimal process parameter from a desired blood component yield or from a total procedure time in accordance with principles of the present invention.
Figure 10:
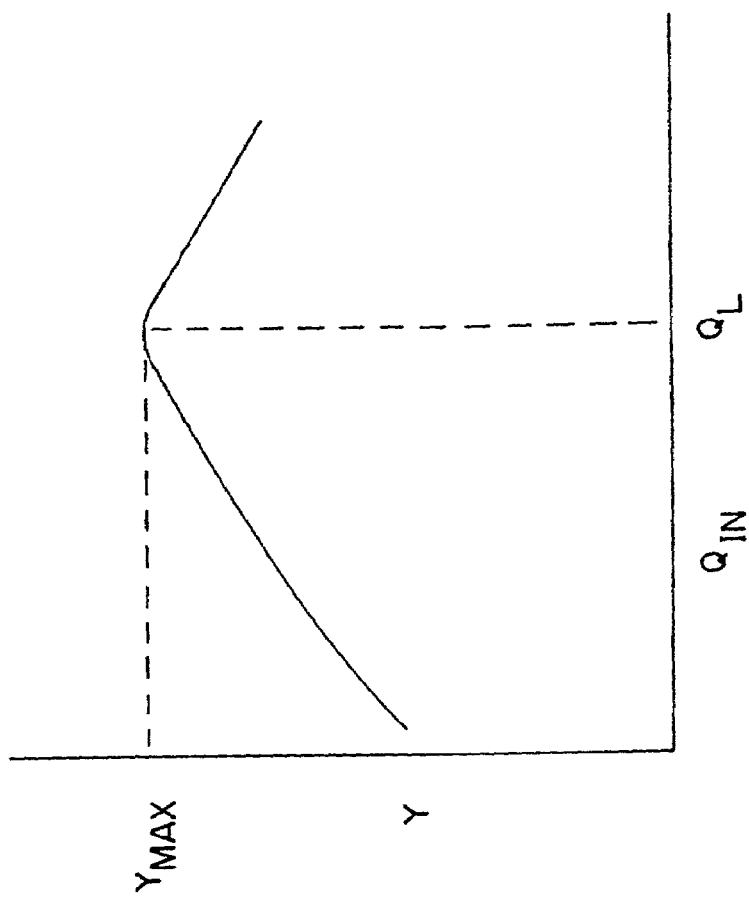
FIG. 10 is a yield/inlet flow curve.

Another optimization model is presented in FIG. 9C and may be used for both product-based and time-based optimizations. As in the case of the optimizer model 152, the optimizer model 172 may interface with the prediction model or actually integrally incorporate the prediction model, and thus reference to Eqs. 1–22 will be further made herein. Generally, the optimizer model 172 is based upon the principle that optimization occurs when an optimal inlet flow ($Q_L$) associated with an optimum system collection efficiency is used in the derivation of various process control parameters. Referring to FIG. 10, a representative inlet flow ($Q_{IN}$)/yield (Y) curve is presented to show the optimal inlet flow ($Q_L$) associated with the maximum yield ($Y_{MAX}$). This optimal inlet flow ($Q_L$) is mathematically expressed by Eq. 23 presented below which results from differentiating Eq. 4 of the prediction model with regard to the inlet flow ($Q_{IN}$). As can be appreciated, where different algorithms are used in the associated prediction model (whether based upon collection of blood components other than platelets, different collection apparatus, or alternative derivations of the various parameters with the same collection procedure and apparatus), the optimal inlet flow may be mathematically expressed in a different manner.

$$Q_L = \left(\frac{C_1}{2C_2}\right) e^{-9.91(1-1/R)H} - C_3 \quad \text{(Eq. 23)}$$

$$C_3 = \frac{1}{2(t_P/K_7 - 1/K_9)}, \quad \begin{array}{l} Q_O \geq 45 \text{ for Dual Needle("}DN\text{")} \\ \geq 20 \text{ for Single Needle("}SN\text{")} \end{array} \quad \text{(Eq. 24)}$$

i $Q_O$<45 for $DN$=$O$, <20 for $SN$ \quad (Eq. 25)

$K_7$=500($DN$)$K_9$=45($DN$)=215($SN$)=20($SN$) \quad (Eq. 26)

$C_1$=0.803($SN$, $DN$ without stepdown)=0.840($DN$ with stepdown) \quad (Eq. 27)

$C_2$=4.08×10$^{-5}$($DN$)=854×10$^{-5}$($SN$) \quad (Eq. 28)

Based upon the foregoing, the optimal inlet flow ($Q_L$) is really "optimal" in terms of the collection apparatus.

Referring again to FIG. 9C, the optimizer model 172 will initially be described with regard to a product-based optimization wherein the desired yield (Y) is specified at input station 184. Generally, the inlet flow ($Q_{IN}$) associated with a specified AC infusion rate ($I_{SPEC}$) (typically the maximum AC infusion rate and also specified at input station 184) is iteratively derived from certain other specified parameters. This inlet flow calculation, particularly when the maximum AC infusion rate ($I_{MAX}$) and maximum AC ratio ($R_{MAX}$) are specified, the inlet flow ($Q_{IN}$) is optimal based on the physiological considerations of the donor 14. This is primarily through the solution of Eqs. 4, 8, 14, and 16 and/or equations ancillary thereto by the prediction model discussed above. For purposes of solving these equations certain parameters remain fixed in the iterative derivation of the inlet flow ($Q_{IN}$) which achieves the specified AC infusion rate ($I_{SPEC}$) and these parameters are also specified at input station 184. These include the total blood volume ($V_B$) which can be calculated using Eq. 10 since the donor's height, weight, and gender are entered in the central input station 148, and the AC ratio (R), which can be calculated using Eq. 9 since the donor's hematocrit (H) has been determined, or may be specified at some maximum value. Moreover, the total procedure time ($t_P$) remains fixed in each iterative derivation of the inlet flow ($Q_{IN}$) associated with the specified AC infusion rate ($I_{SPEC}$). However, since the total procedure time (tP) is not known in the case of a product-based optimization and thus cannot be specified at the input station 184, a current total procedure time ($t_{P-C}$) initially will be assumed (e.g., this assumption is configured in the optimizer model 172 and since a range of total procedure times is provided in the prediction model as noted above, the mean total procedure time ($t_P$) is typically configured into this portion of the optimizer model 172 as the initial current total procedure time ($t_{P-C}$)). The "current" designation is used for the total procedure time in this case since the optimizer model 172 provides for an adjustment of the total procedure time after each iterative determination of the inlet flow ($Q_{IN}$) which provides the specified AC infusion rate ($I_{SPEC}$) in order to achieve the desired yield (Y) if required in the case of a product-based optimization as will be discussed in more detail below.

The solution of Eqs. 4, 8, 14, and 16 also requires that certain values initially be assumed for certain of the remaining parameters. In this case, an iterative procedure is used in the solution of the yield equation (Eq. 4) (and including equations ancillary thereto as noted above) and updated values are used in the next iterative calculation(s) at the processing station 188. Although the derivation of that inlet flow ($Q_{IN}$) which provides the specified (typically maximum) AC infusion rate ($I_{SPEC}$) may be accomplished in a variety of manners via Eqs. 4, 8, 14, and 16, one way is to assume a current value for the plasma collect factor (P), then calculate the current inlet flow ($Q_{IN-C}$) using the specified AC infusion rate ($I_{SPEC}$), then calculate the current yield ($Y_C$), then calculate the current plasma collection factor ($P_C$) using the current yield ($Y_C$), and repeat the foregoing with the updated parameters, all within the processing station 188, until there has been acceptable convergence on the current inlet flow ($Q_{IN-C}$) in relation to the specified AC infusion rate ($I_{SPEC}$).

In addition to the calculation of the current inlet flow ($Q_{IN-C}$) associated with the specified AC infusion rate ($I_{SPEC}$), the above-discussed optimal inlet flow ($Q_L$) is calculated at processing station 192. Consequently, a comparison can be made between the current inlet flow ($Q_{IN-C}$) which was derived in the above-described manner and the optimal inlet flow ($Q_L$) at the first comparator 176. If the current inlet flow ($Q_{IN-C}$) is less than the optimal inlet flow ($Q_L$) at the first comparator 176, the specified values for the various parameters associated with the inlet flow $Q_{IN}$ are "optimum", namely the AC ratio (R) and the AC infusion rate (I) specified at the input station 184. Thereafter, the current yield ($Y_C$) (which was calculated in the derivation of the current inlet flow ($Q_{IN-C}$) associated with the specified AC infusion rate ($I_{SPEC}$) at the processing station 188) is compared with the input yield (Y) at second comparator 180. In the event that there has been acceptable convergence between these yield values, the current total procedure time ($t_{P-C}$) is also "optimal". However, in the event that there has not been acceptable convergence between these yield values, the current total procedure time ($t_{P-C}$) is adjusted at adjusting station 196 and the foregoing iterative derivation of the current inlet flow ($Q_{IN-C}$) associated with the specified AC infusion rate ($I_{SPEC}$) is repeated until such convergence is achieved (i.e., using the initially specified AC infusion rate ($I_{SPEC}$) and the now adjusted current total procedure time ($t_{P-C}$, a new current inlet flow ($Q_{IN-C}$) is iteratively derived in the above-described manner).

Referring back to the first comparator 176, if the current inlet flow ($Q_{IN-C}$) associated with the specified AC infusion rate ($I_{SPEC}$) derived at processing station 188 is greater than the optimal inlet flow ($Q_L$), a current AC infusion rate ($I_C$) associated with this particular inlet flow ($Q_L$) is iteratively derived at the processing station 188 generally in the above-described manner (i.e., the initially specified AC infusion rate ($I_{SPEC}$) is disregarded in this derivation and a current AC infusion rate ($I_C$) is iteratively derived to coincide with the inlet flow ($Q_L$)). In this case, the current inlet flow ($Q_{IN-C}$) will always be equal to the optimal inlet flow ($Q_L$) at the first comparator 176 and the optimizer model 172 thereafter proceeds to the second comparator 180 for the yield comparison in accordance with the above-described procedure.

The optimizer model 176 may also be used for a time-based optimization. In this case, the total procedure time ($t_P$) is specified at the input station 184 as a specified total procedure time ($t_{P-SPEC}$) and thus is not assumed as in the product-based optimization. The optimizer model 172 thereafter proceeds in the same manner discussed above with regard to the product-based optimization except at the second comparator 180. Since no yield was input there is no yield comparison made at the second comparator 180. Instead a total procedure time comparison is made at the second comparator 180. Since the current total procedure time ($t_{P-C}$) was set equal to the specified total procedure time ($t_{P-SPEC}$) prior to the model 172 proceeding to the processing station 188 in this time-based optimization, the model 172 will exit each time at the second comparator for a time-based optimization.

In addition to the above-described product-based and time-based optimizations, the principles of the present invention may be extended to other applications relating to enhancing blood component system management. For instance, an optimization in accordance with principles of the present invention may be extended to encompass donor management issues. In one such case, another "optimization" associated with the blood component collection process would be to collect blood components as dictated by existing inventory (i.e., use optimization as an inventory control). That is, information relating to the inventory of the various types of blood components in the blood bank/center and/or the demand for one or more blood component types could be maintained such that specific collection procedures could be selected to accommodate for a low supply of a given blood component type and/or a high demand for such blood component type. More specifically, in the event that the supply of red blood cells was low and/or the demand for red blood cells was high, or anticipated to be so in the near future, prompts could be provided to operators that red blood cells should be selected for collection if possible from donors during a given time period. Relatedly, the optimization principles of the present invention would be applicable to maintaining data on blood component collections from a given donor such that a determination could be made as to what type or types of blood components from the particular donor provided the maximum yield in the collection procedure. That is, information could be collected and maintained from prior blood component donations such that a determination could be made for a specific donor as to which type or types of blood components the donor has had a propensity to produce maximum yields therefor.

Notwithstanding the foregoing description of the present invention in relation to an on-line blood component collection process, those skilled in the art will appreciate that the source of blood may be provided to the blood component collection device from an appropriate blood container (not shown) interconnected with the blood component collection device 18 versus receiving such directly from a human donor. Moreover, the blood of course may be provided from alternative sources such as animals. Furthermore, as illustrated in FIG. 7B the described component (platelet, RBC, plasma, inter alia) harvesting procedure may be performed utilizing a single needle configuration. In addition, the present invention is applicable to the collection of other types of blood components such as red blood cells, stem cells, white blood cells, and/or plasma, and is further applicable to the simultaneous collection of more than one blood component type. In the case of red blood cell collection and optimization in accordance with principles of the present invention, the donor's blood type should be known and used in various algorithms. Moreover, the present invention is not limited to the source being whole blood. That is, the principles of the present invention may be applicable to removal of a component from any composite liquid, i.e. any liquid containing separable components (preferably separable using mechanical procedures).

The foregoing description of the present invention has been presented for purposes of illustration and description. Although the preferred embodiment of the invention has been described in language which may be thought specific to structural features, methodological acts, and computer readable media containing such acts, it is rather intended to be understood that the invention defined in the appended claims is not necessarily limited to the specific structure, acts or media so described. The specific structure, acts or media are disclosed as preferred forms of implementing the claimed invention. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention, and such other embodiments, and with various modifications required by the particular applications or uses of the present invention. It is intended that the appended claims be construed to include alternative embodiments to the extent permitted by the prior art.

What is claimed is:

1. An extracorporeal blood processing information management system for use with a plurality of extracorporeal blood processing machines, said system comprising:
   a machine network, said machine network having
      a plurality of extracorporeal blood processing machines; and
      a server in data communication with said extracorporeal blood processing machines;
   a central database in data communication with said server;
   a client network, said client network having
      a terminal server in data communication with said central database; and
      a plurality of data input devices connected in data communication relationship with said terminal server; and
   a data manipulation device connected in data communication relationship with said central database, in which said central database contains data concerning demand for selected blood products, said data being manipulated by said data manipulation device to create manipulated preparation data which is communicated to at least one machine of said extracorporeal blood processing machines, said manipulated preparation data being used by said extracorporeal blood processing machine in preparation of said machine for an extracorporeal blood processing procedure.

2. An extracorporeal blood processing information management system according to claim 1 in which said manipulated preparation data comprises optimized preparation data as a result of an optimization manipulation performed by said data manipulation device.

3. An extracorporeal blood processing information management system according to claim 1 whereby said machine network communicates data from said extracorporeal blood processing machines to said central database, whereby this data is run data which represents information about an extracorporeal blood processing procedure run on at least one of said blood processing machines.

4. An extracorporeal blood processing information management system according to claim 1 wherein said information management system is a discrete blood center information management system.

5. An extracorporeal blood processing information management system according to claim 1 wherein said information management system is in data communication with a discrete hospital information management system.

6. An extracorporeal blood processing information management system according to claim 1 wherein said information management system is in data communication with a discrete help center information management system.

7. An extracorporeal blood processing information management system according to claim 1 wherein said information management system is in data communication with a discrete internet information management system.

8. An extracorporeal blood processing information management system according to claim 1 wherein said information management system is in data communication with a discrete manufacturers' information management system.

* * * * *